United States Patent
Becker et al.

(10) Patent No.: US 10,765,748 B2
(45) Date of Patent: Sep. 8, 2020

(54) COMPOSITION AND METHODS FOR TETHERING BIOACTIVE PEPTIDES TO METAL OXIDE SURFACES

(71) Applicants: Matthew Becker, Stow, OH (US); Wen Tang, Akron, OH (US)

(72) Inventors: Matthew Becker, Stow, OH (US); Wen Tang, Akron, OH (US)

(73) Assignee: University of Akron, Akron, OH (US)

( * ) Notice: Subject to any disclaimer, the term of this patent is extended or adjusted under 35 U.S.C. 154(b) by 20 days.

(21) Appl. No.: 15/325,218

(22) PCT Filed: Jul. 13, 2015

(86) PCT No.: PCT/US2015/040112
§ 371 (c)(1),
(2) Date: Jan. 10, 2017

(87) PCT Pub. No.: WO2016/007943
PCT Pub. Date: Jan. 14, 2016

(65) Prior Publication Data
US 2017/0189531 A1      Jul. 6, 2017

Related U.S. Application Data

(60) Provisional application No. 62/023,292, filed on Jul. 11, 2014.

(51) Int. Cl.
*A61K 47/10* (2017.01)
*C07K 14/51* (2006.01)
*C07K 7/08* (2006.01)

(52) U.S. Cl.
CPC ............. *A61K 47/10* (2013.01); *C07K 7/08* (2013.01); *C07K 14/51* (2013.01)

(58) Field of Classification Search
None
See application file for complete search history.

(56) References Cited

U.S. PATENT DOCUMENTS

| | | | |
|---|---|---|---|
| 2010/0104512 A1* | 4/2010 | Felder-Flesch | A61K 49/124 424/1.65 |
| 2010/0305626 A1* | 12/2010 | Stewart | A61L 24/0015 606/86 R |
| 2012/0310540 A1* | 12/2012 | McDermitt | G01N 21/6486 702/19 |
| 2014/0271500 A1* | 9/2014 | Brody | A61K 8/64 424/54 |
| 2014/0288150 A1* | 9/2014 | Guan | C08G 75/14 514/44 A |

FOREIGN PATENT DOCUMENTS

WO     WO 2012/166594 A1 *  12/2012
WO        2013/183048 A1    12/2013

OTHER PUBLICATIONS

Tang et al. Hydroxyapatite-Targeting Dendrons and Its Application As Osteoinductive Peptide Sequestering. Department of Polymer Science. Mar. 16, 2014 [Online: http://ideaexchange.uakron.edu/polymerscience_ideas/830>; pp. 1-2) (Tang I).*
Tang et al. Valency-Dependent Affinity of Bioactive Hydroxyapatite-Binding Dendrons. Biomacromolecules. Jul. 26, 2013, vol. 14; pp. 3304-3313 (Tang II).*
Gillich et al. Self-Assembly of Focal Point Oligo-Catechol Ethylene Glycol Dendrons on Titanium Oxide Surfaces: Adsorption Kinetics, Surface Characterization, and Nonfouling Properties. Journal of the American Chemical Society. Jul. 2, 2011, vol. 133; pp. 10940-10950.*
Tang et al. ("HA-binding peptide functionalized dendron: Synthesis and application as a BMP-2 peptide carrier". Abstracts of Papers , 244th ACS National Meeting & Exposition, Philadelphia, PA, United States, Aug. 19-23, 2012 (2012), MEDI-383. American Chemical Society: Washington, D. C.).*
Tang et al., "A Hydroxyapatite (HA)-Binding Peptide Functionalized Dendron: Design, Synthesis and application as a Growth Factor Carrier" published on the University of Akron website at least as early as Feb. 7, 2013.*
Lee, JS et al.: "Modular Peptide Growth Factors for Substrate Mediated Stem Cell Differentiation.", Angew Chem Int Ed Engl., vol. 48, No. 34,2009, pp. 6266-6269, XP055097248.

* cited by examiner

*Primary Examiner* — Maury A Audet
(74) *Attorney, Agent, or Firm* — Renner Kenner Greive Bobak Taylor & Weber

(57) ABSTRACT

In various aspects, embodiments of the present invention are directed to a series of multivalent dendrons containing a bioactive peptide domain and surface-binding catechol domains. In some embodiments, these multivalent dendrons were obtained through solid phase synthesis and have a strong binding affinity to metal oxide surfaces such as, $TiO_2$, $ZrO_2$, $CeO_2$, and $Fe_3O_4$, $SiO2$, as well as other inorganic surfaces such as hydroxyapatite, silver, fluorapatite, calcium carbonate and gold. These catechol-bearing dendrons provide a fast and efficient method to functionalize a wide range of inorganic materials with bioactive peptides and have the potential to be used in coating orthopaedic implants and fixation devices.

20 Claims, 18 Drawing Sheets
Specification includes a Sequence Listing.

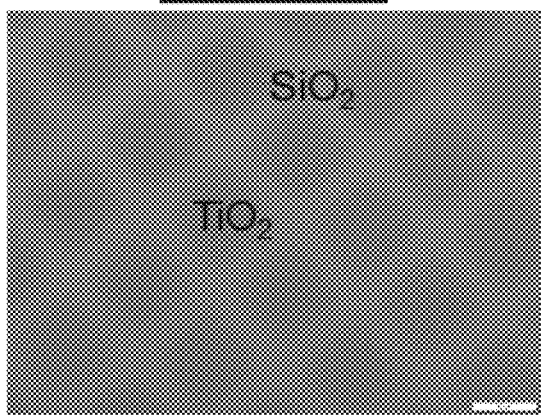
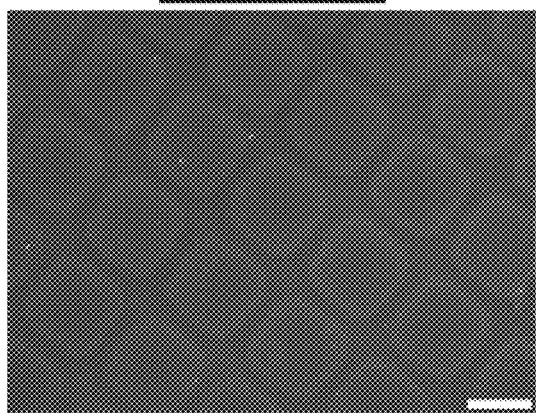
FIG. 10A
FIG. 10B
FIG. 11
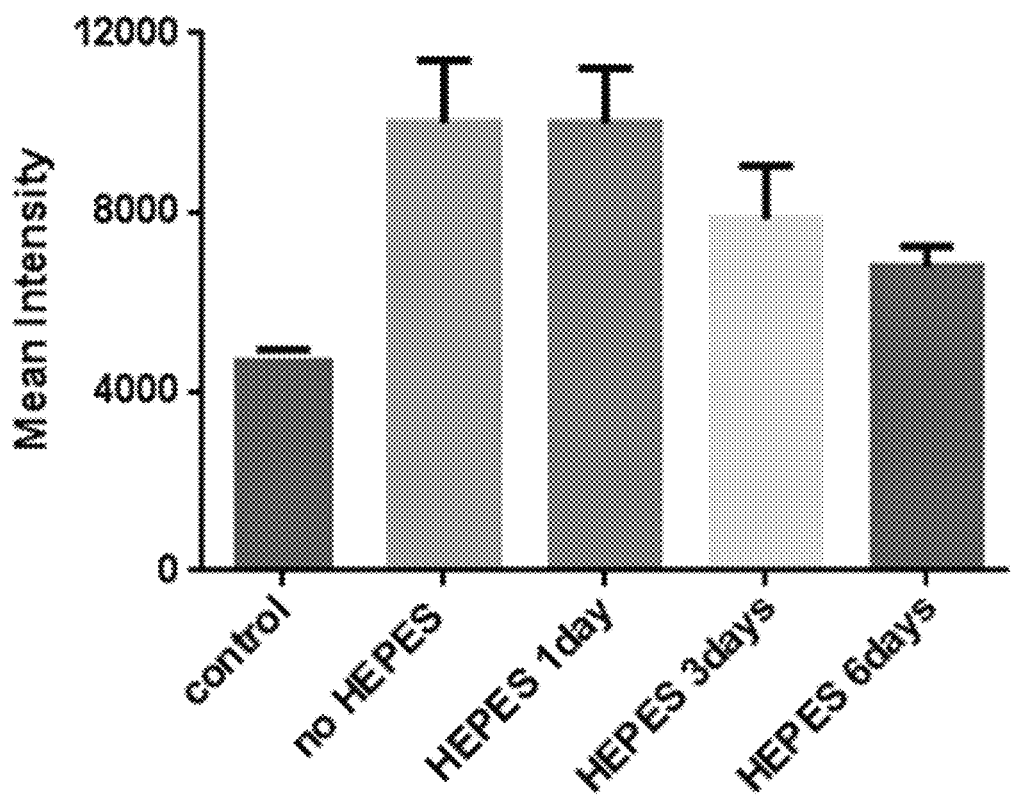

SEQUENCE LISTING

<160> NUMBER OF SEQ ID NOS: 9

<210> SEQ ID NO 1
<211> LENGTH: 20
<212> TYPE: PRT
<213> ORGANISM: Artificial
<220> FEATURE:
<223> OTHER INFORMATION: bioactive peptide sequence.

<400> SEQUENCE: 1

Lys Ile Pro Lys Ala Ser Ser Val Pro Thr Glu Leu Ser Ala Ile Ser
1               5                   10                  15

Thr Leu Tyr Leu
            20

<210> SEQ ID NO 2
<211> LENGTH: 18
<212> TYPE: DNA
<213> ORGANISM: Artificial
<220> FEATURE:
<223> OTHER INFORMATION: hGAPDH-L1 primer sequence.

<400> SEQUENCE: 2
gacagtcagc cgcatctt                                                 18

<210> SEQ ID NO 3
<211> LENGTH: 20
<212> TYPE: DNA
<213> ORGANISM: Artificial
<220> FEATURE:
<223> OTHER INFORMATION: hGAPDH-R1 primer sequence.

<400> SEQUENCE: 3
ccatggtgtc tgagcgatgt                                               20

<210> SEQ ID NO 4
<211> LENGTH: 20
<212> TYPE: DNA
<213> ORGANISM: Artificial
<220> FEATURE:
<223> OTHER INFORMATION: hBSP-L1 primer sequence.

<400> SEQUENCE: 4
cctggcacag ggtatacagg                                               20

<210> SEQ ID NO 5
<211> LENGTH: 20
<212> TYPE: DNA
<213> ORGANISM: Artificial
<220> FEATURE:
<223> OTHER INFORMATION: hBSP-R1 primer sequence.

<400> SEQUENCE: 5
ctgcttcgct ttcttcgttt                                               20

```
<210> SEQ ID NO 6
<211> LENGTH: 19
<212> TYPE: DNA
<213> ORGANISM: Artificial
<220> FEATURE:
<223> OTHER INFORMATION: hOCN-L1 primer sequence

<400> SEQUENCE: 6
gtgcagcctt tgtgtccaa                                           19

<210> SEQ ID NO 7
<211> LENGTH: 17
<212> TYPE: DNA
<213> ORGANISM: Artificial
<220> FEATURE:
<223> OTHER INFORMATION: hOCN-R1 primer sequence

<400> SEQUENCE: 7
ggctcccagc cattgat                                             17

<210> SEQ ID NO 8
<211> LENGTH: 5
<212> TYPE: PRT
<213> ORGANISM: Artificial
<220> FEATURE:
<223> OTHER INFORMATION: bioactive peptide sequence

<400> SEQUENCE: 8

Tyr Gly Phe Gly Gly
1               5

<210> SEQ ID NO 9
<211> LENGTH: 5
<212> TYPE: PRT
<213> ORGANISM: Artificial
<220> FEATURE:
<223> OTHER INFORMATION: Artificial peptide sequence

<400> SEQUENCE: 9

Gly Arg Gly Asp Ser
1               5
```

COMPOSITION AND METHODS FOR TETHERING BIOACTIVE PEPTIDES TO METAL OXIDE SURFACES

CROSS REFERENCE TO RELATED APPLICATIONS

This application claims the benefit of International Application No. PCT/US2015/020112, which claims the benefit of U.S. provisional patent application Ser. No. 62/023,292 entitled "Methods and Molecules for Tethering Bioactive Peptides to Metal Oxide Surfaces," filed Jul. 11, 2014, both of which are incorporated herein by reference in their entirety.

REFERENCE TO GOVERNMENT SUPPORT

This invention was made with government support under grant number DMR-1105329 awarded by the National Science Foundation. The government has certain rights in the invention.

FIELD OF THE INVENTION

One or more embodiments of the present invention relate to a molecule for the attachment of bioactive peptides to metal oxide and other surfaces. In certain embodiments, the present invention relates a multivalent amino acid-based Dendron having a bioactive peptide at its focal point and one or more surface-binding catechol groups.

REFERENCE TO AN ELECTRONIC SEQUENCE LISTING

The contents of the electronic sequence listing (UOA1147AmendedSequenceListingST25.txt; Size: 1,900 bytes; and Date of Creation: May 31, 2017) is incorporated herein by reference in its entirety.

BACKGROUND OF THE INVENTION

Immobilization of bioactive peptides onto surfaces has been proven to be an effective avenue to improve cell attachment, influence proliferation, and direct differentiation in tissue engineering. Physical adsorption/encapsulation and chemical conjugation have both been applied to derivatize tissue engineering scaffolds with bioactive peptides. Most of these methods were developed for polymeric materials, while the surface decoration of inorganic surfaces has received less attention, due to the lack of diversity in presenting functional groups for highly efficient chemical reactions. However, many inorganic materials are useful in the medical applications field. For instance, titanium and zirconia are widely used in prosthetic devices and dental implants; cerium oxide nanoparticles are potent antioxidants in therapeutics; and iron oxide magnetic nanoparticles are used to enhance the magnetic resonance imaging contrast in disease diagnostics. Thus the development of efficient and convenient methods to immobilize bioactive peptides onto the surface of metal oxide materials ($TiO_2$, $ZrO_2$, $CeO_2$, $Fe_3O_4$, etc.) will not only influence the cell behavior locally, but will also contribute to the improvement of diagnostic and therapeutic techniques in the clinic.

Titanium is the most widely used material in bone implants and dental fixations due to its low density, high strength and high resistance to erosion. In physiological conditions, the oxide passivation layer of 2-20 nm $TiO_2$ is quickly formed on titanium implants. Several methods have been developed to decorate titanium implants with bioactive peptides/proteins. Modifications can be achieved through physical interactions, such as protein-encapsulated coating, erosion and subject protein adsorption, and peptide-grafted polycation adsorption. However, the diffusion of loaded bioactive components may require high doses, and lead to low drug efficiency, and other adverse reactions. Chemical conjugation by generating reactive functional groups using electrochemical anodization, acid-etching, and oxidation, have been utilized to covalently conjugate the bioactive moieties onto the titanium implant surface, but the methods require complicated procedures and change the surface properties of the device during fabrication.

The presence of 3,4-dihydroxyphenylalanine (DOPA), which is found abundantly in mussel adhesive proteins, has been connected to the strong adhesion of mussels onto multiple surfaces in wet conditions. Catechol group is the functional group of DOPA, which is known to interact with titanium oxide surface through coordination bond or H-bond with pH sensitivity. Catechol is also crosslinked together under oxidative or basic conditions to form coating layers on surfaces. Thus it has been served as adhesive building blocks in the surface coating of variety of materials, including metal oxides, and organic polymers. Besides titanium oxide, the interaction of catechol with other metal oxides has also been studied, including iron oxide, chromium(III) oxide manganese dioxide, aluminium oxide and zirconia. Anti-fouling ethylene glycol dendrons and glycocalyx layers have been successfully coated onto titanium oxide surfaces with catechol-functionalized oligomers as the surface-anchoring domain. However, sequestering bioactive moieties, such as peptides that are known to direct cell behaviors, using catechol-bearing molecules on the surfaces of biomaterials has not been reported.

Modular peptides are conjugated molecules containing several different peptide sequences that are known to have specific bio-functionality. In the modular peptides, there are two active components, the surface-binding peptide that sequesters the whole molecule on the surface and the bioactive subunit that influences the cell behavior. The loading concentration and retention time of the peptides on the surface are critical parameters that determine whether molecular signaling in the cell will be triggered. In many studies it was shown that the cell response to specific peptides is concentration-dependent. However, in most applications, the concentrations that are required to trigger and sustain the cell response are less understood. Strong adsorption is the prerequisite to realize efficient immobilization with bioconjugate solutions at low concentration, and to retain the peptides on the surfaces over extended periods.

It is known that if there are more than one pair of ligand-receptor interactions binding simultaneously, a synergistic augment rises in binding affinity with an order of magnitude enhancement over the corresponding monovalent ligand. This multivalent binding strategy has been used extensively in nature and with synthetic molecules to enhance their binding affinity. Dendrimers are ideal platforms to construct multivalent binding ligands due to their abundant functional groups in the periphery region. Studies have shown that the molecular structure of the multivalent ligands, including binding valency, the flexible linkage units, molecular architecture and receptor density all play significant roles in the ultimate association constant of the multivalent ligand with its receptor.

Osteogenic growth peptide (OGP) is an endogenous regulatory tetradecapeptide presents in mammalian serum with concentrations at the micromolar scale. Native or synthetic OGP regulates proliferation, alkaline phosphatase activity and matrix mineralization in studies of osteoblastic cell lines derived from human and other mammalian species. As its active portion, the carboxy-terminal pentapeptide, OGP(10-14) directs rat bone marrow mesenchymal stem cells to differentiate to osteoblasts. OGP or OGP(10-14)-functionalized biomaterials, including scaffolds for bone tissue engineering, gradient substrates, and peptide nanofibers, have been prepared, and shown to promote both cell proliferation and osteogenic differentiation, in vitro and in vivo.

What is needed in the art is a versatile molecule that will tether bioactive molecules to a variety of surfaces in such a way that their inherent biological function is preserved.

SUMMARY OF THE INVENTION

In various aspects, embodiments of the present invention are directed to a series of multivalent dendrons containing a bioactive peptide domain and surface-binding catechol domains. In some embodiments, these multivalent dendrons were obtained through solid phase synthesis and have a strong binding affinity to metal oxide surfaces such as, $TiO_2$, $ZrO_2$, $CeO_2$, $Fe_3O_4$, and $SiO_2$, as well as other inorganic surfaces such as hydroxyapatite, silver, fluorapatite, calcium carbonate and gold. These catechol-bearing dendrons provide a fast and efficient method to functionalize a wide range of inorganic materials with bioactive peptides and have the potential to be used in coating orthopaedic implants and fixation devices.

In various aspects, the present invention is directed to a multivalent dendron comprising a bioactive peptide domain and one or more surface-binding catechol domains. In some embodiments, the multivalent dendrons of the present invention further comprise a flexible linkage between said bioactive peptide domain and said one or more surface-binding catechol domains. In some embodiments, the multivalent dendron of the present invention may comprise any of the above-described embodiments wherein said bioactive peptide domain comprises a bioactive peptide selected from the group consisting of: —NH-KIPKASSVPTELSAISTLYL-COOH (SEQ ID No. 1), BMP-2, OGP, OGP C-terminal sequence (YGFGG) (SEQ ID No. 8), and combinations thereof.

In some embodiments, the multivalent dendron of the present invention may comprise any of the above-described embodiments wherein said bioactive peptide is less than 30 amino acids in length. In some embodiments, the multivalent dendron of the present invention may comprise any of the above-described embodiments wherein said bioactive peptide is less than 20 amino acids in length. In some embodiments, the multivalent dendron of the present invention may comprise any of the above-described embodiments wherein said bioactive peptide is OGP C-terminal sequence (YGFGG) (SEQ ID No. 8).

In some embodiments, the multivalent dendrons of the present invention may comprise any of the above-described embodiments wherein the multivalent dendron has a valence of from 1 to 8. In some embodiments, the multivalent dendrons of the present invention may comprise any of the above-described embodiments wherein the multivalent dendron has a valence of 1. In some embodiments, the multivalent dendrons of the present invention may comprise any of the above-described embodiments wherein the multivalent dendron has a valence of 2. In some embodiments, the multivalent dendrons of the present invention may comprise any of the above-described embodiments wherein the multivalent dendron has a valence of 4.

In some embodiments, the multivalent dendrons of the present invention may comprise any of the above-described embodiments wherein the flexible linkage comprises an oligomer of polyethylene glycol, polyethylene glycol, polypropylene glycol, or polyethylene. In some embodiments, the multivalent dendrons of the present invention may comprise any of the above-described embodiments wherein the flexible linkage comprises a polyethylene glycol oligomer having from 1 to 20 ethylene glycol units.

In some embodiments, the multivalent dendrons of the present invention may comprise any of the above-described embodiments having the formula:

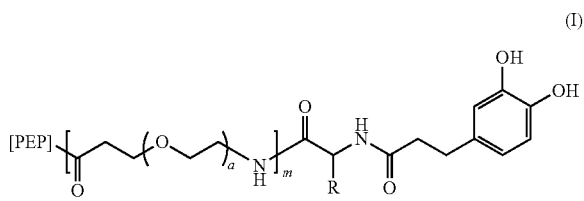

(I)

wherein PEP is a bioactive peptide; R is selected from the group consisting of —$CH_3$, —$(CH)_3NHC(NH_2)C=NH$, —$CH_2CONH_2$, —$CH_2COOH$, —$CH_2SH$, —$(CH_2)_2COOH$, —$(CH_2)_2CONH_2$, —$NH_2$, —$CH_2C=CH-N=CH-NH$, —$CH(CH_3)CH_2CH_3$, —$CH_2CH(CH_3)_2$, —$(CH_2)_4NH_2$, —$(CH_2)_2SCH_3$, —$CH_2Ph$, —$CH_2OH$, —$CH(OH)CH_3$, —$CH_2-C=CH-NH-Ph$, —$CH_2-Ph-OH$, —$CH(CH_3)_2$, and combinations thereof; a is an integer from 1 to 20; and m is 0 or 1.

In some embodiments, the multivalent dendrons of the present invention may comprise any of the above-described embodiments having the formula:

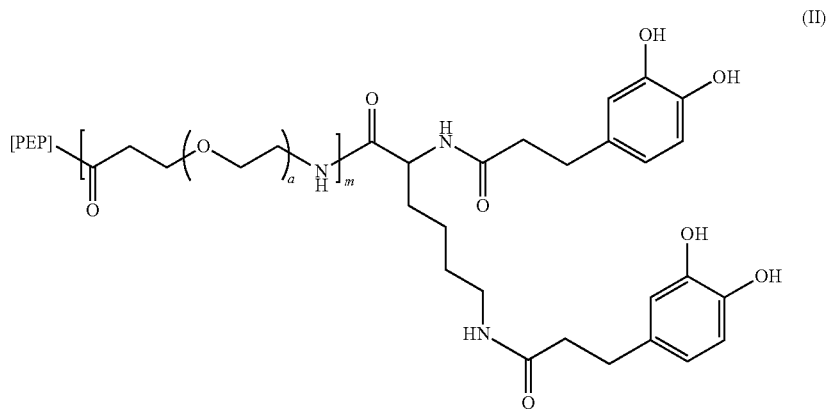

(II)

wherein PEP is a bioactive peptide; a is an integer from 1 to 20 and m is 0 or 1.

In some embodiments, the multivalent dendrons of the present invention may comprise any of the above-described embodiments having the formula:

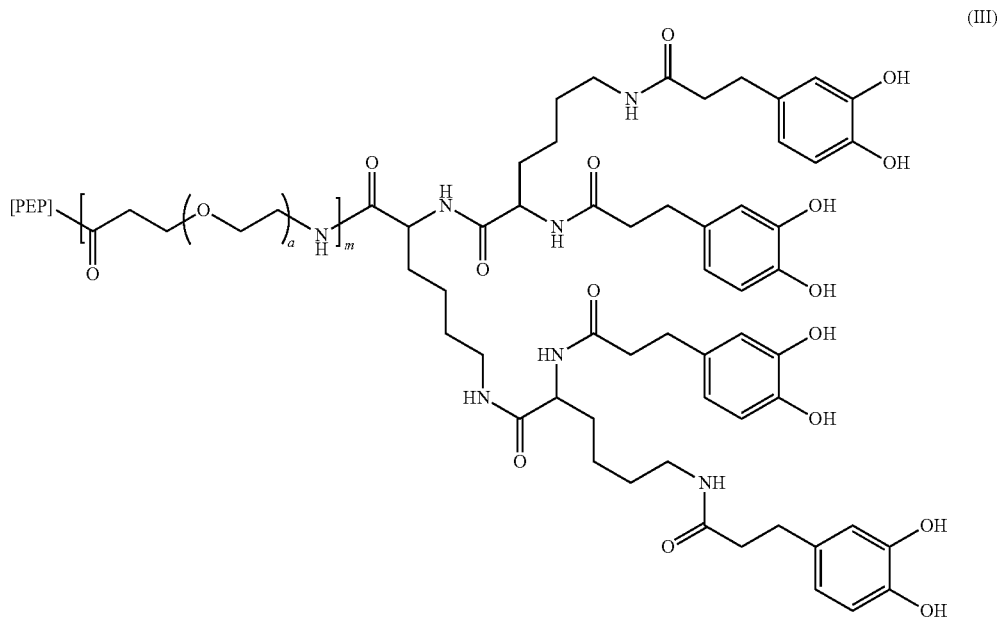

(III)

wherein PEP is a bioactive peptide; a is an integer from 1 to 20; and m is 0 or 1.

BRIEF DESCRIPTION OF THE DRAWINGS

For a more complete understanding of the features and advantages of the present invention, reference is now made to the detailed description of the invention along with the accompanying figures in which:

FIG. 9A is a survey scan of bare TiO$_2$ surface and OGP-(Cat)$_4$ immobilized TiO$_2$. The N1s signal comes from amide bonds in peptides. FIG. 9B is a graph showing the results of 1 minute of Ar$^+$ plasma treatment to the OGP-(Cat)$_4$ immobilized TiO$_2$ surface removed the adsorbed OGP-(Cat)$_4$ layer. The N1s peaks are normalized to the highest intensity (O1s) for comparison of the signal to noise ratio. FIGS. 9C and D graphs showing the signal changes in high resolution XPS spectra of O1s (FIG. 9C) and C1s (FIG. 9D) demonstrating the successful immobilization of OGP-(Cat)$_4$ on TiO$_2$ substrates. The multiple peaks in the high resolution XPS spectra of FIGS. 9C and D were fitted with a Gaussian model. The atomic ratios of C2/C1, C3/C1, O2/O1, O3/O1 and C3/N of respective surfaces were calculated based on the integrated area of each peak.

FIGS. 10A-B are images showing the immobilization of modular peptides as viewed by labeling the peptide with fluorescein. Due to multivalent binding effect, the retention time of OGP-(Cat)$_4$ on titanium oxide surface in buffer at physiological pH was longer than 2 weeks, which is long enough to trigger the cell responses. The immobilized FITC-labeled OGP-Cat on TiO$_2$ surface was observed under fluorescence microscope, and the mean intensity of fluorescence decreased after incubating the substrates in pH=7.4 25 mM HEPES buffer due to the diffusion of FITC-labeled OGP-Cat. TiO$_2$ substrates were incubated in the solution of 0.5 mM FITC-labeled OGP-Cat and FITC overnight, then thoroughly washed with water and dried with N$_2$. FITC-labeled OGP-Cat immobilized TiO$_2$ pattern on glass slides observed under (FIG. 10A) bright field microscope and (FIG. 10B) fluorescence microscope. The scale bar is 50 nm.

FIG. 11 is a graph of the mean intensity of a FITC-labeled OGP-Cat immobilized surface after incubation for different durations. The control sample is a TiO$_2$ substrate incubated in the solution of FITC for overnight. The mean intensity was calculated based on 10 randomly chosen sites observed under the same conditions.

FIG. 15A is a graph showing ALP activity of MC3T3 cells cultured on substrates having 99% OGP coverage (OGP-99%), substrates having 50% OGP coverage (OGP-50%), and TiO$_2$ substrates, respectively, on day 18. FIG. 15B is a graph showing mRNA levels of transcription factor gene of ALP, in MC3T3-E1 cells measured by real-time PCR after cell culture for 18 days. The ALP activity and its mRNA level of MC3T3 cells on OGP-99% substrate was significantly higher compared to substrates with lower concentration or none. FIG. 15C is a graph showing Ca$^{2+}$ accumulation in the cell films quantified with ICP-OES and normalized with total amount of protein. The cell films on OGP-99% exhibited 2-fold higher content of Ca$^{2+}$ compared with those on other substrates. The error bar was calculated from three replicates.

DETAILED DESCRIPTION OF THE ILLUSTRATIVE EMBODIMENTS

Figure 1A:
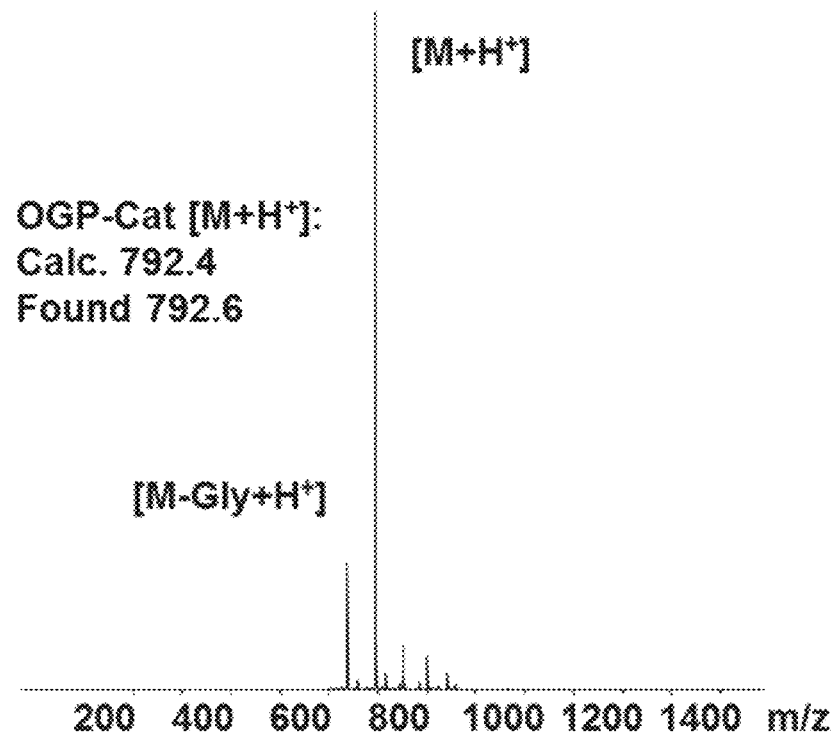
FIGS. 1A-F are electrospray ionization (ESI) of OGP-(Cat)$_n$ (FIGS. 1A-C) and OGP-PEG-(Cat)$_n$ (FIGS. 1D-F) (n=1, 2, 4).
Figure 1B:
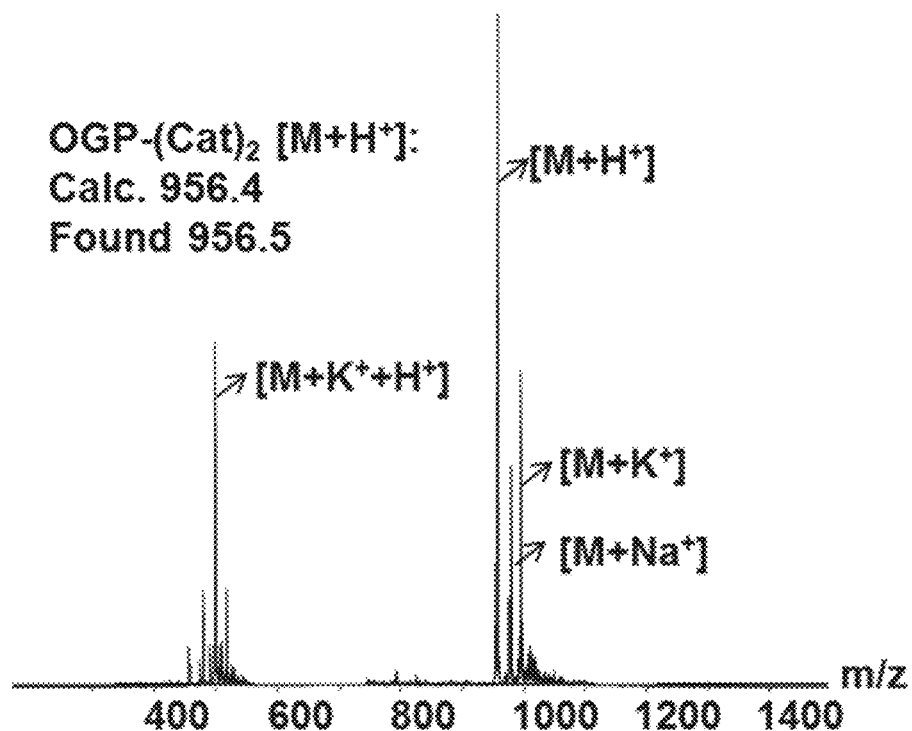
Figure 1C:
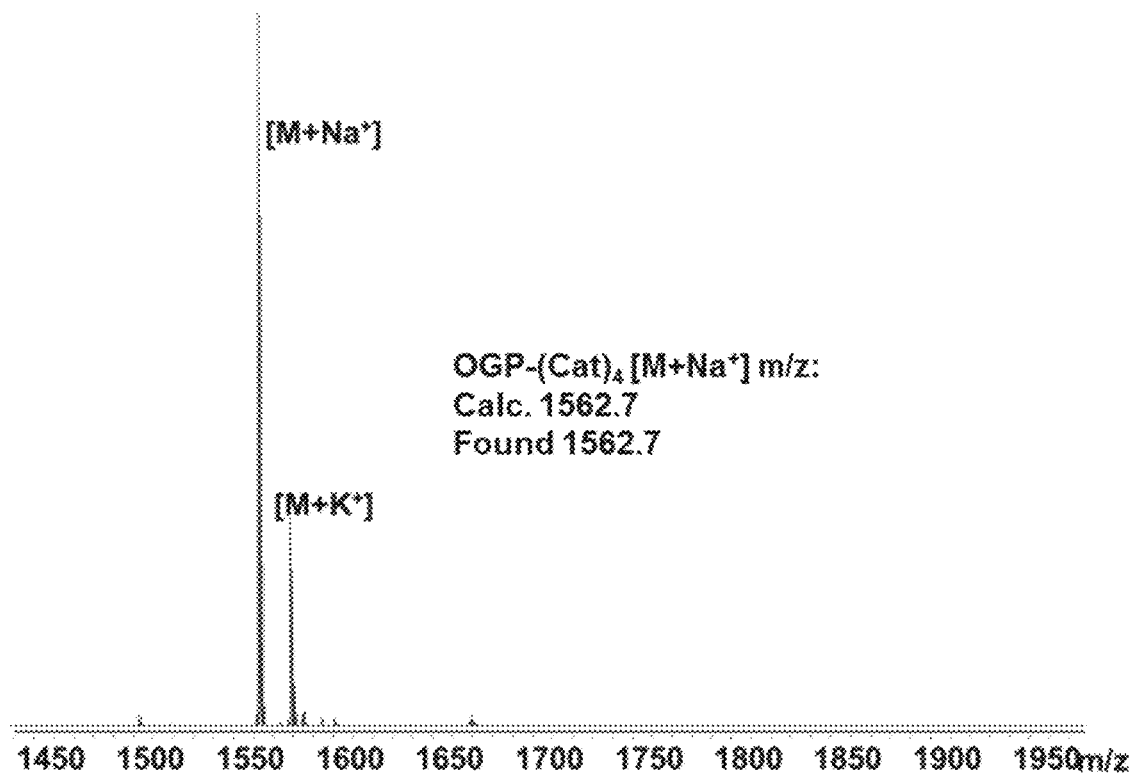
Figure 1D:
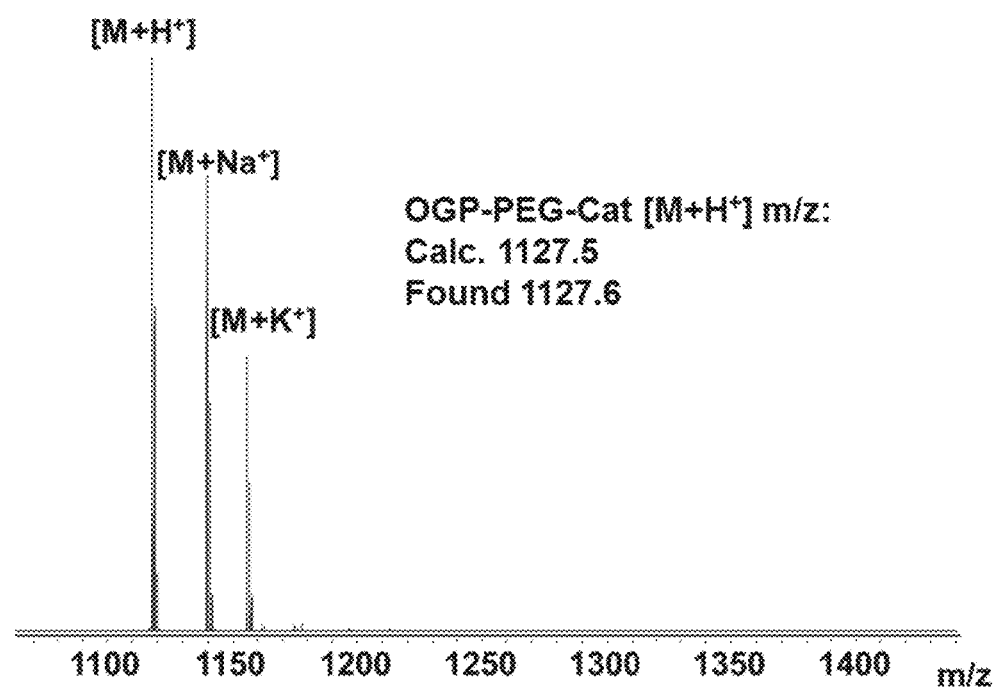
Figure 1E:
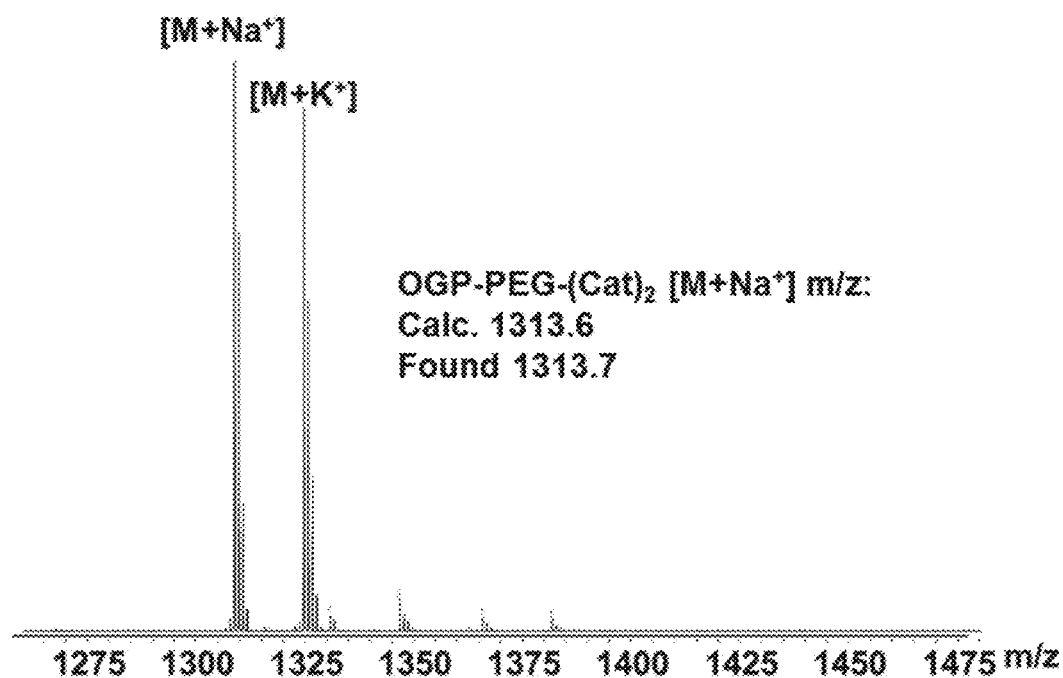
Figure 1F:
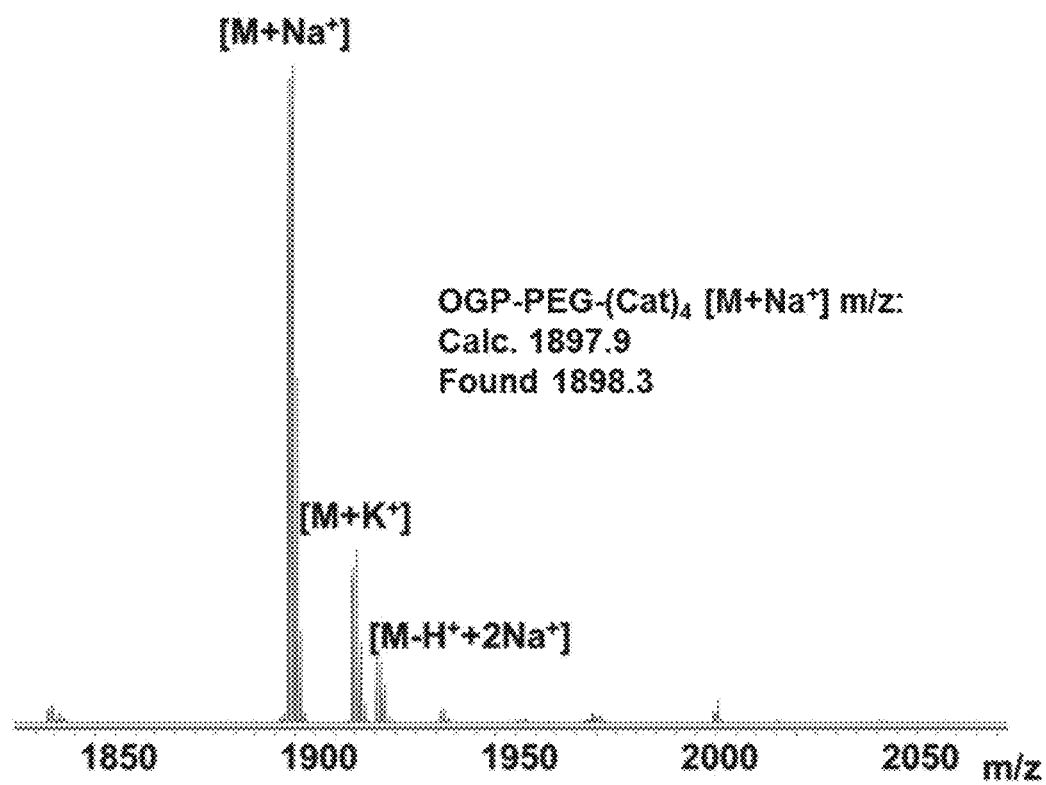

In general outline, the various embodiments of the present invention relate to an amino acid based multivalent binding dendron having a bioactive peptide at its focal point and one or more surface-binding catechol domains. These multivalent dendrons are useful for binding bioactive peptides to metal oxide and other surfaces. In one or more embodiments, the multivalent amino acid-based dendrons of the present invention will have a bioactive peptide domain located at its focal point and one or more surface-binding catechol domains at its periphery. As the amino acid based multivalent binding dendron of one or more embodiments of the present invention may bond to metal oxide and other surfaces by coordination bonding, the terms "ligand," "catechol-bearing multivalent binding ligands," "catechol bearing ligand," "multivalent ligand," "tetravalent ligand," may also be used herein to refer to these compounds.

The bioactive peptide domain of the multivalent surface-binding dendrons of the present invention will contain a bioactive peptide that may be connected to the focal point of the dendron either directly, or through a flexible linkage. As used herein, a "bioactive peptide" refers to any peptide sequence having 30 amino acids or less with a specific biological function, and is not particularly limited. Any bioactive peptide having 30 amino acids or less may be used.

In some embodiments, the bioactive peptide may be an osteoinductive, osteoconductive, antimicrobial, morphogenic, homing or immunostimulatory peptide. Suitable bioactive peptides may include, without limitation, —NH-KIPKASSVPTELSAISTLYL-COOH (SEQ. ID No. 1), bone morphogenetic protein 2 (BMP-2), osteoconductive peptide (OGP), OGP C-terminal sequence (YGFGG) (SEQ. ID No. 8), GRGDS (SEQ. ID No. 9), and combinations thereof. In some embodiments, the bioactive peptide may be OGP C-terminal sequence (YGFGG) (SEQ. ID No. 8). In some embodiments, the bioactive peptide may be OGP.

In some embodiments, the bioactive peptide may be less than 20 amino acids in length. In some embodiments, the bioactive peptide may be from 2 to 22 amino acids in length. In some embodiments, the bioactive peptide may be from 2 to 20 amino acids in length. In some embodiments, the bioactive peptide may be from 2 to 15 amino acids in length. In some embodiments, the bioactive peptide may be from 2 to 10 amino acids in length. In some embodiments, the bioactive peptide may be from 10 to 20 amino acids in length. In some embodiments, the bioactive peptide may be from 2 to 5 amino acids in length.

As set forth above, the multivalent dendrons of the present invention comprise one or more surface-binding catechol domains. As should be apparent, each one of these surface-binding catechol domains will have a catechol functional group. These catechol groups are known to form bonds with metal oxide surfaces such as, $TiO_2$, $ZrO_2$, $CeO_2$, and $Fe_3O_4$, $SiO_2$, as well as other inorganic surfaces such as hydroxyapatite, silver, fluorapatite, calcium carbonate and gold.

As will be appreciated by those of skill in the art, the number of surface-binding catechol domains is a function of the valence of the dendron. As used herein, the "valence" of a dendron refers to the number of catechol units that are present on the molecule. A dendron having a valence or 4, for example, will have four catechol units. In some embodiments, the multivalent dendrons of the present invention may have a valence as high as 16, but valences of from 1 to 8 are preferred. In some embodiments, the multivalent dendrons of the present invention may have a valence of from 2 to 8. In some embodiments, the multivalent dendrons of the present invention may have a valence of from 4 to 8. In some embodiments, the multivalent dendrons of the present invention may have a valence of from 1 to 6. In some embodiments, the multivalent dendrons of the present invention may have a valence of from 1 to 4. In some embodiments, the multivalent dendrons of the present invention may have a valence of 2. In some embodiments, the multivalent dendrons of the present invention may have a valence of 4.

The multivalent dendrons of the present invention are amino acid-based and the dendron body (the portion of the dendron the between the bioactive peptide or flexible linkage and the catechol domains) comprises one or more amino acids. In embodiments where the valence is 1 and there is a single catechol domain, the dendron body may comprise the residue of any α-amino acid other than proline. As used herein, the term "residue(s)" is used to refer generally to the part of a monomer or other chemical unit that has been incorporated into a polymer or large molecule. By extension, the terms "residue of an amino acid" and "amino acid residue" are used interchangeably to refer to part of the amino acids that is incorporated into a larger molecule such as a peptide or the multivalent surface-binding dendrons of the present invention. In some of these embodiments, the dendron body may comprise the residue of alanine (ala—A), arginine (arg—R), asparagine (asn—N), aspartic acid (asp—D), cysteine (cys—C), glutamine (gln—Q), glutamic acid (glu—E), glycine (gly—G), histidine (his—H), isoleucine (ile—I), leucine (leu—L), lysine (lys—K), methionine (met—M), phenylalanine (phe—F), serine (ser—S), threonine (thr—T), tryptophan (trp—W), tyrosine (tyr—Y), or valine (val—V). or any combination thereof In some embodiments, the multivalent dendron of the present invention may have the formula:

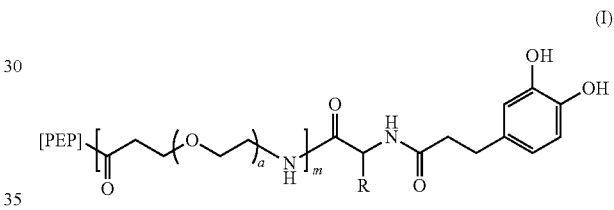

(I)

wherein PEP is a bioactive peptide; R is —CH$_3$, —(CH$_2$)$_3$NHC(NH$_2$)C=NH, —CH$_2$CONH$_2$, —CH$_2$COOH, —CH$_2$SH, —(CH$_2$)$_2$COOH, —(CH$_2$)$_2$CONH$_2$, —NH$_2$, —CH$_2$C=CH—N=CH—NH, —CH(CH$_3$)CH$_2$CH$_3$, —CH$_2$CH(CH$_3$)$_2$, —(CH$_2$)$_4$NH$_2$, —(CH$_2$)$_2$SCH$_3$, —CH$_2$Ph, —CH$_2$OH, —CH(OH)CH$_3$, —CH$_2$—C=CH—NH-Ph, —CH$_2$-Ph-OH, or —CH(CH$_3$)$_2$; a is an integer from 1 to 20; and m is 0 or 1.

In embodiments where the valence is two or more, the dendron body will comprise one or more lysine residues. As will be apparent to those of ordinary skill in the art, the amino acid lysine presents two amine groups for binding. In some embodiments, both of these amine groups may be functionalized with catechol groups to produce a multivalent dendron having two surface-binding catechol domains (valence=2).

In some embodiments, the catechol functional groups are separated from the dendron body by from 2 to 10 carbon atoms. In some embodiments, the catechol functional groups are separated from the dendron body by from 4 to 10 carbon atoms. In some embodiments, the catechol functional groups are separated from the dendron body by from 6 to 10 carbon atoms. In some embodiments, the catechol functional groups are separated from the dendron body by from 8 to 10 carbon atoms. In some embodiments, the catechol functional groups are separated from the dendron body by from 2 to 4 carbon atoms. In some embodiments, the catechol functional groups are separated from the dendron body by from 2 to 6 carbon atoms. In some embodiments, the catechol functional groups are separated from the dendron body by from 2 to 8 carbon atoms.

In some embodiments, the multivalent dendron of the present invention may have the formula:

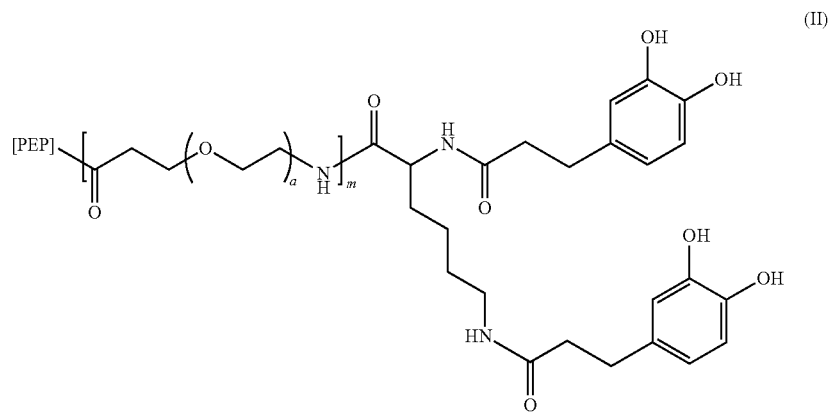

(II)

wherein PEP is a bioactive peptide; a is an integer from 1 to 20; and m is 0 or 1.

In some other embodiments, one of the two amine groups on these forming dendrons may be reacted with one additional lysine molecule to form a dendron body having 3 amino groups available for bonding. In some other embodiments, both of the amine groups on these forming dendrons may be reacted with an additional lysine molecules to form a dendron body having 4 amino groups available for bonding. As should be apparent to those of skill in the art, each time these dendrons are reacted with an excess of lysine molecules the number of amino groups available for bonding will double. In this way, the valence of the surface-binding dendrons of the present invention may be controlled. These dendrons are then functionalized with catechol groups to form multivalent dendrons having a number of surface-binding catechol domains that corresponds to the number of amino groups available for bonding, as will be discussed in more detail below.

In some embodiments, the multivalent dendrons of the present invention may have the formula:

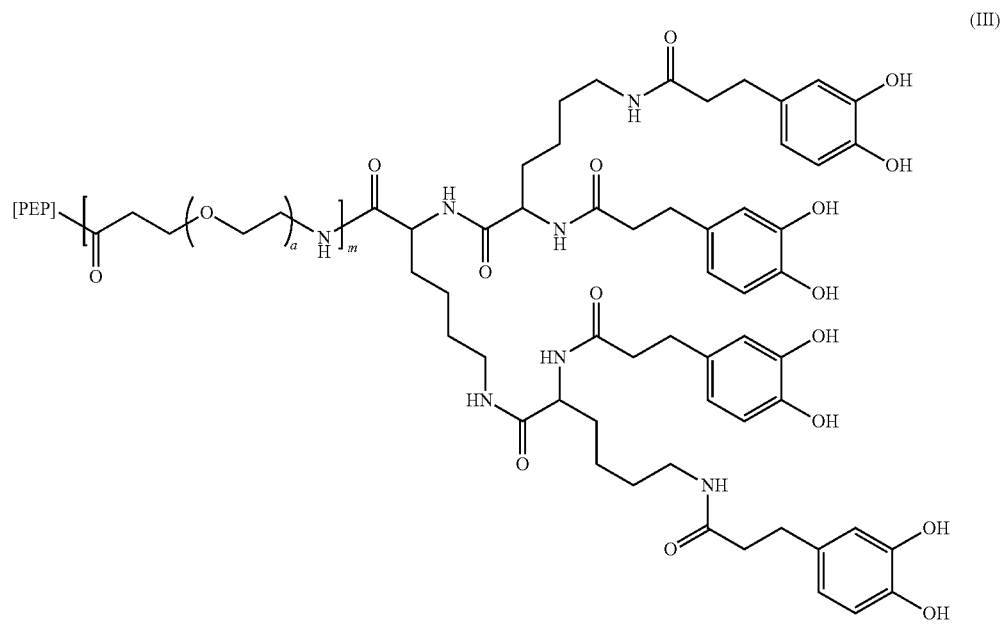

(III)

wherein PEP is a bioactive peptide; a is an integer from 1 to 20; and m is 0 or 1. In this way, it is possible to form a multivalent dendron having a desired number of surface-binding catechol domains.

As set forth above, the bioactive peptide in these embodiments may be attached directly, or indirectly through a flexible linkage, to the C-terminus of the amino acid at the focal point of the dendron. The flexible linkage may be formed from any flexible material capable of bonding to the N-terminal end of a bioactive peptide and the C-terminal end of the amino acid at the focal point of the dendron. In some embodiments, the flexible linkage may comprise an oligomer of polyethylene glycol, polypropylene glycol, or polyethylene. In some embodiments, flexible linkage comprises a polyethylene glycol oligomer having from 1 to 20 polyethylene glycol units. In some embodiments, the flexible linkages may comprise a hexaethylene glycol oligomer.

With reference to formulas (I), (II), and (III), above, "m" corresponds to the presence or absence of the flexible linkage. If m=1, there is a flexible linkage. If m=0, there is no flexible linkage and the bioactive peptide will be bonded directly to the focal point of the dendron. Similarly, in the embodiments show in formulas I, II, and III, "a" represents the length of the flexible linkage measured in terms of the number of repeating polyethylene glycol units in the flexible linkage when m=1. Once again, while the flexible linker shown in formulas (I), (II), and (III) is comprised of repeating polyethylene glycol units, the invention is to be so limited. In some embodiments, the flexible linker may be comprised of repeating units of polypropylene glycol, polyethylene glycol or polyethylene. In some embodiments, a may be an integer from 2 to 20. In some embodiments, a may be an integer from 4 to 20. In some embodiments, a may be an integer from 6 to 20. In some embodiments, a may be an integer from 8 to 20. In some embodiments, a may be an integer from 10 to 20. In some embodiments, a may be an integer from 1 to 18. In some embodiments, a may be an integer from 1 to 16. In some embodiments, a may be an integer from 1 to 14. In some embodiments, a may be an integer from 1 to 12. In some embodiments, a may be an integer from 1 to 10. In some embodiments, a may be an integer from 1 to 8. In some embodiments, a may be an integer from 1 to 5. In some embodiments, a may be an integer from 3 to 8. In some embodiments, a may be 6.

In some embodiments, the multivalent dendron of the present invention may have the formula:

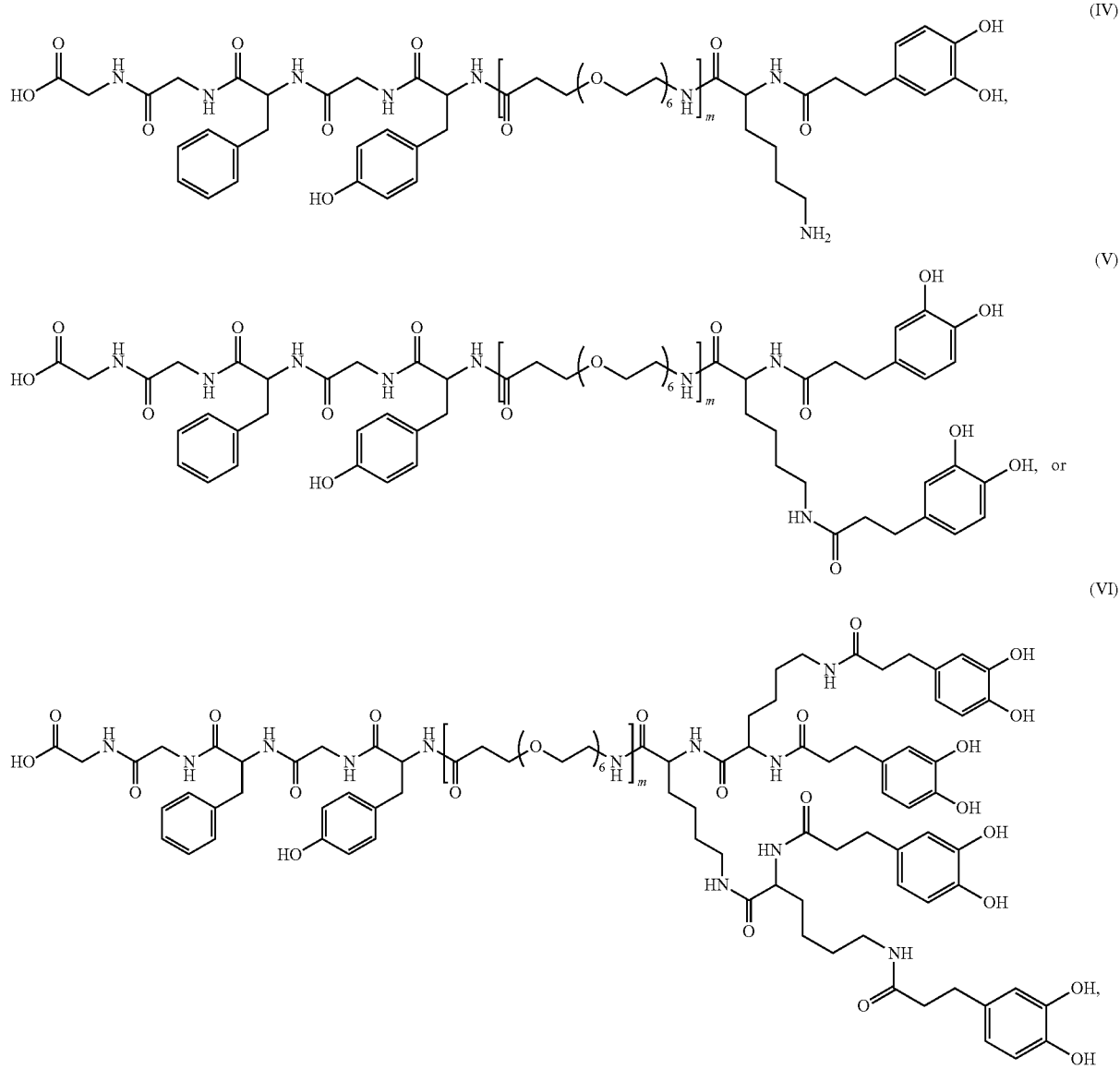

wherein m is 0 or 1 as set forth above.

The multivalent dendrons of the present invention may be formed using any methods known in the art. In some embodiments, dendrons of the present invention may be formed using simple solid phase protein synthesis techniques as shown in Scheme 1 below.

embodiments, the phase peptide synthesizer may be a Liberty 1 peptide microwave synthesizer (CEM Corporation,

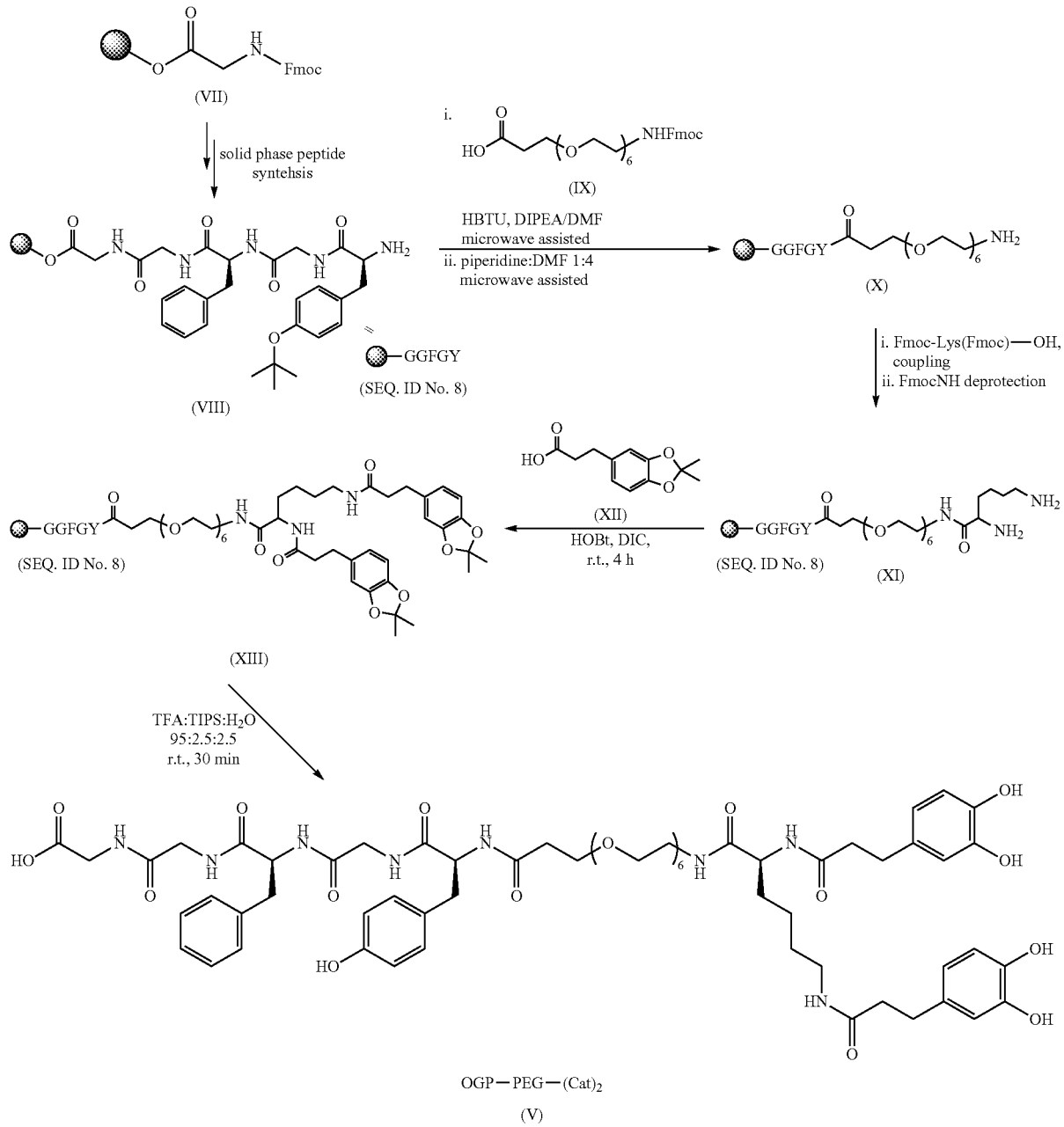

Scheme 1

In these embodiments, the bioactive peptide is first synthesized on a solid phase polymer resin by conventional solid phase peptide synthesis methods. These methods are well known in the art and need not be described in detail. In the reaction shown in Scheme 1, an OGP(10-14) peptide is formed by solid phase peptide synthesis from a Fmoc protected glycine connected at its C-terminus to a solid phase resin VII. In some of these embodiments, solid phase peptide synthesis may be accomplished using any conventional solid phase CEM Discovery Microwave peptide synthesizer with microwave assistance functionality. In some Matthews, N.C.). In these methods, amino acids are sequentially added to the N-terminus of a forming peptide chain through a series of deprotection and coupling steps by FMOC chemistry. In some other embodiments, the bioactive peptide may be may be synthesized by any other suitable peptide synthesizer or by hand using FMOC chemistry. And while the bioactive peptide shown in Scheme 1 is OGP(10-14), it should be understood that any of the bioactive peptides described above may also be formed in this manner and used in Scheme 1.

Once the desired peptide has been formed, it is bonded either to a flexible linkage or directly to the dendron body.

Again, it should be understood that the invention is not to be limited to the flexible linkage shown in Scheme 1, and any of the materials described above with respect to the flexible linkage could also have been used in place of the hexaethylene glycol shown in Scheme 1, or if no flexible linkage is desired (m=0), this step may be omitted altogether. In the embodiment shown in Scheme 1, the C-terminal end of the bioactive peptide is left attached to and protected by the a solid phase resin and the N-terminal end of the peptide is reacted with an Fmoc protected polyethylene glycol (PEG) IX having six ethylene glycol units (a=6), thereby adding the PEG to the N-terminal end of the bioactive peptide to form the PEG-PEP molecule X.

Addition of the flexible linkage to the bioactive peptide may be accomplished by any suitable means. In the embodiment shown in Scheme 1, addition of the flexible linkage IX to the peptide VII is accomplished by (i) a microwave assisted reaction with a coupling agent and a base in a suitable solvent and (ii) a microwave assisted reaction with a base in a suitable solvent. One of ordinary skill in the art will be able to select a suitable coupling agent, base, amino acid and the necessary solvents without undue experimentation. Suitable coupling agents may include, without limitation, 2-(1H-benzotriazol-1-yl)-1,1,3,3-tetramethyluronium hexafluorophosphate (HBTU), (benzotriazol-1-yloxy) tris(dimethylamino)phosphonium hexafluorophosphate (BOP), bis-(2-oxo-3-oxazolidinyl)phosphinic chloride (BOP-Cl), (1-cyano-2-ethoxy-2-oxoethylidenaminooxy)dimethylamino-morpholino-carbenium hexafluorophosphate (COMU™), dicyclohexylcarbodiimide (DCC), diisopropylcarbodiimide (DIC), 3-(diethoxyphosphoryloxy)-1,2,3-benzotriazin-4(3H)-one (DEPBT), N-(3-dimethylaminopropyl)-N'-ethylcarbodiimide hydrochloride (EDC), 2-(1H-7-azabenzotriazol-1-yl)-1,1,3,3-tetramethyl uronium hexafluorophosphate (HATU), O-benzotriazole-N,N,N',N'-tetramethyl-uronium-hexafluoro-phosphate (HBTU), 2-(6-Chloro-1H-benzotriazole-1-yl)-1,1,3,3-tetramethylaminium hexafluorophosphate (HCTU), (7-azabenzotriazol-1-yloxy) tripyrrolidinophosphonium hexafluorophosphate (PyAOP), (benzotriazol-1-yloxy)tripyrrolidinophosphonium hexafluorophosphate (PyBOP), bromotripyrrolidinophosphonium hexafluorophosphate (PyBrOP), O-(7-azabenzotriazole-1-yl)-N,N,N',N'-tetramethyluronium tetrafluoroborate (TATU), O-(benzotriazol-1-yl)-N,N,N',N'-tetramethyluronium tetrafluoroborate (TBTU), N,N,N',N'-tetramethyl-O-(3,4-dihydro-4-oxo-1,2,3-benzotriazin-3-yl) uranium tetrafluoroborate (TDBTU), 2-(5-norborene-2,3-dicarboximido)-1,1,3,3-tetramethyluronium tetrafluoroborate (TNTU), O-[(ethoxycarbonyl) cyanomethylenamino]-N,N,N',N'-tetra methyluronium tetrafluoroborate (TOTU), 2-(2-pyridon-1-yl)-1,1,3,3-tetramethyluronium tetrafluoroborate (TPTU), or N,N,N'N'-tetramethyl-O—(N-succinimidyl)uronium tetrafluoroborate (TSTU).

In the embodiment shown in Scheme 1 above, the coupling agent is HBTU. Suitable bases may include, without limitation, N,N-Diisopropylethylamine (DIPEA or Hünig's base). In the embodiment shown in Scheme 1 above, the base is DIPEA. Suitable base may include, without limitation, piperidine, or morpholine. In the embodiment shown in Scheme 1 above, the base is piperidine. Suitable solvents for the coupling agent and base may include, without limitation, N,N dimethylformamide (DMF), N-methyl pyrolidone (NMP) and combinations thereof. Suitable solvents for the coupling reaction may include, without limitation, DMF and/or NMP.

Next, the peptide (m=0) or peptide-PEG complex (m=1) may be reacted with an amino acid that will form the focal point of the dendron body. In the embodiment shown in Scheme 1, the amino acid is lysine, but it should be understood that if only a single surface-binding catechol domain is desired, any α-amino acid other than proline may be used. In the embodiment of Scheme 1, the lysine is added to the amine end group of the PEG by an amidation reaction. The resulting molecule will have one (if an amino acid other than lysine was used) or two (if lysine was used) amine functional groups.

Next, the amine functional groups on the dendron are functionalized with a protected catechol group. In some embodiments, the protected catechol groups may be added to the amine functional group or groups on the dendron by reacting it with a protected carboxy functionalized catechol compound. In these embodiments, the catechol functional group is attached to the amino acid chain at the N-terminal end by means of an amide bond between the amine group and a carboxyl group connected to the catechol functional group.

In some of these embodiments, the carboxyl functional group may be separated from the catechol group by from 1 to 20 carbon atoms. In some of these embodiments, the carboxyl functional group may be separated from the catechol group by from 2 to 15 carbon atoms. In some of these embodiments, the carboxyl functional group may be separated from the catechol group by from 2 to 10 carbon atoms. In some of these embodiments, the carboxyl functional group may be separated from the catechol group by from 2 to 6 carbon atoms. In some of these embodiments, the carboxyl functional group may be separated from the catechol group by from 2 to 4 carbon atoms. In some of these embodiments, the carboxyl functional group may be separated from the catechol group by from 5 to 10 carbon atoms. In some of these embodiments, the carboxyl functional group may be separated from the catechol group by from 5 to 20 carbon atoms. In some of these embodiments, the carboxyl functional group may be separated from the catechol group by from 10 to 20 carbon atoms. In some of these embodiments, the carboxyl functional group may be separated from the catechol group by 2 carbon atoms.

In some embodiments, the catechol compound may be the deamino form of the naturally occurring 3,4-dihydroxyphenylalanine (DOPA). In some embodiments, the catechol compound may be 3,4-dihydroxyhydrocinnamic acid and is commercially available from Sigma Aldrich Company LLC (St. Louis, Mo.) or Alfa Aesar (Ward Hill, Mass.).

The catechol groups of the protected catechol compounds may be protected in any manner known in the art for that purpose provided that removal of the protecting group does not cause degradation of the parent compound. In some embodiments, acetonide protection mechanisms known in the art may be utilized to protect the catechol groups. In some embodiments, these carboxyl functionalized acetonide protected catechol compounds may have the formula:

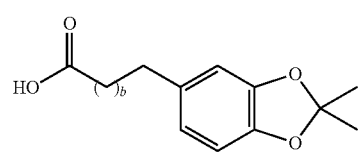

(XII)

wherein b is an integer from about 0 to about 20. In some embodiments b may be an integer from about 0 to 15. In some embodiments b may be an integer from about 0 to 10.

In some embodiments b may be an integer from about 0 to 6. In some embodiments b may be an integer from about 1 to 4. In some embodiments b may be an integer from about 2 to 20. In some embodiments b may be an integer from about 6 to 20. In some embodiments b may be an integer from about 10 to 20. In some embodiments b may be an integer from about 15 to 20. In some embodiments b may be an integer from about 3 to 6. In some embodiments b may be an integer from about 2 to 5. In some embodiments b may be an integer from about 2 to 4. In some embodiments b may be 1. In some embodiments, the carboxyl functionalized protected catechol compound may comprise 2,2-dimethyl-1,3-benzodioxole-5-propanoic acid, 2,2-dimethyl-1,3-benzodioxole-5-butanoic acid, 2,2-dimethyl-1,3-benzodioxole-5-pentanoic acid, 2,2-dimethyl-1,3-benzodioxole-5-hexanoic acid, 2,2-dimethyl-1,3-benzodioxole-5-heptanoic acid, or 2,2-dimethyl-1,3-benzodioxole-5-octanoic acid.

In some embodiments, the carboxyl functionalized protected catechol compounds may be prepared from the corresponding carboxyl functionalized catechol compound by reaction with acetone under basic conditions. In some embodiments, the carboxyl functionalized protected catechol compounds may be prepared as described in Example 4, below.

In the embodiment shown in Scheme 1, the protected catechol groups were added to the two amine groups of the lysine by the formation of an amine bond between the carboxyl functionalized end group of an acetonide-protected 3,4-dihydroxyhydrocinnamic acid XII with amine groups of the lysine using an additive such as hydroxybenzotriazole (HOBt) and a peptide coupling reagent such as N,N'-diisopropylcarbodiimide (DIC). It should be noted that in these embodiments, the step of coupling of acetonide-protected 3,4-dihydroxyhydrocinnamic acids XII with amines in the peptide chain terminus cannot tolerate microwave-assisted conditions, and the protection of catechol groups is essential for successful synthesis.

One of ordinary skill in the art will be able to select a suitable additive and coupling agent without undue experimentation. Suitable additives may include, without limitation, HOBt, 1-hydroxybenzotriazole hydrate (HOBt H2O), 1-hydroxy-7-azabenzotriazole (HOAt), 1-hydrox-6-chlorotriazole (6-Cl-HOBt), 3-hydroxy, 1,2,3-benzotriazin-4(3H)-one (HOOBt), N-hydroxysuccinimide (HOSu), and combinations thereof. In the embodiment shown in Scheme 1 above, the additive is HOBt. One of ordinary skill in the art will likewise be able to select a suitable coupling agent without undue experimentation. Suitable peptide coupling reagent may include, without limitation, HBTU, BOP, COMF™, DCC, DIC, DEPBT, EDC, HATU, HBTU, HCTU, PyAOP, PyBOP, PyBrOP, TATU, TBTU, TDBTU, TNTU, TOTU, TPTU, TSTU, and combinations thereof. In the embodiment shown in Scheme 1 above, the coupling agent is DIC.

The protected catechol group on the resulting dendron is then deprotected, before being cleaved from the resin to form the multivalent dendron of one or more embodiments of the present invention. The method selected for deprotecting the catechol functionalized groups will, of course, depend upon the way in which the catechol group has been protected. In some embodiments, like that shown in Scheme 1 above, an acetonide protected catechol compound may be used and methods for deprotecting such compounds are well known in the art. In these embodiments, the catechol groups on the dendron may be deprotected by reacting them with an aqueous solution containing a strong acid such as triflouroacetic acid (TFA) and a proton scavenger such as triisopropylsilyl (TIPS) to obtain free catechol groups. Again, these methods are well known in the art and one of ordinary skill in the art will be able to select a suitable acid and proton scavenger without undue experimentation. In the embodiment shown in Scheme 1 above, the acid is TFA. One of ordinary skill in the art will likewise be able to select a suitable proton scavenger without undue experimentation. In some embodiments, the acetonide protected catechol groups may be deprotected as described in Example 5.

The multivalent dendrons of various embodiments of the present invention may be attached to metal oxide surfaces such as, $TiO_2$, $ZrO_2$, $CeO_2$, and $Fe_3O_4$, $SiO_2$, as well as other inorganic surfaces such as hydroxyapatite, silver, fluorapatite, calcium carbonate and gold by any suitable method. In some embodiments, the multivalent dendrons may be dissolved in a suitable aqueous or organic solvent and then contacted to the substrate surface in any convenient manner. In some embodiments, the surface may subsequently be rinsed with a buffered solution to remove any unattached dendrons.

Accordingly, through a straightforward synthesis, a series of multivalent catechol-bearing modular peptides may be generated to providing a simple and efficient method of functionalizing metal-oxide based orthopaedic implants with bioactive peptides. As will be described in detail below, with a multivalent binding strategy, tetravalent dendrons according to embodiments of the present invention were shown to persist on the metal oxide surfaces in vitro beyond two weeks under near physiological conditions. The bioactivity of immobilized peptides was demonstrated in an in vitro cell culture study and it was found that the tethered OGP(10-14) promoted the proliferation, osteogenic differentiation and mineralization of MC3T3-E1 cells. Considering their strong adhesion to versatile metal oxide surfaces, it is believed that the multivalent dendrons of various embodiments of the present invention represent a substantial improvement over prior art systems and a large step toward the development of translational implants with improved bioactivity.

Experimental

In order to evaluate the functionality of multivalent dendrons according to various embodiments of the present invention, lysine-based dendrons were used as the platform to construct the catechol-bearing multivalent binding ligands with a bioactive peptide at the core as shown in Formulas I, II, and III, above. In the periphery of these dendrons, tunable numbers of catechol (Cat) functional groups were attached with a valence of 1, 2 or 4. In the focal point of the dendron, an osteoconductive peptide, OGP(10-14) (SEQ. ID No. 8), with the amino acid sequence YGFGG (SEQ. ID No. 8) was linked. (See PEP in Formulas I, II, and III). The two domains were connected with (m=1) or without (m=0) a hexaethylene glycol flexible linkage (a=6) (See Formulas IV, V, and VI). The embodiments without the hexaethylene glycol flexible linkage are generally referred to herein as OGP-(Cat)$_n$ and the embodiments with the hexaethylene glycol flexible linkage are generally referred to herein as OGP-PEG-(Cat)$_n$, wherein n is 1, 2, or 4.

The synthesis of OGP-(Cat)$_n$ and OGP-PEG-(Cat)$_n$ (n=1, 2, 4.) were carried out using Fmoc based solid phase synthesis as described above, and in particular, OGP-PEG-(Cat)$_2$ was synthesized as shown in Scheme 1 as an example. (See, Examples 1-5) As set forth above, the last coupling step of acetonide-protected 3,4-dihydroxyhydrocinnamic acids XII with amines in the peptide chain terminus cannot tolerate microwave-assisted conditions, and the protection of catechol groups is essential for successful synthesis. No intervening purification was required, and synthetic process only took 6 hours in all. After Reversed Phase High Performance Liquid Chromatography (RP-HPLC) purification, the OGP(10-14) peptide-functionalized catechol-bearing dendrons were achieved with high purity with the yield of 9%-25% as shown in electrospray ionization (ESI) or matrix-assisted laser desorption/ionization time-of-flight (MALDI-ToF) mass spectrometry (FIG. 1).

Adsorption to TIO₂ Measured by QCM-d

Figure 2:
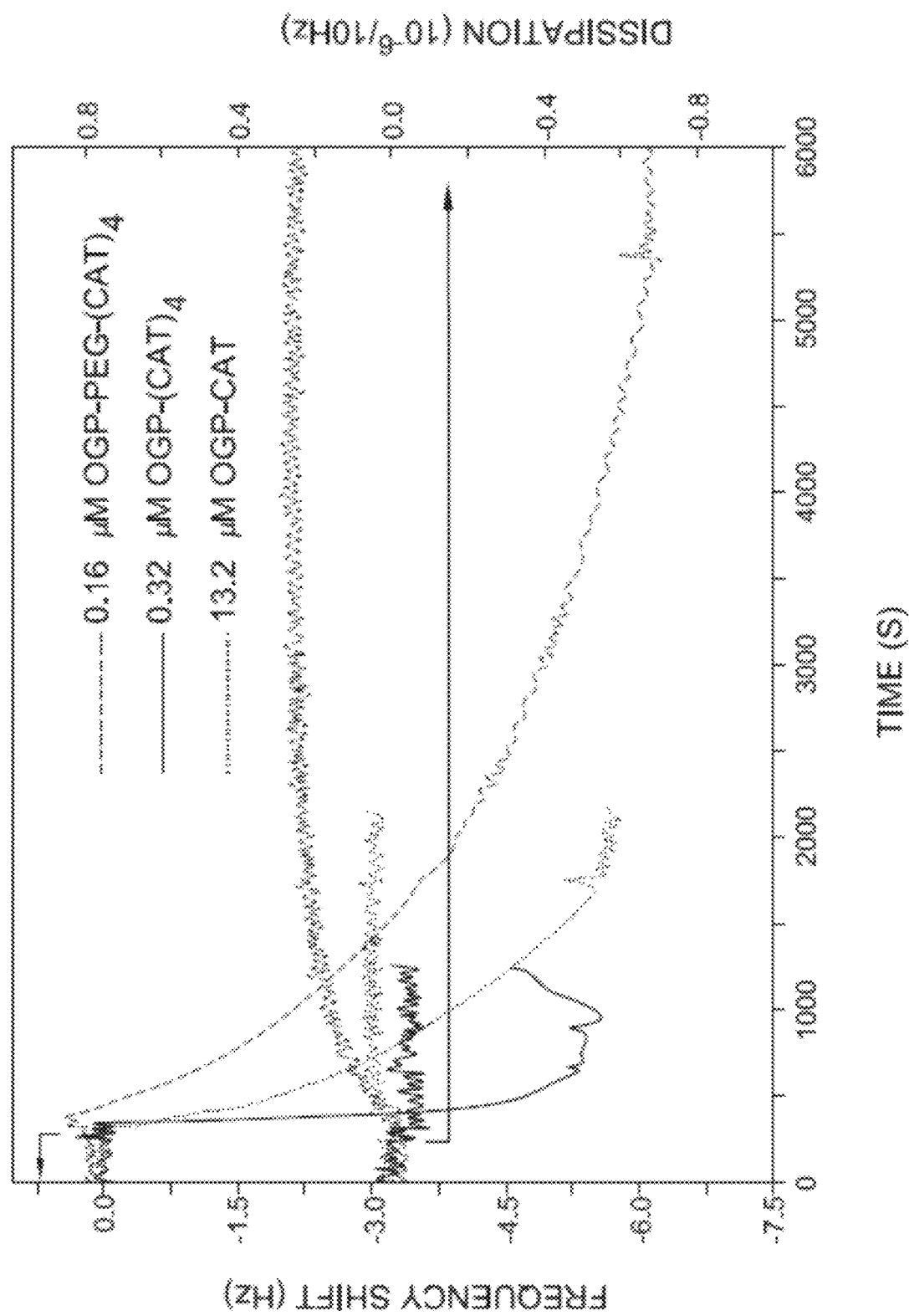
FIG. 2 is a graph showing the adsorption of catechol-functionalized dendrons, OGP-Cat, OGP-(Cat)$_4$ and OGP-PEG-(Cat)$_4$ onto TiO$_2$ surfaces generated by quartz crystal microbalance with dissipation (QCM-d). The experiment contained three processes: i) baseline in HEPES buffer; ii) adsorption of ligands; iii) buffer washing the adsorbed ligands, as indicated by the small peak due to the stop of flow. To reach similar level of frequency shift, tetravalent ligands OGP-(Cat)$_4$ and OGP-PEG-(Cat)$_4$ requires solution at much lower concentration compared to monovalent ligand, OGP-Cat, indicating a stronger binding affinity.

The adsorption processes of all molecules to $TiO_2$ surfaces at 25° C. and pH 7.4 were monitored by quartz crystal microbalance with dissipation (QCM-d). (See Example 7). Multivalent binding effects that enhanced the binding affinity were clear. In FIG. 2, to obtain a similar level of adsorption, ~6 Hz frequency shift, the concentration of monovalent ligand, OGP-Cat, was 13 μM, while that of tetravalent ligand, OGP-(Cat)₄ and OGP-PEG-(Cat)₄, was 0.32 and 0.16 μM, respectively due to the mass differences. A much smaller amount of sample (~80-fold less) was needed for the tetravalent ligand OGP-PEG-(Cat)₄ compared with the monovalent ligand OGP-Cat to achieve the same level (mass) of surface adsorption. Moreover, it was found that the tetravalent ligands remained on the $TiO_2$ surface under buffer washing, as no frequency shift was observed after switching the solution to HEPES buffer. This indicates that the tetravalent ligands are sequestered on the $TiO_2$ surface and are unlikely to diffuse away after being implanted into the body. Under similar conditions, the monovalent ligand was partially washed away. The adsorption kinetics were recorded by QCM-d, with regard to OGP-PEG-(Cat)₄, and 2 hours were needed to reach the equilibrium state at a concentration of 0.16 μM.

Binding Affinity and Maximum Adsorption

Figure 3A:
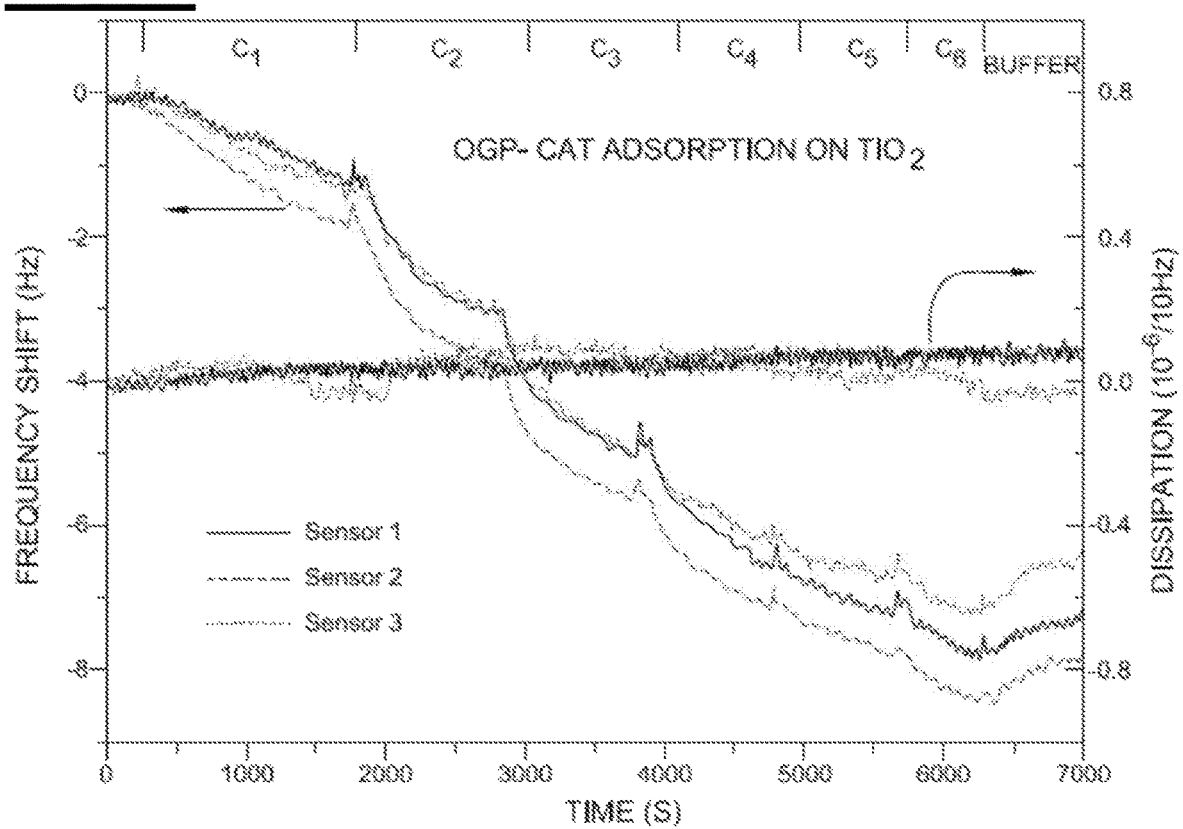
FIG. 3A is a graph generated by QCM-d showing the adsorption of OGP-Cat onto TiO$_2$ surface. The adsorption of OGP-Cat onto TiO$_2$ surface at different concentrations was measured by QCM-d, while the concentration was increased sequentially ($c_1$=0.068 μmol/L, $c_2$=0.34 μmol/L, $c_3$=1.8 μmol/L, $c_4$=7.3 μmol/L, $c_5$=13 μmol/L, and $c_6$=34 μmol/L). The adsorbed layer was then washed with 25 mM HEPES buffer. The flow rate was 0.150 mL/min. Three independent measurements (Sensors 1-3) are shown.
Figure 3B:
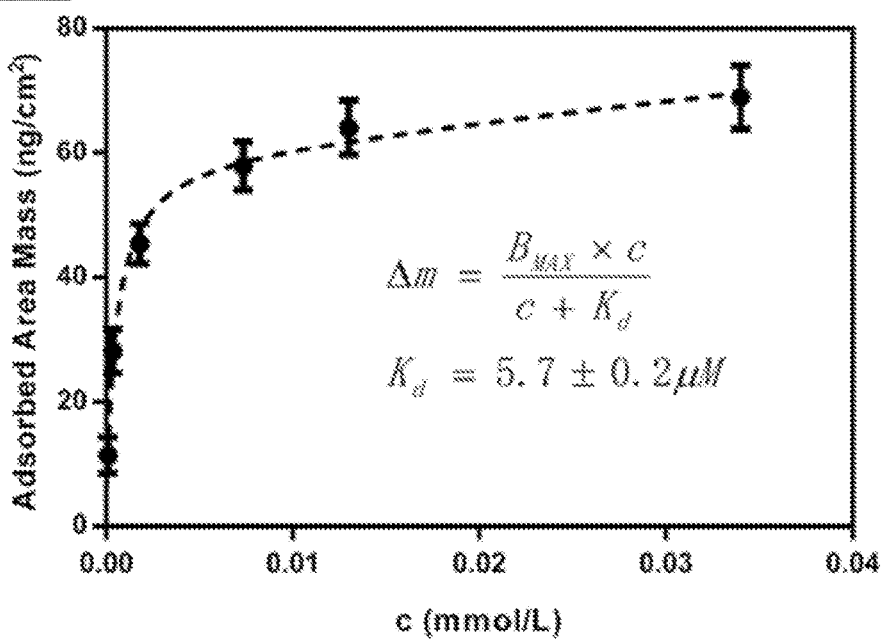
FIG. 3B is a graph showing that the disassociation constant of OGP-Cat was 5.7±0.2 μM by fitting the adsorption isotherm with single-site specific binding model, as representing with the dash line. The adsorbed area mass was calculated from the Sauerbrey Equation. Each dot with error bar was calculated based on three independent measurements.
Figure 4A:
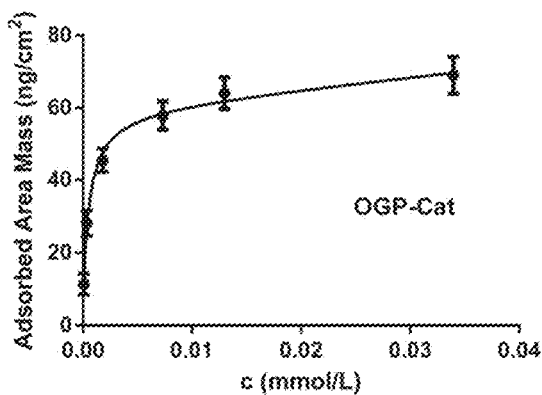
FIG. 4A-F are adsorption isotherms of catechol-functionalized dendrons according to one or more embodiments of the present invention. Each dot with an error bar was calculated based on three independent measurements. The lines represent fitting with single-site specific binding model.
Figure 4B:
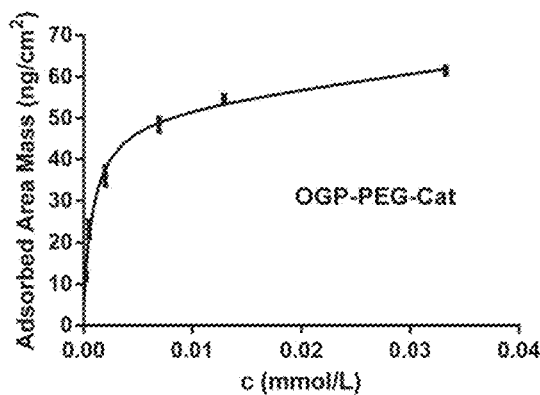
Figure 4C:
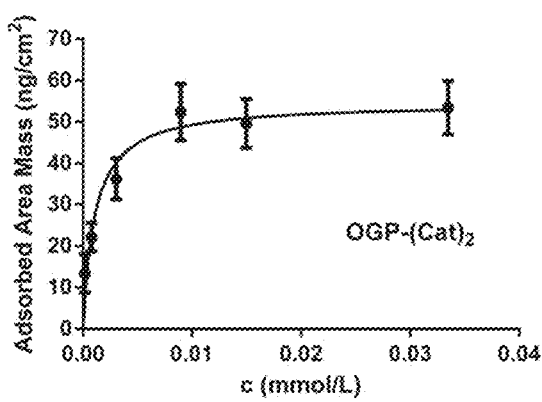
Figure 4D:
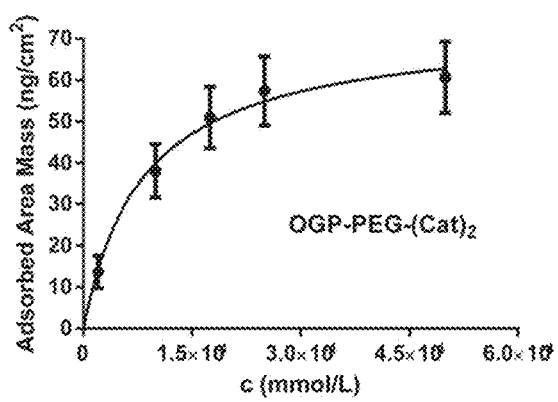
Figure 4E:
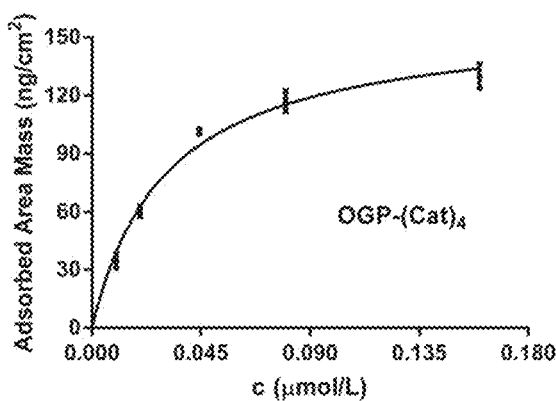
Figure 4F:
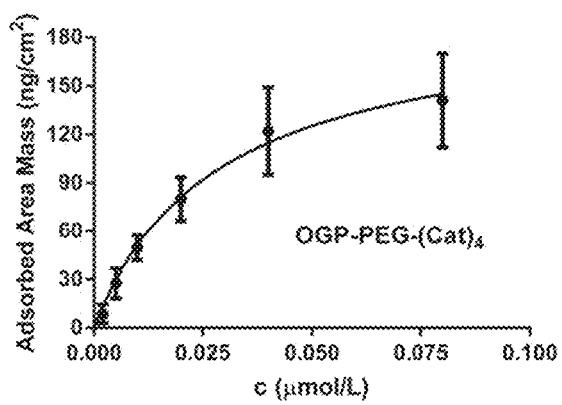

To quantitatively compare the binding affinities of the multivalent binding ligands, their adsorption properties at several different concentrations were measured. The solutions at higher concentrations were switched to flow above the sensor, until the adsorption of previous solution at lower concentration reached the equilibrium state (the change in frequency shift is smaller than the signal fluctuation, 0.05 Hz/min), taking OGP-Cat as an example shown in FIG. 3A. In these experiments, the adsorption of OGP-Cat onto $TiO_2$ surface at different concentrations was measured by QCM-d, while the concentration was increased sequentially ($c_1$=0.068 μmol/L, $c_2$=0.34 μmol/L, $c_3$=1.8 μmol/L, $c_4$=7.3 μmol/L, $c_5$=13 μmol/L, and $c_6$=34 μmol/L). At last the adsorbed layer was washed with 25 mM HEPES buffer. The flow rate was 0.150 mL/min. Three independent measurements (Sensors 1-3) are shown on FIG. 3A. The corresponding frequency shift was calculated using Sauerbrey Equation to get the adsorbed area mass. The adsorption isotherm of each molecule was drawn and fit with a single-site specific binding model to get the apparent disassociation constant ($K_d$) and maximum adsorption ($B_{max}$) of OGP-Cat as in FIG. 3B and others in FIGS. 4A-F from the adsorbed area mass at the respective concentrations. The results are summarized in Table 1, below.

TABLE 1

The apparent disassociation constant ($K_d$), maximum adsorption ($B_{max}$) and enhancement parameter ($\beta$) of catechol-functionalized dendrons to $TiO_2$ surface.

| Ligands to $TiO_2$ | $K_d(\mu M)$ [a] | $B_{max}\left(\dfrac{ng}{cm^2}\right)$ [a] | $\beta$ [b] |
|---|---|---|---|
| OGP-Cat | 5.7 ± 0.2 | 54 ± 4 | — |
| OGP-PEG-Cat | 1.0 ± 0.1 | 59 ± 2 | — |
| OGP-(Cat)₂ | 1.1 ± 0.3 | 55 ± 3 | 5 |
| OGP-PEG-(Cat)₂ | 0.08 ± 0.01 | 73 ± 4 | 12 |
| OGP-(Cat)₄ | 0.031 ± 0.003 | 160 ± 6 | 184 |
| OGP-PEG-(Cat)₄ | 0.028 ± 0.008 | 196 ± 23 | 36 |

[a] Adsorption isotherm was fit with single-site specific binding model, $\Delta m = \dfrac{B_{max} \times C}{K_d + C}$, where $\Delta m$ is the amount of adsorbed analyte, c is the concentration of the analyte solution, $B_{max}$ is the maximum adsorption, and $K_d$ is the apparent dissociation constant.
[b] Enhancement parameter is defined as the ratio of association constant of multivalent ligand to that of monovalent ligand, $\beta = K_{a,multi}/K_{a,mono}$. And it was calculated based on two sets of molecules with or without PEG linkage.

The $K_d$ decreased as the valency changed from 1, to 2, and to 4. This clearly proved that multivalent dendrons provide a stronger binding affinity. The enhancement parameters were calculated for the two series of molecules, with or without the PEG linkage. There is a 184-fold enhancement in binding affinity for OGP-(Cat)₄ with the $K_d$ of 31±3 nM, when compared to OGP-Cat. Surprisingly, the PEG linkage also influenced the binding affinity. When the valency equaled 1 or 2, the molecules with PEG showed a 6-fold and 14-fold stronger binding compared with molecules without PEG. While not wanting to be bound by theory, it is believed that this is most likely because the PEG linkage serves as a spacer and weakens the effect of any intramolecular H-bond that may form between catechol groups and the OGP(10-14) peptide chain. From the quantification results of apparent $K_d$ and $B_{max}$, for the tetravalent ligand, it is believed that the binding is strong enough to saturate and sequester the whole molecule on $TiO_2$ surface at very low bioconjugate concentrations. A solution of OGP-(Cat)₄ at 2.8 μM (100$K_d$) covers 99% of the binding sites on $TiO_2$ surfaces, at a OGP(10-14) concentration of 103 μmol/cm². The immobilization procedure simply involves immersing the $TiO_2$ surface in the solution for more than two hours.

Binding Ability of OGP-(Cat)₄ to Versatile Surfaces

Figure 5:
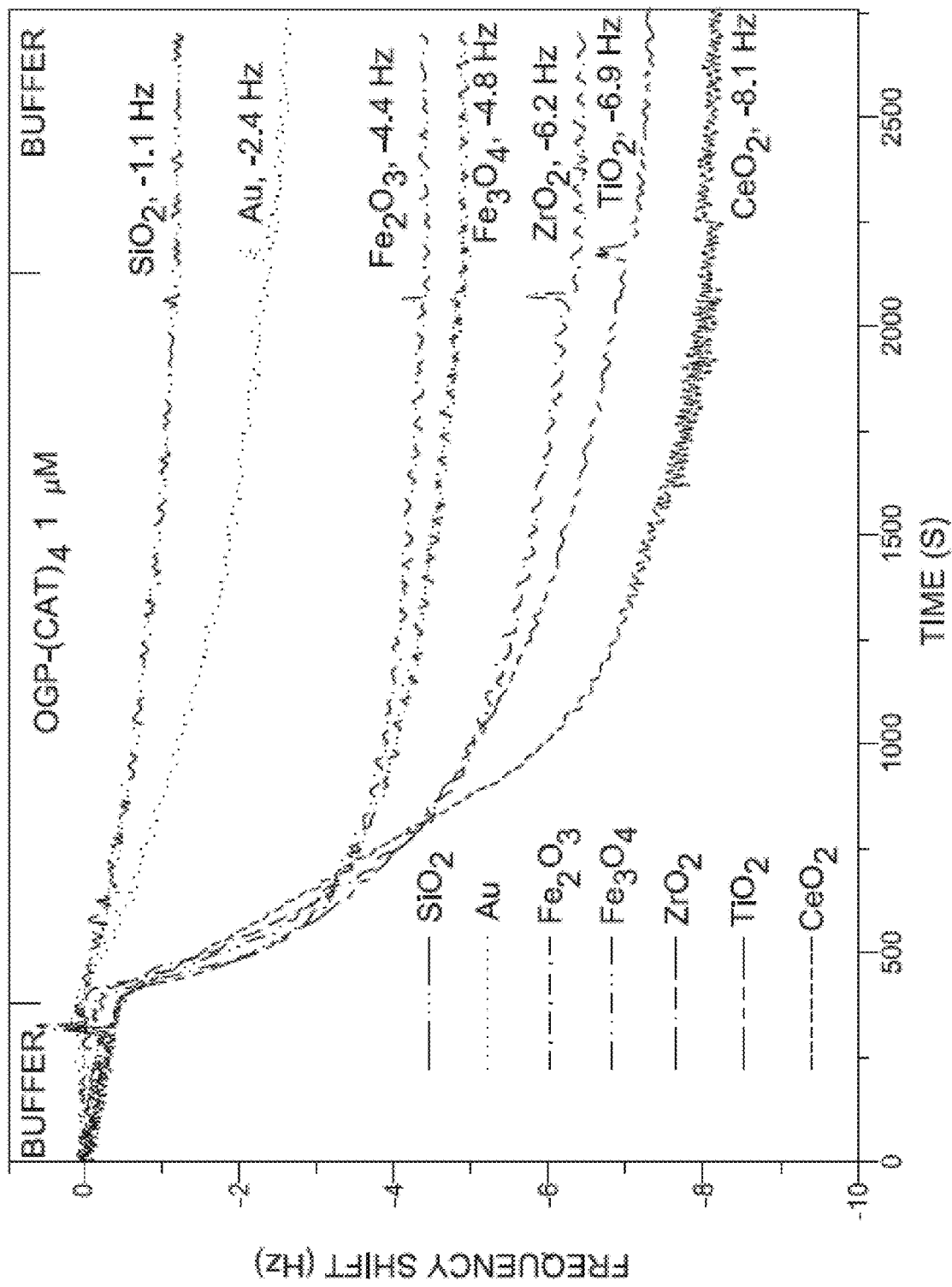
FIG. 5 is a graph showing tetravalent binding ligand OGP-(Cat)$_4$ (c=1 µM) binding affinities to Fe$_2$O$_3$, Fe$_3$O$_4$, ZrO$_2$, TiO$_2$, CeO$_2$, SiO$_2$, Au surfaces, as measured by QCM-d.
Figure 6:
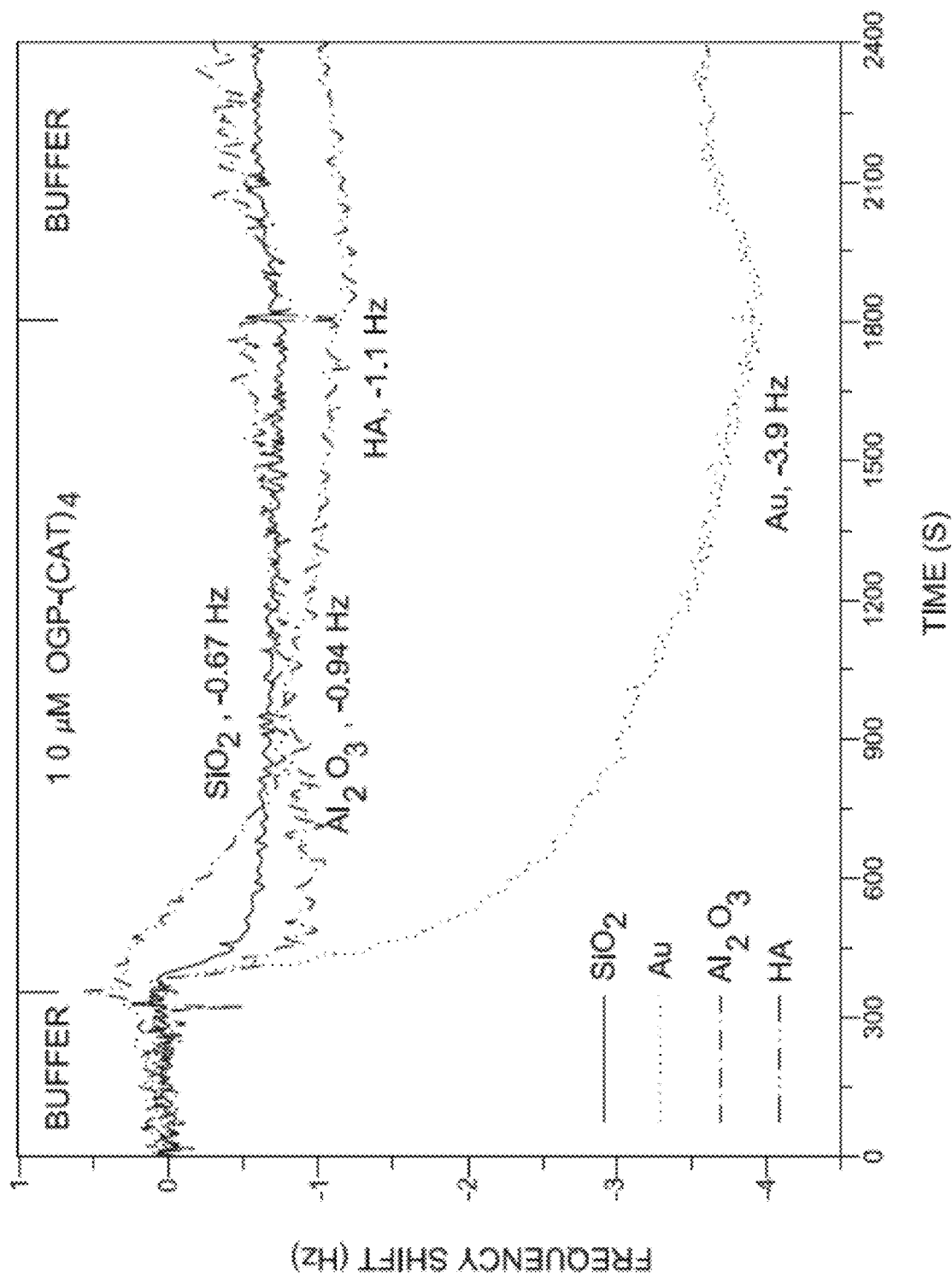
FIG. 6 is a graph showing tetravalent binding ligand OGP-(Cat)$_4$ (c=10 µM) binding affinities to SiO$_2$, Al$_2$O$_3$, hydroxyapatite (HA) and Au surfaces, as measured by QCM-d. OGP-(Cat)$_4$ as weakly adsorbed onto SiO$_2$, Al$_2$O$_3$, and HA, and relatively strongly adsorbed onto Au, as measured by QCM-d.

The adsorption of tetravalent binding ligand OGP-(Cat)₄ to a wide range of materials was tested to identify common features of materials to which the catechol-bearing ligands of various embodiments of the present invention strongly bind. As shown in FIG. 5, OGP-(Cat)₄ showed the strongest binding to $CeO_2$, $TiO_2$ and $ZrO_2$, strong binding to iron oxide ($Fe_3O_4$ and $Fe_2O_3$), some adsorption to gold, and weak adsorption to $SiO_2$. While not wanting to be bound by theory, it is believed that this is because the coordination bond between catechol and metals with empty d-orbitals or f-orbitals provides a stronger interaction than Hydrogen bonding. Limited adsorption of OGP-(Cat)₄ with materials of compounds from main group elements, including $SiO_2$, $Al_2O_3$ and hydroxyapatite (HA), was confirmed even when applying a solution at 10-times higher concentration (FIG. 6). Stronger adsorption was observed for transition metal and transition metal oxide, which was attributed to coordination bonding. Despite the strong binding with $TiO_2$, OGP-(Cat)₄ showed similar strong binding affinity and persistence under buffer washing to other biomaterial-related surfaces, including zirconia, $ZrO_2$, a widely used material in prosthetic devices, cerium oxide, $CeO_2$, and iron oxide, $Fe_3O_4$. Therefore, it is believed that OGP-(Cat)$_4$ will be highly useful for the functionalization of transition metal oxides.

OGP-(Cat)$_n$ on TIO$_2$ Surface

Figure 7:
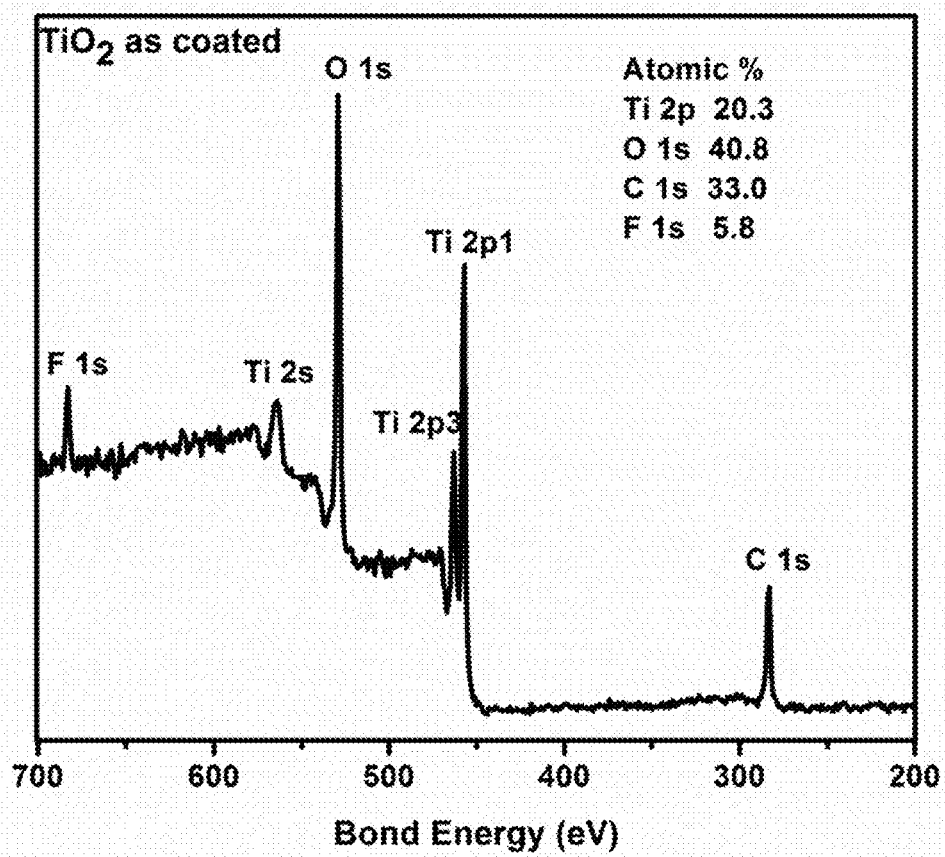
FIG. 7 is an X-Ray Photoelectron Spectroscopy (XPS) characterization of TiO$_2$ deposition after RF sputtering coating for 1 h. The obtained TiO$_2$ shows the O/Ti ratio of 2, matching with the theoretical stoichiometry. Some carbon and fluorine contamination exists.
Figure 8:
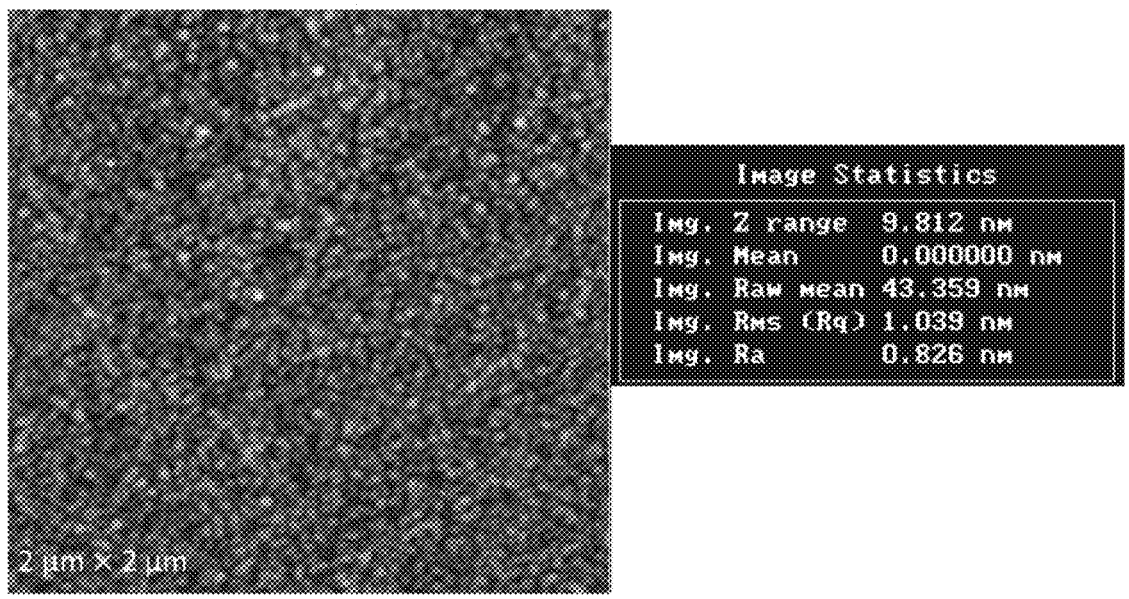
FIG. 8 is a height image and associated Image Statistics showing the surface roughness of TiO$_2$ deposition measured by atomic force microscopy (AFM). The TiO$_2$ layer was formed on the top of Si wafer after 1 h deposition.

To directly prove the existence of OGP-(Cat)$_n$ on TiO$_2$ surface, X-ray photoelectron spectroscopy (XPS) and fluorescein labeling experiments were carried out. The TiO$_2$ layer was prepared by RF sputter coating on glass slides or silica wafers. The thickness of TiO$_2$ layer was measured to be around 36 nm with O/Ti ratio equaling to 2.0 (FIG. 7). The surfaces roughness of deposited TiO$_2$ was measured by atomic force microscopy (AFM) with an RMS roughness around 1 nm (FIG. 8). As used herein, RMS roughness refers to a root mean square average of the profile height deviations from the mean line, recorded within the evaluation length RMS.

Figure 9A:
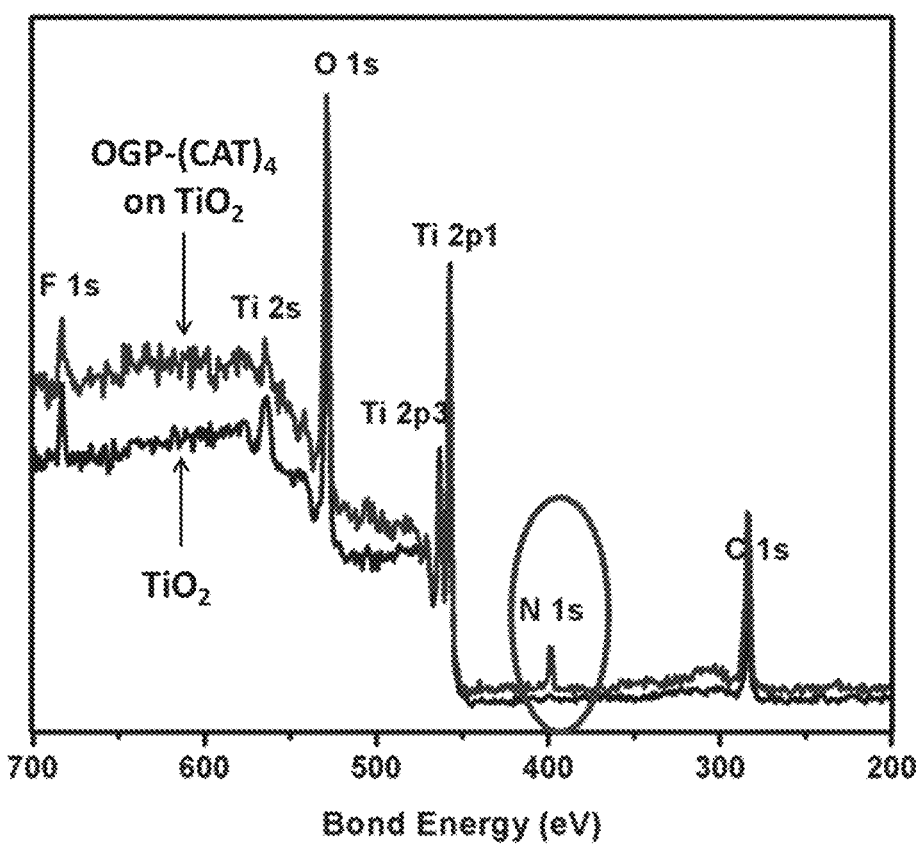
FIGS. 9A-D confirm the successful immobilization of OGP-(Cat)$_4$ on a TiO$_2$ surface.
Figure 9B:
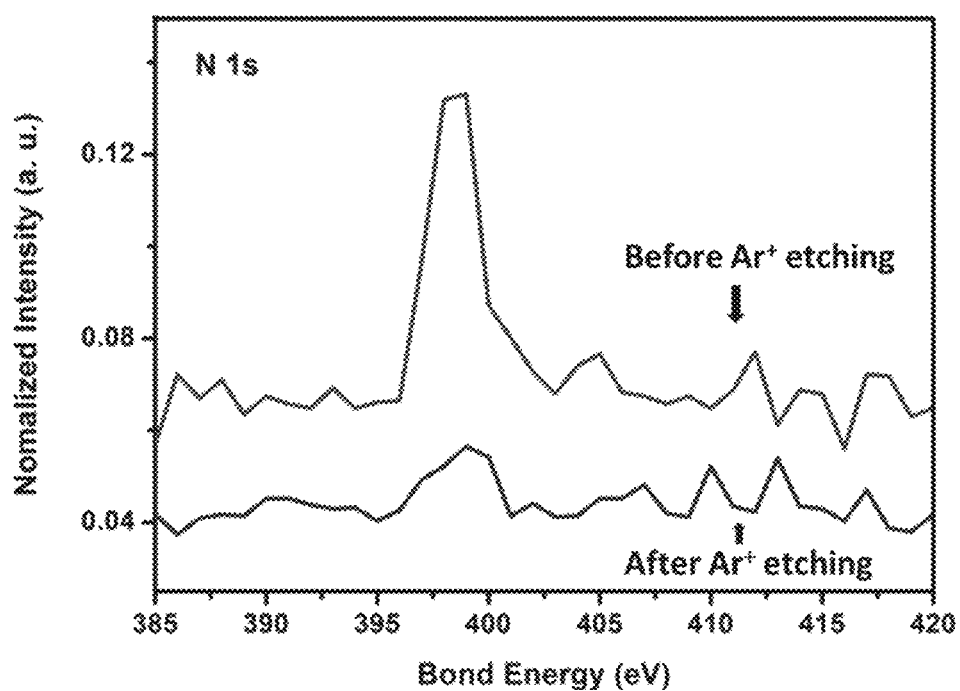

Immobilization of peptides onto TiO$_2$ surface was accomplished by immersing the TiO$_2$ substrates into the corresponding modular peptide solution and incubating it overnight at ambient temperature. The successful immobilization of OGP-Cat and OGP-(Cat)$_4$ onto TiO$_2$-coated substrates were confirmed by XPS. Nitrogen is the element contained only in the modular peptides while not in bare TiO$_2$, as shown in the XPS survey scan of bare TiO$_2$ and OGP-(Cat)$_4$ in FIG. 9A. Thus N1s signal at 400.3 eV corresponding to the amide in peptides can be used to prove the immobilization of OGP-(Cat)$_4$ onto TiO$_2$ surfaces (FIG. 9A). The adsorbed OGP-(Cat)$_4$ layer was readily removed with Ar$^+$ plasma treatment for 1 min, indicating that the N1s indeed came from the very top adsorbed peptides layer (FIG. 9B). It is noted that the N1s peaks in FIG. 9B are normalized to the highest intensity (O1s) for comparison of the signal to noise ratio.

To quantify the increase in nitrogen due to adsorption of OGP-Cat and OGP-(Cat)$_4$, the nitrogen content (N1s) was normalized with Ti content (Ti2p), and compared with TiO$_2$ substrate after incubation in HEPES buffer overnight (TiO$_2$ as control), as show in Table 2, below.

TABLE 2

The immobilization of OGP-Cat and OGP-(Cat)$_4$ and their retention on TiO$_2$ substrates. Atomic Ratios of N/Ti for the TiO$_2$ surface, the surfaces after OGP-Cat and OGP-(Cat)$_4$ immobilization, and the OGP-Cat and OGP-(Cat)$_4$ bearing surfaces after incubation in HEPES buffer.[a,b]

| | Surface | | | | | | | |
|---|---|---|---|---|---|---|---|---|
| | TiO$_2$ | OGP-Cat on TiO$_2$ | | | OGP-(Cat)$_4$ on TiO$_2$ | | | |
| | | Buffer Incubation Time | | | | | | |
| | 0 h (bare) | 12 h (control) | 0 h | 12 h | 36 h | 0 day | 3 days | 7 days | 14 days |
| N/Ti | 0 | 0.03 | 0.41 | 0.34 | 0.21 | 0.43 | 0.44 | 0.45 | 0.24 |

[a]Standard deviations are typically below 10% relative.
[b]0 h incubation in 25 mM HEPES buffer (pH = 7.41 at 25° C.) means surfaces just after TiO$_2$ coating or OGP-(Cat)$_n$ (n = 1,4) immobilization without incubation in buffer.

Figure 9C:
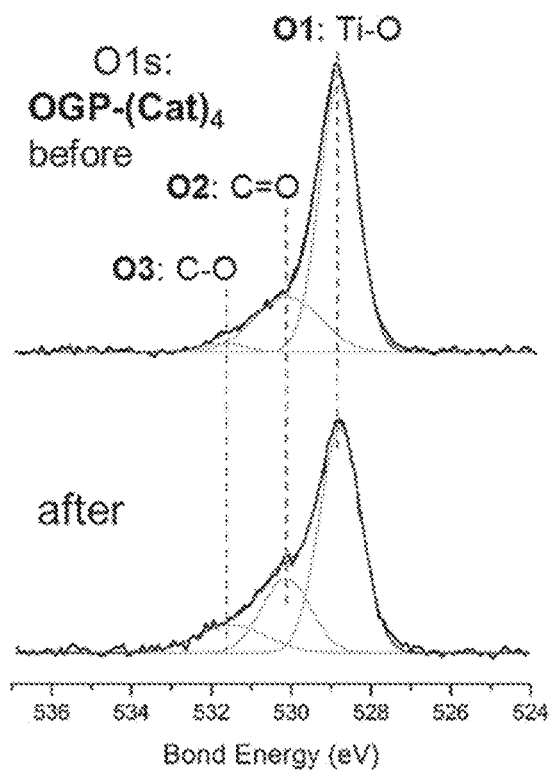
Figure 9D:
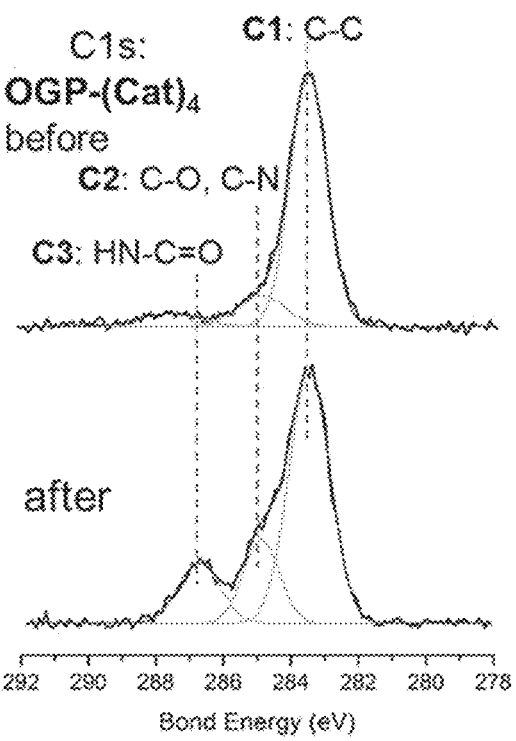

The N/Ti ratio increased from 0.03 (TiO$_2$ control) to around 0.4 (OGP-Cat: 0 h incubation in buffer, OGP-(Cat)$_4$: 0 day incubation). The presence of modular peptide OGP-(Cat)$_4$ was further proven by the significant change of C1s and O1s signatures in high resolution XPS spectra before and after the immobilization. In FIGS. 9C-D, the C1s signals were fit with Gaussian model into three components based on their respective binding energy, including carbon of C—C bond (C1, 284.8 eV), of C—O bond (C2, 286.1 eV), and of amide bond (C3, 287.8 eV). Similarly, the O1s signals were deconvoluted into three peaks: oxygen of Ti—O bond (O1, 530.2 eV), of C=O bond (O2, 531.5 eV), and of C—O bond (O3, 533.0 eV). The significant increase in the atomic ratios of C2/C1, C3/C1, O2/O1, and O3/O1 (Table 3) indicates the amide bonds and phenol rings contained in the OGP-(Cat)$_4$. The C3/N ratio, from amide bond of OGP-(Cat)$_4$, is 0.93, which is close to the theoretical value of 1.

TABLE 3

| Surface | C2/C1 | C3/C1 | O2/O1 | O3/O1 | C3/N |
|---|---|---|---|---|---|
| Bare TiO$_2$ | 0.16 | 0.08 | 0.35 | 0.04 | ∞ |
| OGP-(Cat)4 on TiO$_2$ | 0.24 | 0.29 | 0.39 | 0.21 | 0.93 |

Fluorescein-labeled modular peptide (FITC-labeled OGP-Cat) was also synthesized to visualize the presence of the immobilized peptides on TiO$_2$ surface using fluorescence microscopy. (See, Example 13). After immobilization of FITC-labeled OGP-Cat onto TiO$_2$ surfaces, the fluorescence intensity was much stronger compared to the control sample, which incubating TiO$_2$-coated substrates in a solution of FITC at identical concentration. When a TiO$_2$ pattern was present on the glass slides, it was observed that the TiO$_2$ region showed a significantly stronger fluorescence signal due to the stronger binding affinity of FITC-labeled OGP-Cat to TiO$_2$ compared with SiO$_2$. See, FIGS. 10A-B.

Retention of OGP-(Cat)$_n$ on TiO$_2$ Surface

Figure 12:
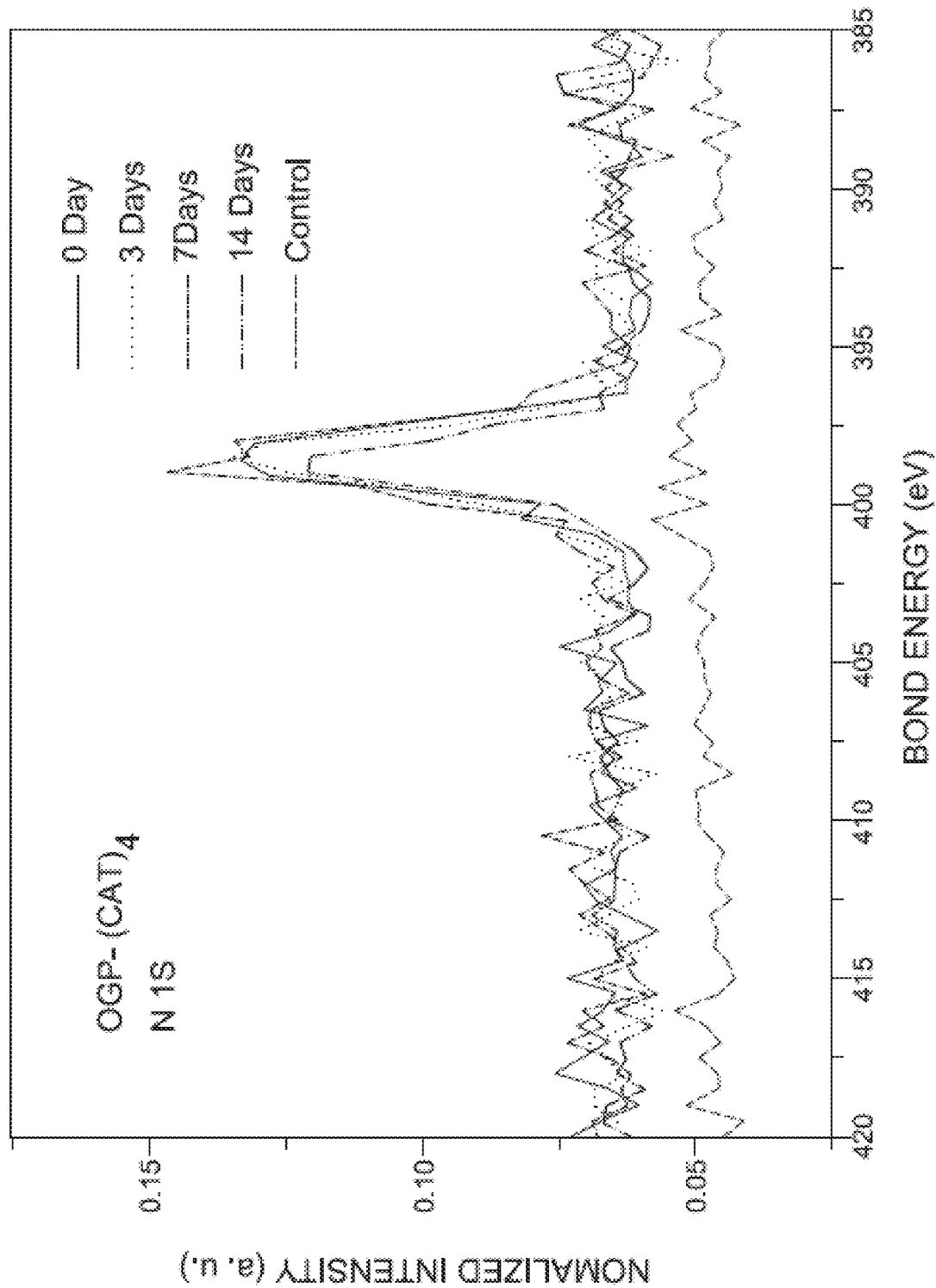
FIGS. 12 and 13 are XPS spectra of N1s signals taken after incubation of OGP-(Cat)$_4$ (FIG. 12) and OGP-Cat (FIG. 13) immobilized TiO$_2$ substrates in HEPES buffer (pH=7.4) for different durations. The immobilized OGP-(Cat)$_4$ preserved on the surface for more than 2 weeks in buffer at physiological pH, in comparison, the diffusion of monovalent ligand OGP-Cat was detected after 12 hours. The control is taken after incubation of TiO$_2$ substrates in 25 mM HEPES buffer. To compare the signal to noise ratio, all spectra were normalized to the peak of highest intensity (O1s).
Figure 13:
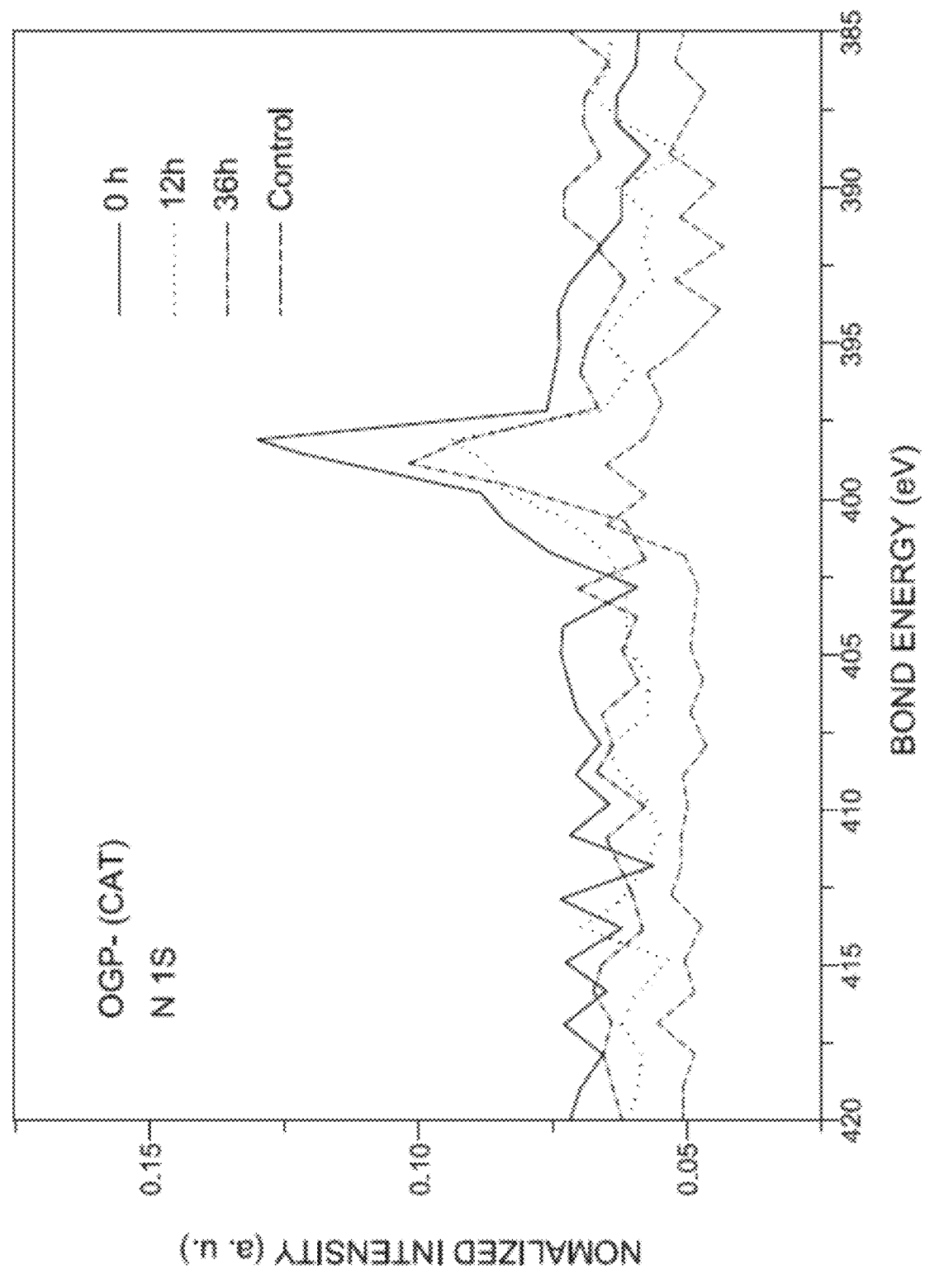

To study the stability of sequestered modular peptides on targeting surfaces, the modular peptide immobilized TiO$_2$ substrates were immersed in 25 mM HEPES buffer (pH=7.4 at 25° C.) and incubated for different durations. The mean intensity of FITC-labeled OGP-Cat immobilized TiO$_2$ substrates after incubation was quantified to detect the diffusion of FITC-labeled OGP-Cat into surrounding solution. (See FIG. 11). After 3 days incubation, the intensity deceased by about a half of the original intensity coming from FITC-labeled OGP-Cat on surfaces, indicating the dissociation of monovalent ligand. Because the N1s signals were assigned to the modular peptides, the decrease of N1s corresponds to the dissociation of adsorbed peptides from TiO$_2$ surface. As can be seen in FIGS. 12 and 13, the tetravalent ligand OGP-(Cat)$_4$ showed a longer retention time on the targeted surface (the decrease of N1s signal was not detected until after 14 days), while the monovalent ligand OGP-Cat showed a reduction in the N1s signal after only 12 hours. The atomic ratio of N/Ti for each was calculated and, as shown in Table 2, the half-life of the immobilized OGP-Cat and OGP-(Cat)$_4$ present on TiO$_2$ surface was around 36 hours and 14 days, respectively. It is believed that the mismatch of retention time for the monovalent ligands may be attributed to the sensitivity difference of XPS and fluorescence microscopy. Nevertheless, the tetravalent ligands OGP-(Cat)$_4$ were clearly present on the TiO$_2$ surface beyond 2 weeks, which is enough to trigger the cascade signaling reactions in adjacent cells.

Preferential Immobilization of OGP-(Cat)$_n$

It has been found that that the catechol-bearing dendrons have strong binding to transition metal compounds due to coordination bonding, while weaker binding to materials when only Hydrogen bond or other weak non-covalent interactions exist. Thus, if materials with both $SiO_2$ and $TiO_2$ present immersed on the surface into a solution of OGP-$(Cat)_4$, it has been found that the OGP-$(Cat)_4$ will preferentially adsorb onto the $TiO_2$ region. This provides a method to preferentially functionalize selected regions on the surface, which is useful in the fabrication of surfaces with locally restricted functionality of peptides. It was demonstrated with a partially coated glass slides containing $SiO_2$ region in the middle and $TiO_2$ in the surrounding region. After incubating the slides in the solution of OGP-$(Cat)_4$ (c=1 μM) overnight, the elements present on the surface in the respective regions was detected by XPS. The signals from $SiO_2$ and $TiO_2$ regions are quite different. The local existence of Si and Ti was confirmed in XPS. And notably, the $TiO_2$ region showed a much stronger signal in N1s, which corresponds to the adsorbed OGP-$(Cat)_4$. The atomic percentage of nitrogen from N1s in $TiO_2$ and $SiO_2$ region were 8±1% and 1.7±0.8%, respectively.

Cytotoxidty

The toxicity of the dendron of the embodiments of the present invention was tested using mouse calvarial pre-osteoblast cells (MCZTZ E1) cells. The MC3T3-E1 cells were seeded on the $TiO_2$ substrates with immobilized FITC-labeled OGP-Cat and cultured for 24 hours. The dominant green fluorescence (viability >98%) from live cells in the live/dead cell staining demonstrated that the modular peptide bioconjugates are not toxic when tethered to the surface. The cells were well spread on the peptide-bearing surfaces, which is a consistent with an adherent proliferating cell population. See also, Example 17.

XPS of OGP(10-14) Immobilized $TIO_2$-Coated Substrates

The loading amount was calculated based on the adsorption isotherm fitted with signal site specific model as shown in Table 1, above. The XPS characterization was applied to detect the immobilized peptides from the N1s signal, which is an element only contained in the amide bond in OGP-PEG-$(Cat)_4$ for $TiO_2$. substrates having 99% OGP-PEG-$(Cat)_4$ coverage (OGP-99% substrates) and 50% OGP-PEG-$(Cat)_4$ coverage (OGP-50%). The nitrogen content normalized with total amount of elements on surface was 5.8±0.3 for OGP-99% substrates, while that of OGP-50% were not distinguished from noise due to low content. See also, Example 15 below.

Effects of Immobilized OGP(10-14) on Cell Adhesion and Morphology

Because the capacity for cells to interact with growth factors is an important cell behavior, the MC3T3-E1 cells were fluorescently stained to visualize actin and vinculin proteins, to assess the organization of cytoskeleton and the spatial distribution of focal adhesion contacts respectively. After 24 hours, the MC3T3-E1 cells were attached on both OGP-99% and bare $TiO_2$ substrates and the focal adhesion contacts between cells and substrates formed. As expected, there was there was no statistical difference in cell area and aspect ratio for the cell adhesion to OGP-99% and bare $TiO_2$ substrates as it is known that OGP peptides, immobilized or dissolved, show no effects in the adhesion of MC3T3-E1 cells.

Effects of Immobilized OGP(10-14) on Cell Proliferation

Figure 14:
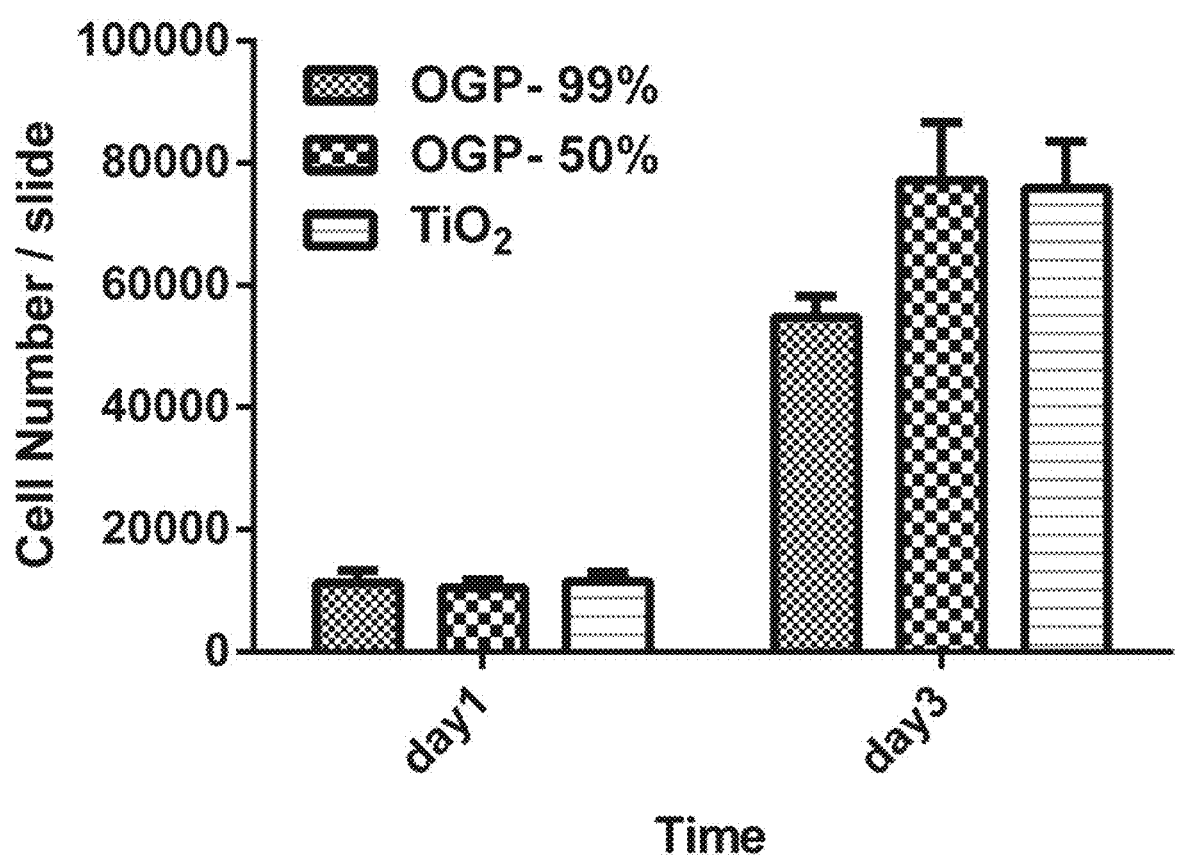
FIG. 14 is a graph showing that the immobilized OGP-PEG-(Cat)$_4$ promoted the cell proliferation, and that this effect was dose-dependent. Cell number on substrates after day 1 and day 3 were evaluated by PrestoBlue Assay. The error bar was calculated from three replicates.

The OGP-99%, OGP-50% and $TiO_2$ substrates were seeded with preosteoblast MC3T3-E1 cells with a cell density of 18 cell/$mm^2$. In the first 24 hours, the cells were mostly attaching to the surface and adjusting to the new environment, therefore, the cell number after 1 day for all three substrates was comparable. After 3 days, the MC3T3-E1 cells on OGP-99% substrates showed the highest cell number compared with the others, indicating that the OGP (10-14) peptide promoted a faster cell proliferation rate in a concentration dependent manner, as shown in FIG. 14. (See also, Examples 16 and 17, below).

Effects of Immobilized OGP(10-14) on Osteogenic Differentiation

Bone sialoprotein (BSP) constitutes approximately 8% of all non-collagenous proteins found in bone, and is important in the nucleation process of hydroxyapatite formation. Osteocalcin (OCN) is expressed solely by the osteoblast, thus it is the most specific protein for osteoblast differentiation and mineralization. The fluorescent staining of BSP and OCN, the maker proteins of osteogenic differentiation, revealed that the MC3T3-E1 cells on the OGP-99%, OGP-50% and $TiO_2$ substrates secreted abundant amounts of BSP and OCN after 2 weeks, as indicated by the strong fluorescence of red (OCN) and green (BSP) on the substrates. Similar results were observed for OGP-50% and $TiO_2$ substrates. From the enlarged images, a difference in the distribution of OCN and BSP was observed. The amount of BSP in the cytoplasm and extracellular matrix (ECM) is similar, while the OCN showed a higher concentration in the cytoplasm. This is consistent with the fact that BSP is a component in bone matrix, while OCN is secreted by osteoblasts to regulate the metabolic activities and bone-building process. Using RT-PCR, a quantitative comparison of the expressed mRNA level of BSP and OCN demonstrated a significant increase in expression of these osteogenic genes in cells on OGP-99% substrates. With enough OGP(10-14) present on the surface, the osteogenic differentiation of MC3T3-E1 cells was enhanced.

Effects of Immobilized OGP(10-14) on ALP Activity

Figure 15A:
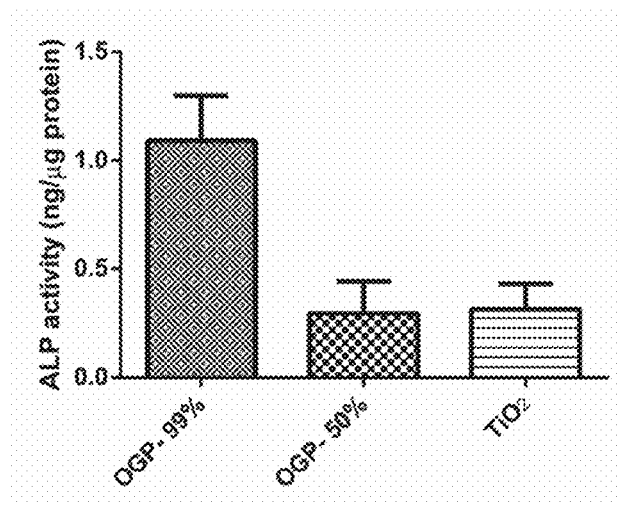
FIGS. 15A-C are graphs showing the immobilized OGP (10-14) peptide on OGP-99% substrates up-regulated the alkaline phosphatase (ALP) activity and mineralization of MC3T3 cells.
Figure 15B:
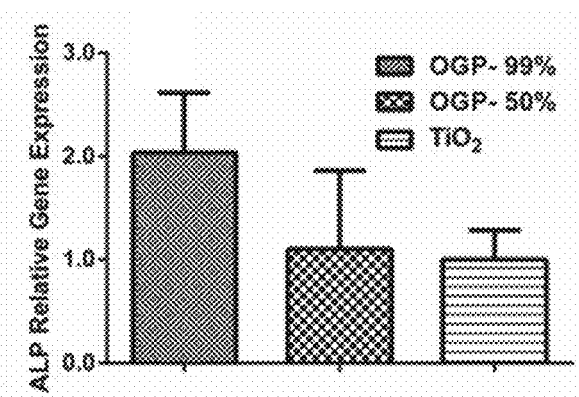

Alkaline phosphatase (ALP) plays a critical role in the process of mineral formation in tissues such as bone, cartilage, and dentin. ALP activity is a widely recognized biochemical marker for bone forming ability. A standard colorimetric assay was performed to quantify the ALP activity after culture for 18 days, and the values were normalized with total amount of protein to account for the difference of cell number content in samples. The immobilized OGP(10-14) at high concentrations exhibited an enhancement effect on the ALP activity (FIG. 15A). MC3T3-E1 cells on OGP-99% showed a 3-fold higher ALP level compared with those on OGP-50% and $TiO_2$. This up-regulation of ALP activity indicates the immobilized OGP(10-14) preserves its ability to stimulate the dephosphorylation, which is an essential activity involved in the mineralization process. The mRNA expression level of ALP in cells on OGP-99% is also higher in comparison with those on OGP-50% and $TiO_2$ as indicated in RT-PCR (FIG. 15B).

Effects of Immobilized OGP(10-14) on Mineralization

Figure 15C:
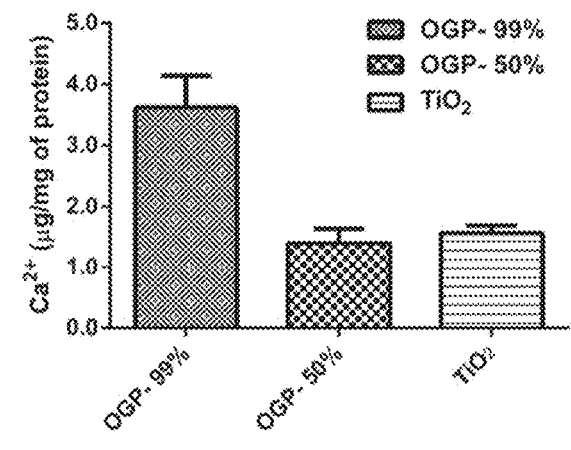
Figure 16A:
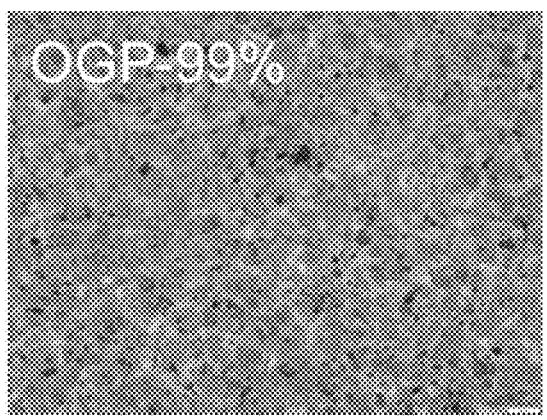
FIGS. 16A-C are images showing mineralization of MC3T3-E1 cells on substrates studied by Alizarin Red S. staining on day 14 and Ca$^{2+}$ quantification by ICP-AES on day 18. Larger sized calcified nodules were observed on OGP-99%, indicating promoted mineralization results from the higher concentration of OGP(10-14). Images of cell films on OGP-99% (FIG. 16A), OGP-50% (FIG. 16B), and TiO$_2$ (FIG. 16C) substrates after Alizarin Red S. observed under bight field microscope. The mineralized osteoids, the spherulites with dark color, ranging from 0.5 to 2 µm, were observed on all the three kinds of substrates. And only cell films on OGP-99% showed the dark mineralized chunks, ranging from 2 to 10 µm.
Figure 16B:
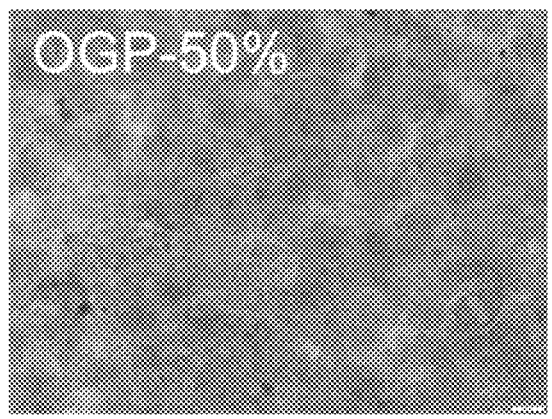
Figure 16C:
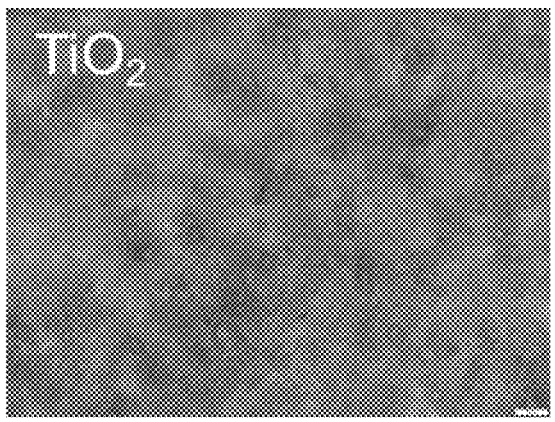
Figure 17:
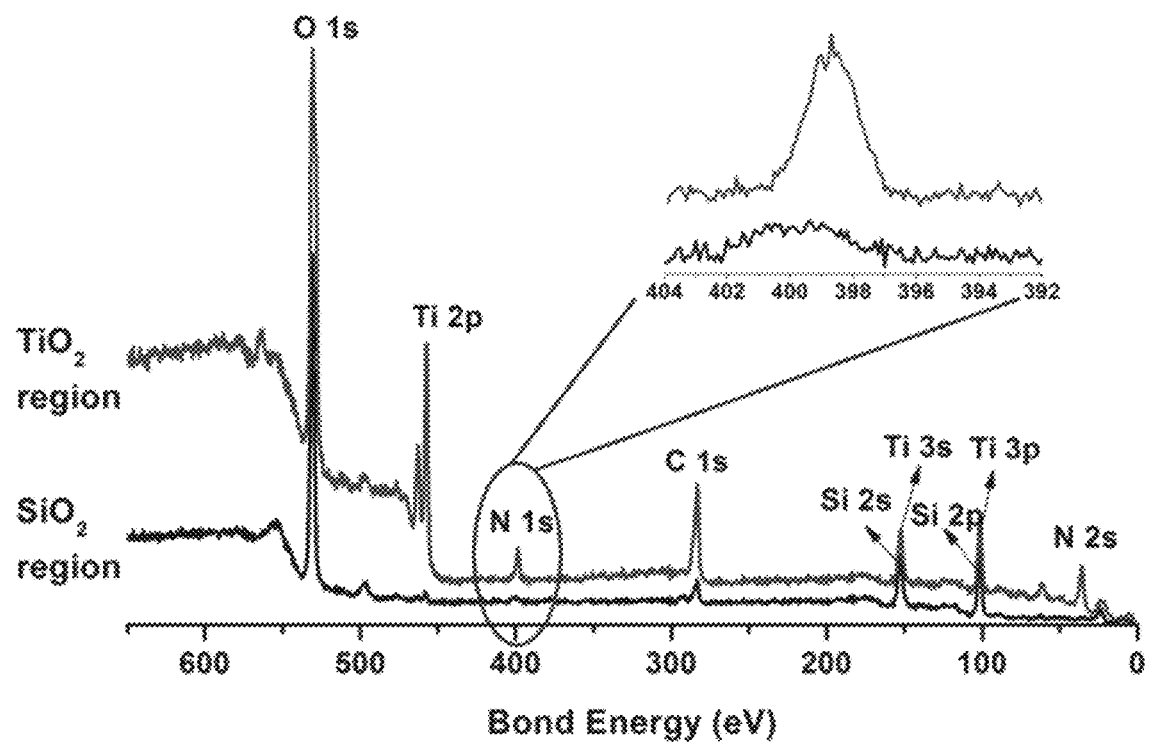
FIG. 17 is a XPS spectra showing preferential adsorption of OGP-(Cat)$_4$ to the TiO$_2$ region of a partially TiO$_2$-coated glass slide observed with XPS. The stronger signal of N1s in the TiO$_2$ region compared with that of the SiO$_2$ region indicates peptides preferentially adsorbed to the TiO$_2$ surface. The XPS signals were normalized with the strongest peak intensity (O1s). The atomic percentage of nitrogen in TiO$_2$ and SiO$_2$ region were 8±1% and 1.7±0.8%, respectively.

The appearance of calcium deposition is the phenotypic marker for the last stage of mature osteoblast. The extent of mineralized extracellular matrix (ECM) formed on OGP-99%, OGP-50% and $TiO_2$ substrates after 2 weeks was examined by staining with Alizarin Red S., a red dye that forms a complex with calcium depositions in ECM. The cell films on all three substrates were positively stained red, indicating the MC3T3-E1 cells differentiated to osteoblast and secreted mineralized ECM. Under the microscope, the mineralized osteoids, spherulites with dark red color, ranging from 0.5 to 2 µm, were observed on all three substrates (FIGS. 16A-C). But only cell films on OGP-99% substrates showed the dark mineralized chunks, ranging from 2 to 10 µm, which is attributed to the higher content of calcium in the cell films on OGP-99% substrates. The calcium content was quantified with ICP-OES after 18 days culture in non-osteogenic medium. The result is consistent with that of Alizarin Red S. staining, as show in FIG. 15C. The cell films on OGP-99% substrates exhibited more than two times higher concentration of $Ca^{2+}$ normalized by total amount of protein to account for the difference in cell numbers. Therefore it is apparent that the immobilized OGP(10-14) on surfaces promotes the mineralization of osteoblasts.

EXAMPLES

The following examples are offered to more fully illustrate the invention, but are not to be construed as limiting the scope thereof. Further, while some of examples may include conclusions about the way the invention may function, the inventor do not intend to be bound by those conclusions, but put them forth only as possible explanations. Moreover, unless noted by use of past tense, presentation of an example does not imply that an experiment or procedure was, or was not, conducted, or that results were, or were not actually obtained. Efforts have been made to ensure accuracy with respect to numbers used (e.g., amounts, temperature), but some experimental errors and deviations may be present. Unless indicated otherwise, parts are parts by weight, molecular weight is weight average molecular weight, temperature is in degrees Centigrade, and pressure is at or near atmospheric.

Materials and Equipment

Fmoc-protected amino acids were purchased from Novabiochem (San Diego, Calif.). Fmoc-NH-PEG6-Propionic acid was purchased from AAPPTec (Louisville, Ky.). Solvents were purchased from Sigma-Aldrich (St. Louis, Mo.). Unless otherwise stated, all solvents used were reagent grade and all chemicals were used as supplied. The peptide synthesis was performed on a Liberty 1 peptide microwave synthesizer (CEM Cooperation, Matthews, N.C.). Reserved-phase high performance liquid chromatography (RP-HPLC) was performed on an Akta Purifier HPLC system by using a ZORBA 300SB-C18 column (5 µm, 9.4×250 mm). The HPLC-grade solvent was degassed before usage, with recipes as A: 0.1% trifluoroacetic acid in $H_2O$ and B: 0.085% trifluoroacetic acid in 95% acetonitrile and 5% $H_2O$. The flow rate was 4 mL/min with the pressure around 13 MPa. Fluorescence images were viewed on an IX81 Microscope (Olympus, Center Valley, Pa.). Quantification of the adsorption of catechol-bearing peptides onto surfaces was performed by a Q-sense E4 system (Biolin Scientific AB, Sweden). Electrospray ionization mass spectrometry (ESI-MS) spectra were recorded on a Waters Synapt HDMS quadrupole/time-of-flight (Q/ToF) instrument in positive mode. Matrix-assisted laser desorption/ionization time-of-flight (MALDI-ToF) mass spectra were recorded on a Bruker Ultraflex III ToF/ToF mass spectrometer (Bruker Daltonics, Billerica, Mass.) equipped with Nd:YAG laser which emits at 355 nm. XPS measurements were performed on a Kratos AXIS Ultra DLD spectrometer (Manchester, U.K.) using silicon wafers or glass as substrates. A customized deposition system equipped with DC and RF magnetron sputtering sources was used to do the RF sputter coating. Thickness measurement was measured with NEWVIEW™ 7100 3D Optical Surface Profiler (Zygo, Middlefield, Conn., USA). AFM images were achieved with a Veeco Nanoscope IIIA Atomic Force Microscope (Plainview, N.Y., USA). Absorbance or fluorescence was measured using a monochromator-based multi-mode microplate reader (Biotek, Winooski, Vt.). Cell culture media, immunohistochemical staining reagents, protein assays, Live/Dead assay, Presto-Blue Assay, RNA extraction kit and cDNA reverse transcription kit was all purchased from Life technologies (Grand Island, N.Y.). The concentration of calcium ions in the supernatant was measured with inductively coupled plasma optical emission spectrometry (ICP-OES) (Agilent Technologies 700 series, Santa Clara, Calif., USA). Real time polymerase chain reaction (RT-PCR) was performed in the Applied Biosystems Real-Time PCR Instruments—7500 Fast System (Life technologies, Grand Island, N.Y.).

Statistics

Unless otherwise indicated, all experiments were conducted at three replicates (n=3). All quantitative data is presented as the average±standard deviation.

Example 1

Synthesis of Fmoc-YGFGG (SEQ. ID No. 8)-Resin

The synthesis of Fmoc-YGFGG (SEQ. ID No. 8)-Resin was carried out with solid phase synthesis via microwave assistance in a Liberty 1 peptide synthesizer, as shown in Scheme 2 below.

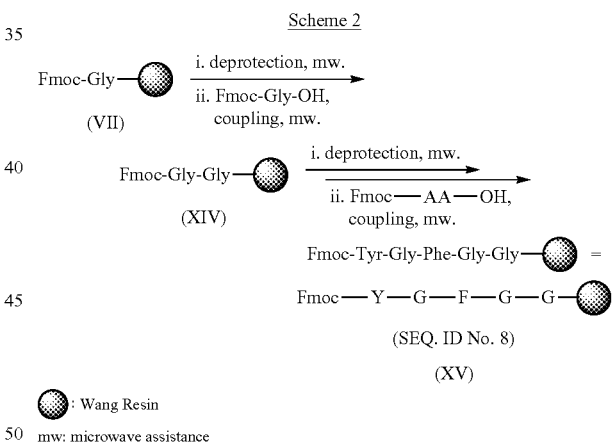

0.25 mmol Fmoc-Gly-Wang Resin was added to the reaction vessel. The resin was first swelled in DMF for 15 minutes. And then the deprotection step, which was removing the Fmoc group to generate amine, was followed by adding 20 v % piperidine in DMF with 0.1 M HOBt with microwave assistance programmed by the Liberty 1 software. After thoroughly washing the resins, in the coupling step, 5 mL Fmoc-AA-OH (AA represents amino acid) solution (4 equiv., 0.2 M in DMF), the activator HBTU (4 equiv., 2 mL of 0.5 M in DMF) and the activator base of DIPEA (8 equiv., 1 mL of 2 M in NMP) were added to couple the amino acid to the N-termini of peptides on resin with microwave assistance. The whole process was programmed and carried out automatically by the Liberty 1 peptide synthesizer. The obtained Fmoc-protected peptides on resin directly went to Example 2.

Example 2

Synthesis of dendron-YGFGG (SEQ. ID No. 8)-Resin

The Lys-based dendron was conjugated to the OGP(10-14) (SEQ. ID No. 8) peptide of Example 1, above by using Fmoc-Lys(Fmoc)-OH XV in the coupling step as shown in Scheme 3, below.

Scheme 3

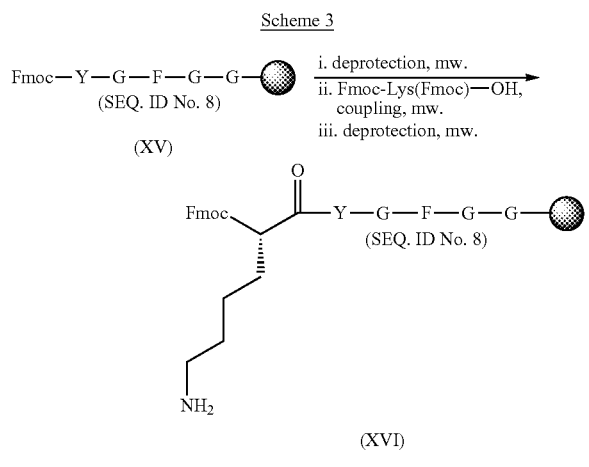

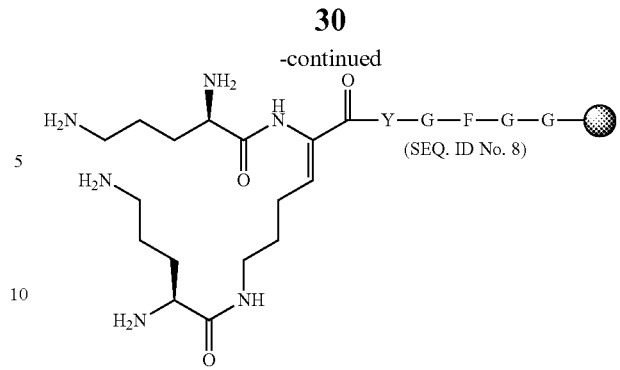

Peptide XVI was used for the synthesis of OGP-(Cat)$_2$, and peptide XVII was used for the synthesis of OGP-(Cat)$_4$. (See, Example 5). The deprotection and coupling was carried out in peptide synthesizer under standard conditions. The obtained peptides on resin directly went to Example 3.

Example 3

Synthesis of Dendron-PEG-YGFGG (SEQ. ID No. 8)-Resin

The hexaethylene glycol flexible linkage IX was conjugated to the peptides on resin XV of Example 2 by using Fmoc-NH-PEG6-propionic acid IX in the coupling step, as shown in Scheme 4 below.

Scheme 4

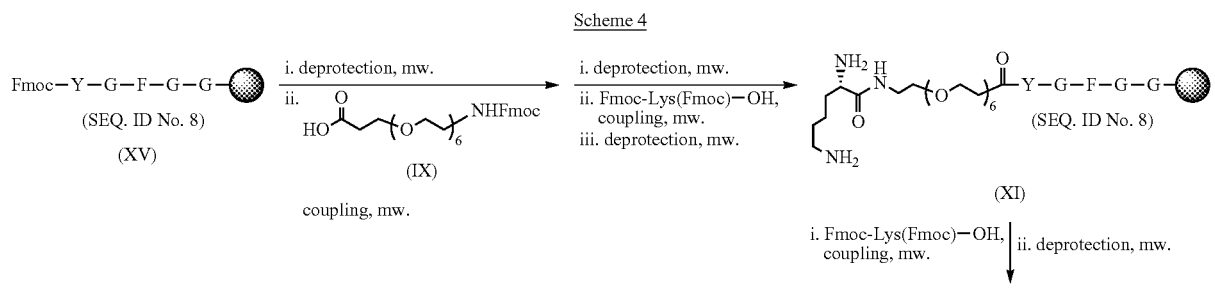

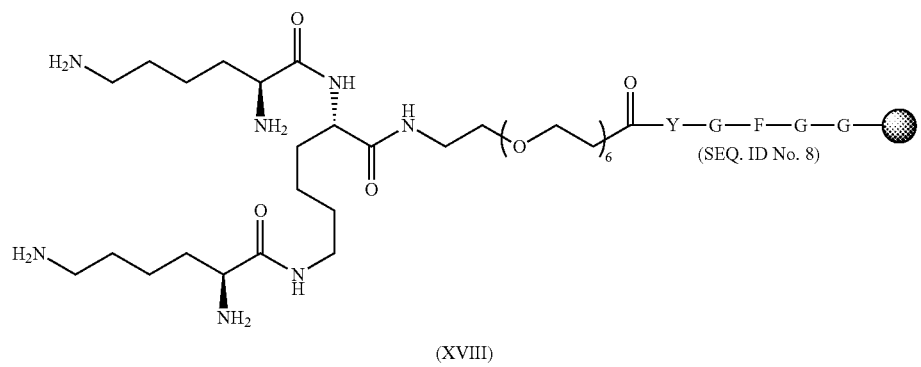

Then the Lys-based dendron was linked to the peptides, as shown in Scheme 4 above. Peptide XI was used for the synthesis of OGP-PEG-(Cat)$_2$, and peptide XVIII was used for the synthesis of OGP-(Cat)$_4$. (See Example 5). The deprotection and coupling were carried out in a peptide synthesizer under standard conditions. The obtained peptides on resin directly went to Example 5.

Example 4

Synthesis of 2,2-Dimethyl-1,3-Benzodioxole-5-Propanoic Acid XII 2,2-Dimethyl-1,3-benzodioxole-5-propanoic acid XII was synthesized as set forth in Scheme 5, below.

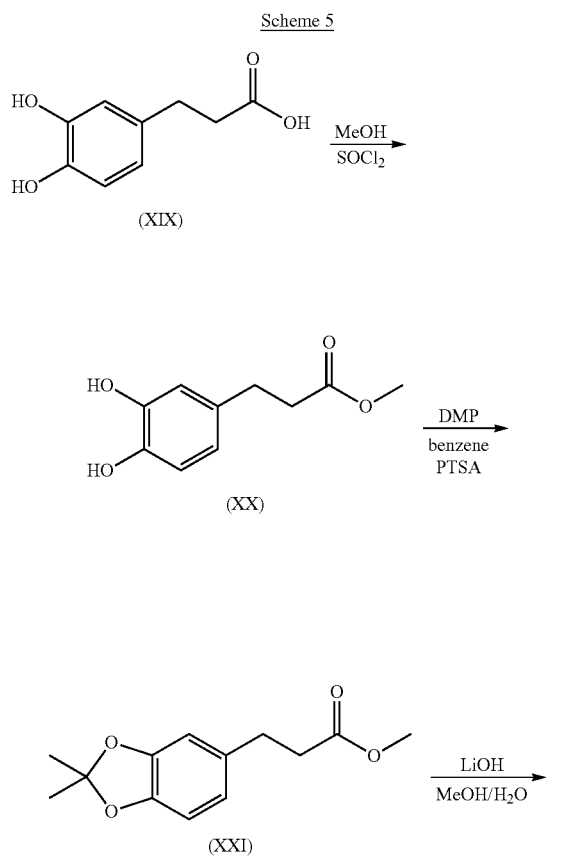

Scheme 5

Synthesis of methyl 3-(3,4-dihydroxphenyl)propanoate XX 3,4-dihydroxyhydrocinnamic acid XIX (12.5 g, 68.6 mmol) was dissolved in 100 mL anhydrous MeOH and cooled with ice bath. Thionyl chloride (13.0 mL, 171.5 mmol) was added dropwise with stirring. Ice bath was removed after 30 min and the reaction was stirred at r.t. for 24 h. Solvent was removed by rotary evaporation. Dried under high vacuum gave product as a dark blue viscous oil quantitatively. The oily product became solid after being placed in the freezer. $^1$H NMR (500 MHz, CDCl$_3$): 2.61 (t, J=7.70 Hz, 2H), 2.83 (t, J=7.70 Hz, 2H), 3.69 (s, 3H), 5.69 (br. s., 2H), 6.60 (dd, J=8.07, 1.96 Hz, 1H), 6.71 (d, J=1.96 Hz, 1H), 6.77 (d, J=8.07 Hz, 1H). $^{13}$C NMR (125 MHz, CDCl$_3$): 30.25, 35.94, 51.89, 115.43, 120.51, 133.19, 142.12, 143.66, 174.38.

Synthesis of 2,2-Dimethyl-1,3-benzodioxole-5-propanoic Acid Methyl Ester XXI

Methyl 3-(3,4-dihydroxyphenyl)propanoate XX (5.18 g, 26.4 mmol) and 2,2-dimethoxypropane (13 mL, 106 mmol) were added to 200 mL anhydrous benzene in a 250 mL two-neck round bottom flask. One neck of the flask was equipped with Soxhelet extractor and the other neck was sealed with a septum for sampling. The thimble in the extractor was filled with granular anhydrous CaCl$_2$ to trap MeOH and H$_2$O. The mixture was flushed with argon for 10 min and then heated to reflux under N$_2$ for 5 min. p-Toluenesulfonic acid monohydrate (PTSA, 0.25 g, 1.3 mmol) was added quickly and the reaction was monitored by the ferric chloride test. The reaction was stopped and cooled to room temperature once a negative test was achieved (about 3 hrs). The yellow reaction mixture was filtered through a short silica-gel column and washed with DCM. The combined filtrate and washings were concentrated via rotovap and purified by silica-gel column. The eluent was DCM/hexane (1/50, v/v) followed by EtOAc/hexane (1/25, v/v). Yellow oil (5.5 g, 88%) was obtained as the product. $^1$H NMR (300 MHz, CDCl$_3$): 1.65 (s, 6H), 2.58 (t, J=7.90 Hz, 2H), 2.85 (t, J=7.76 Hz, 2H), 3.67 (s, 3H), 6.56-6.67 (m, 3H). $^{13}$C NMR (75 MHz, CDCl$_3$): 25.81, 30.71, 36.05, 51.57, 108.01, 108.52, 117.63, 120.39, 133.60, 145.79, 147.45, 173.31.

Synthesis of 2,2-Dimethyl-1,3-benzodioxole-5-propanoic Acid XII

LiOH aqueous solution (0.33 g, 13.9 mmol dissolved in 8 mL H$_2$O) was added to a methanol solution of 2,2-Dimethyl-1,3-benzodioxole-5-propanoic acid methyl ester XXI (1.64 g, 6.93 mmol dissolved in 8 mL of methanol) in portions. After overnight reaction, methanol was removed by rotovap. The pH of the remaining solution was adjusted to 5-6 by 2 M HCl. The mixture was then extracted with EtOAc for three times. The combined organic layers were dried with Na$_2$SO$_4$ and evaporated in vacuo to obtain a white solid as product (1.30 g, 84%). $^1$H NMR (500 MHz, CDCl$_3$): 1.65 (s, 6H), 2.55-2.63 (m, 2H), 2.79-2.88 (m, 2H), 6.55-6.66 (m, 3H), 9.34 (br. s., 1H). $^{13}$C NMR (125 MHz, CDCl$_3$): 25.79, 30.72, 36.70, 108.01, 108.53, 117.60, 120.37, 133.61, 145.80, 147.48, 179.38.

Example 5

Synthesis of OGP-(Cat)$_n$ and OGP-PEG-(Cat)$_n$

OGP-(Cat)$_n$ and OGP-PEG-(Cat)$_n$ were synthesized as shown in Scheme 6, below.

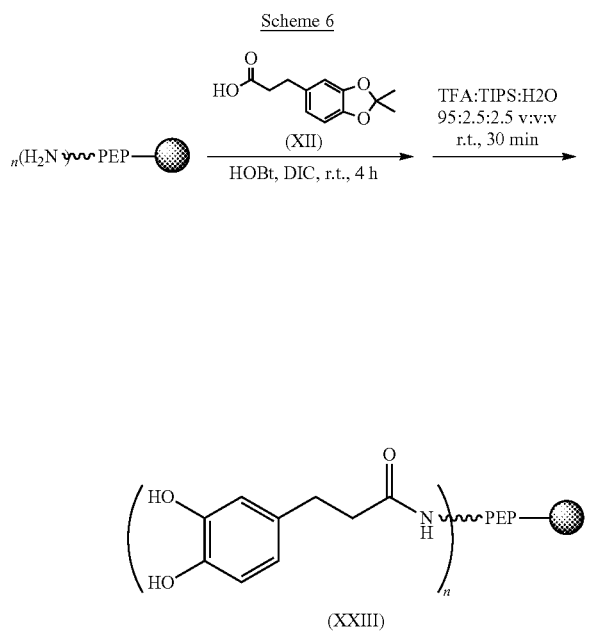

Scheme 6

The resins with peptides 1-4 (See Examples 2, 3, above) were each transferred into a peptide reaction vessel. For each peptide, the resins were firstly swelled in DMF for 15 minutes. After aspiration, 20 mL DMF was added into each reaction vessel. With nitrogen boubling the solution, acetonide-protected 3,4-dihydroxyhydrocinnamic acid (4 equiv. to each amine), HOBt (10 equiv. to each amine), and DIC (10 equiv. to each amine) were added sequentially to each reaction vessel. Each reaction was carried out at ambient temperature with nitrogen boubling for 4 hours. After aspiration, the resin in each reaction vessel was washed by DMF, DCM and MeOH, three times each for 2 minutes. Then, each of the resins were immersed in 30 mL cleavage cocktail (trifluoroacetic acid 95%, triisopropylsilane 2.5%, H$_2$O 2.5%, v/v) for 0.5 hour with nitrogen boubling. The solutions were collected and concentrated to ~3 mL with Roto Vapor. The peptides were precipitated in cold ether three times. Due to the poor solubility of products in 1×PBS buffer, all of the peptides were dissolved in a mixed solvent of 1×PBS buffer and ethanol (v/v 1:1), followed by transfer into dialysis tube (MWCO 500 Da), and dialysis against dilute HCl solution (pH=3~4). After dialysis, the product may precipitate, so the insoluble portion was dissolved with ethanol, combined with the solution inside the dialysis tube, and freeze dried. The gradient elution of RP-HPLC changed linearly from 10% to 80% B within 15 column volumes.

The catechol-bearing peptides were characterized with either Electrospray Ionization Mass Spectrometry (ESI-MS) or MALDI-ToF mass spectrometry, depending on their molecular weight. OGP-Cat: $[M+H]^+$ m/z was calculated to be 792.4 and measured at 792.6. OGP-(Cat)$_2$: $[M+H]^+$ m/z was calculated to be 956.4 and measured at 956.5. OGP-(Cat)$_4$: $[M+Na]^+$ m/z was calculated to be 1562.7 and measured at 1562.7. OGP-PEG-Cat: $[M+H]^+$ m/z was calculated to be 1127.5 and measured at 1127.6. OGP-PEG-(Cat)$_2$: $[M+Na]^+$ m/z was calculated to be 1313.6 and measured at 1313.7. OGP-PEG-(Cat)$_4$: $[M+Na]^+$ m/z was calculated to be 1897.9 and measured at 1898.3. See FIGS. 1A-F. The total yield calculated from the staring Fmoc-Gly-Wang Resin (0.25 mmol) was: OGP-Cat: 25%, OGP-(Cat)$_2$: 23%, OGP-(Cat)$_4$: 12%, OGP-PEG-Cat: 20%, OGP-PEG-(Cat)$_2$: 15%, and OGP-PEG-(Cat)$_4$: 9%.

Example 6

Synthesis of FITC-Labeled OGP-Cat

FITC-labeled OGP-Cat was synthesized as set forth in Scheme 7, below.

Scheme 7

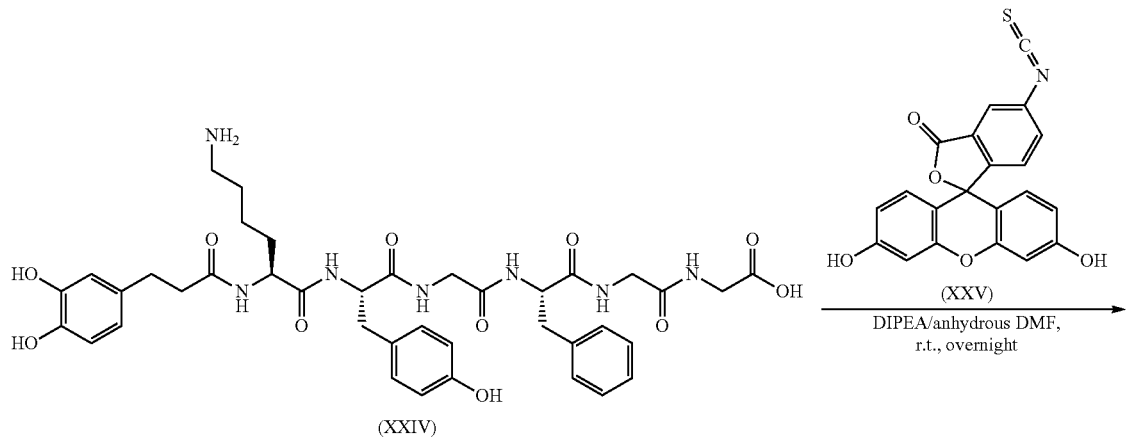

-continued

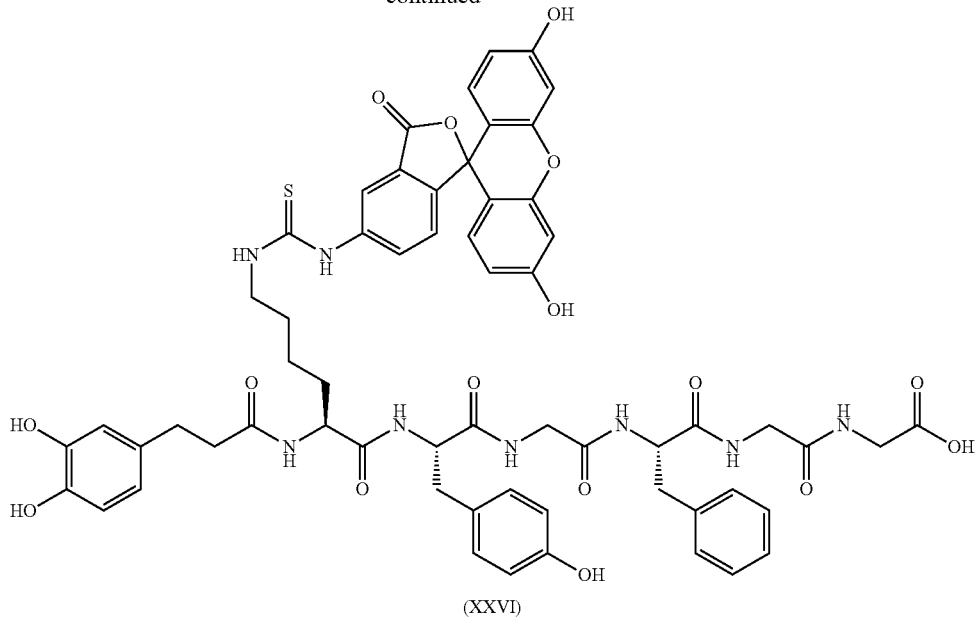

(XXVI)

To the solution of OGP-Cat (6 mg) XXIV and N,N-Diisopropylethylamine (DIPEA) (3 mg, 3 equiv.) in 0.2 mL anhydrous DMF, the solution of fluorescein isothiocyanate (FITC) XXV (6 mg, ~2 equiv.) in 0.2 mL anhydrous DMF was added dropwise. The mixture was covered with aluminum foil and stirred at ambient temperature overnight. After the reaction, DMF was evaporated under vacuum, and the obtained orange solid was dissolved in 15 mL 25 mM HEPES buffer and filtered through a 0.22 μm filter to separate the overdosed insoluble FITC. The product was characterized with MALDI-ToF mass spectrometry. FITC-labeled OGP-Cat [M+H]$^+$ m/z was calculated to be 1181.4 and found in 1181.6. The solution of FITC-labeled OGP-Cat (0.5 mM) was used directly to immobilize onto TiO$_2$ surface without further purification.

Example 7

Quartz Crystal Microbalance with Dissipation (QCM-d) Measurement

Quartz crystal microbalance with dissipation (QCM-d) was used to determine the binding isotherm for OGP-(Cat)$_4$ on TiO$_2$, Fe$_2$O$_3$, Fe$_3$O$_4$, ZrO$_2$, CeO$_2$, SiO$_2$, and Au substrates. The AT cut sensors were purchased from Biolin Scientific AB (Sweden) and cleaned before use according to the protocol provided by the company. The sensor was excited at 5 MHz as its fundamental frequency. The frequency shift (Δf) and dissipation (ΔD) were measured at $3^{rd}$, $5^{th}$, $7^{th}$, $9^{th}$, $11^{th}$ and $13^{th}$ overtones. 25 mM HEPES buffer (pH=7.40 at 25° C.) was used as the flow medium. Sensors were mounted in the modules immediately after cleaning. HEPES buffer flowed above the sensors until a flat baseline was achieved at flow rate of 0.150 mL/min. Then solutions of catechol-bearing peptide (OGP-(Cat)$_4$) in HEPES buffer were introduced and the flow continued until the adsorption reached its equilibrium state. If necessary, solutions at higher concentrations were introduced sequentially. Lastly, HEPES buffer was introduced again to wash the adsorbed layer. Three independent measurements were done simultaneously. The results are reported on FIG. 5.

Example 8

Calculation of Adsorbed Area Mass

The QCM-d measurements in Example 7 above may be used to calculate the adsorbed area mass. The adsorbed area mass was proportional to the frequency shift (Δf) and calculated by the Sauerbrey Equation. Sauerbrey Equation is $$\Delta m = -\frac{C}{n}\Delta f_n,$$

where C is the mass sensitivity constant with the value of 17.7 ng Hz$^{-1}$ cm$^{-2}$ for 5 MHz fundamental frequency crystal, n is the frequency overtone number, and n=7 was chosen to calculate the adsorption area mass. As long as the adsorbed mass is small compared to the crystal, sufficiently thin, and has limited viscoelastic coupling with the surrounding medium (ΔD<1×10$^{-6}$ per 10 Hz), this relationship is valid. Adsorbed area mass measured from QCM-d includes water contained in the adhering layer. For adsorptions of OGP-(Cat)$_n$ and OGP-PEG-(Cat)$_n$ (n=1, 2, 4) onto substrates, ΔD were below 1×10$^{-6}$ per 10 Hz, and measurements from multiple overtones were close to each other, indicating adsorbed films were rigid, and the effect from content of water was slight.

Example 9

Models Used to Fit the Adsorption Isotherm

The adsorption isotherms of OGP-(Cat)$_n$ and OGP-PEG-(Cat)$_n$ (n=1, 2, 4) binding to TiO$_2$ surface respectively were fit using a single-site specific binding model, $$\Delta m = \frac{B_{max} \times C}{K_d + C},$$

where $\Delta m$ is the amount of adsorbed analyte, c is the concentration of the analyte solution, $B_{max}$ is the maximum adsorption of analyte on the surface, and $K_d$ is the apparent dissociation constant.

Example 10

Sputtering Coating of $TiO_2$

For the $TiO_2$ substrates used herein, glass slides and silicon wafers were cleaned by sonication in 2% SDS solution for 30 minutes followed by thoroughly rinsing with water, dried with nitrogen and UV-ozone treatment for 20 minutes. The $TiO_2$ target (99.99% pure, 2.00" diameter× 0.125" thickness) were purchased from Kurt J. Lesker (USA). The $TiO_2$ films were deposited by RF-magnetron sputtering using the following conditions at ambient temperature for 1 h, power 75 W, 5 $V_{bias}$, deposition distance 5 cm, Ar 86 sccm, $O_2$ 9 sccm, and total pressure 42 mtorr ($p_{Ar}$=34 mtorr, $p_{o2}$=8 mtorr). For the fabrication of $TiO_2$ patterns on glass slides, 300 mesh Cu grids were placed on the top of glass.

The obtained $TiO_2$ shows the O/Ti ratio of 2, matching with the theoretical stoichiometry. Some carbon and fluorine contamination existed. See FIG. 7.

Example 11

Immobilization of OGP-(Cat)$_n$ and OGP-PEG-(Cat)$_n$ onto $TiO_2$-Coated Substrates OGP-(Cat)$_n$ and OGP-PEG-(Cat)$_n$ (n=1, 2, 4) were dissolved in HEPES buffer at concentrations of 50 µmol/L. Substrates were immersed into the solution (800 µL for 20 mm×20 mm glass slides, 500 µL for 5 mm×5 mm silica wafer) and incubated at ambient temperature overnight. After that, the substrates were rinsed thoroughly with water to wash away the unbounded molecules, dried with nitrogen and subjected to further study.

Example 12

X-Ray Photoelectron Spectroscopy (XPS)

X-ray photoelectron spectroscopy (XPS) was used to confirm the presence of the OGP peptide on the surface of the substrate by the presence of nitrogen. The XPS measurements were performed on a Kratos AXIS Ultra DLD spectrometer. The X-ray source was monochromated Al Kα, scanning over a binding-energy range of (0 to 700) eV with a dwell time of 100 ms. The analyzer pass energy was 110 eV for the survey spectra and 11 eV for the high-resolution C1s, N1s, and O1s scans. Each spectrum was collected over a 300×700 µm sample area. The results are reported in FIGS. 7, 9A-D, 12, 13, and 17.

Example 13

Fluorescence Intensity Measurement

The florescence intensity of FITC-OGP-(Cat)$_n$ (n=1, 2, and 4) on $TiO_2$, $Fe_2O_3$, $Fe_3O_4$, $ZrO_2$, $CeO_2$, $SiO_2$, and Au substrates was viewed with an inverted IX81 Microscope (Olympus, Center Valley, Pa.) with mercury bulb excitation and the appropriate filters. Displayed images were taken using identical settings, including exposure time (4.99 s), gain (10.04) and magnification (×20). The mean intensity was calculated based on at least 10 randomly chosen sites observed under the same conditions. The results for $TiO_2$ and $SiO_2$ substrates are reported in FIGS. 10A-B and 11.

Example 14

Sterilization of Substrates and OGP-PEG-(Cat)$_4$ Solution

The $TiO_2$-coated glass slides were sterilized by washing with ethanol and UV irradiation for 30 minutes. The OGP-PEG-(Cat)$_4$ in HEPES buffer solution was sterilized by filtration through a 0.2 µm sterile syringe filter (EMD Millipore Millex).

Example 15

Fabrication of Substrates for Cell Study

The immobilization of OGP-PEG-(Cat)$_4$ onto $TiO_2$ substrates is convenient by immersion the substrates into the solution of OGP-PEG-(Cat)$_4$ and followed incubation for overnight. Due to the strong binding affinity, the concentration of the OGP-PEG-(Cat)$_4$ solution is very low. By using $C_1$=100×$K_d$=2.8 µmol/L and $C_2$=$K_d$=28 nmol/L, OGP-PEG-(Cat)$_4$ modified $TiO_2$ substrates, OGP-99% and OGP-50%, were successfully prepare with 99% and 50% coverage of maximum adsorption, respectively, as shown in Table 4. Table 4 shows the immobilization of OGP(10-14) on $TiO_2$ surface by immersion the substrates in the solution of OGP-PEG-(Cat)$_4$ at different concentration for overnight and their respective load amount calculated in theory and measured with XPS.

TABLE 4

Substrates for bioactivity evaluation.

| Substrates | OGP-PEG-(Cat)$_4$ (µmol/L) | Immobilized OGP(10-14) (pmol/cm2) | Nitrogen content from XPS (%) |
|---|---|---|---|
| OGP-99% | 2.8 | 103 | 5.8 ± 0.3 |
| OGP-50% | 2.8 × 10-2 | 52 | — |
| $TiO_2$ | 0 | 0 | — |

Note:
The load amount was calculated with the single site specific binding model, $\Delta m = \frac{B_{max} \times C}{K_d + C}$, where $\Delta m$ is the amount of adsorbed analyte, c is the concentration of the analyte solution, $B_{max}$ is the maximum adsorption of analyte onto the surface, and $K_d$ is the apparent dissociation constant. For OGP-PEG-(Cat)$_4$, $K_d$ is 0.028 ± 0.008 µmol/L, and $B_{max}$ is 196 ± 23 ng/cm$^2$, as characterized in the previous work.

Example 16

Cell Culture

MC3T3-E1 mouse preosteoblast (passage 17) were expanded and cultured in α-MEM media (Gibco, Life Technologies, Grand Island, N.Y.) supplemented with 10% fetal bovine serum (FBS) (Invitrogen), 100 units/mL penicillin (Invitrogen), and 100 µg/mL streptomycin (Invitrogen) at 37° C. in a 5% $CO_2$ humidified atmosphere. The cells were subcultured every 3 days in the presence of 0.25%

(w/v) trypsin and 0.5% (w/v) ethylenediaminetetraacetic acid tetrasodium salt (EDTA) solution. Cells were seeded on substrates at 18 cells/mm$^2$ and fed every two days.

Example 17

Viability Assay

Viability of the cell culture of Example 16 above was evaluated using a Live/Dead viability/cytotoxicity kit (Invitrogen, UK). Briefly, 5 μL of the 4 mM Calcein-AM stock solution and 10 μL of the 2 mM ethidium homodimer-1 (EtmD-1) stock solution were added to 10 mL of cell culture medium to prepare the Live/Dead staining solution. 1 mL of staining solution was added into each well in a 6-well plate, after aspiration of the old medium. The samples were incubated for 10 min in Live/Dead staining solution. The staining solution was removed and the samples were viewed under the IX81 fluorescence microscope (Olympus) with 494 nm (green, Calcein) and 528 nm (red, EthD-1) emission filters. For quantitative analysis a total of 250 cells were counted from each sample over 25 randomly chosen areas and the viable and non-viable cells counts were recorded. The results are reported in FIGS. 7 and 17.

Example 18

Immunohistochemical Staining of Cytoskeletal Actin and Vinculin

All samples of cell coated substrates (See Example 16 and 17) were pre-fixed in pre-warmed 0.8 mL cell culture media and 1.2 mL 3.7% paraformaldehyde (PFA) in CS buffer for 5 minutes on a dry block at 37° C. After aspiration, samples were fixed in 3.7% PFA solution at 37° C. for 5 minutes. After washing with 1×PBS 3 times, 1.5 mL of Triton X-100 in CS buffer (0.5% v/v) was added to each well to permeabilize the cells for 10 minutes on a dry block at 37° C. The substrates were washed 3 times with 1×PBS. Freshly made 0.1 wt % NaBH$_4$ in 1×PBS was then added for 10 minutes at r.t. to quench the aldehyde fluorescence, followed by aspiration and incubation in 5% donkey serum for 20 minutes at r.t. to block the non-specific binding. After aspiration, the substrates were incubated in vinculin primary antibody Mouse in 1×PBS (v/v 1:200) at 4° C. overnight. After washing with 1% donkey serum 3 times, the substrates were stained in a solution of rhodamine phalloidin (v/v 1:40) and Alexa Flour 488 secondary antibody Mouse (v/v 1:200) for 1 hour at r.t., avoiding light. After washing with 1×PBS 3 times, the nuclei were stained with DAPI in 1×PBS (6 l/10 mL) for 20 minutes at r.t. in the dark. After washing with 1×PBS 3 times to remove excess staining, the samples were mounted and viewed under an IX81 Microscope (Olympus, Center Valley, Pa.) with mercury bulb excitation and the filters of FITC, TRITC and DAPI. The images showed the differences in cell morphology imparted by each concentration.

Example 19

Cell Proliferation Assay

Cell proliferation of MC3T3-E1 cells of Example 16 on OGP-99%, OGP-50% and TiO$_2$ substrates was evaluated by the PrestoBlue Assay (Life technologies, Grand Island, N.Y.) following the provided protocol. The standard curve was prepared in duplicate by seeding cell suspensions at known concentrations into a 24-well plate at least 6 hours before the experiment for full attachment. Nine descending cell concentration and one blank were included in the standard curve. The PrestoBlue solution was prepared by dilution with cell culture medium (v/v 1:9). After aspirating the old medium, 1.5 mL of PrestoBlue solution was added to each well, followed by incubation at 37° C. in the incubator for 2-4 hours. A color change from blue to purple and to pink ultimately was observed during incubation. When the standard curve fluorescence could be fit to a linear line, the samples' fluorescence was read. 100 μL solution was taken from each well in triplicate and placed in a 96-well plate. The change in cell viability was detected by fluorescence intensity (FI) in Plate Reader by excitement at 570 nm and emission at 615 nm. The standard curve was fit with a linear relationship by plotting FI vs Cell Number. The coefficient of determination ($R^2$) was above 0.99.

Example 20

Immunohistochemical Staining of Bone Sialoprotein (BSP) and Osteocalcin (OCN)

All samples of cell coated substrates (Examples 16 and 17) were pre-fixed in pre-warmed 0.8 mL cell culture media and 1.2 mL 3.7% paraformaldehyde (PFA) in CS buffer for 5 minutes on a dry block at 37° C. After aspiration, samples were fixed in 3.7% PFA solution at 37° C. for 5 minutes. After washing with 1×PBS 3 times, blocking buffer (10% normal donkey serum, 0.3% Triton X-100 in 1×PBS) was added into each well and incubated for 45 minutes at r.t. to block the non-specific binding. After aspiration, the substrates were incubated in bone sialoprotein (BSP) primary antibody Mouse (v/v 1:400) and osteocalcin (OCN) primary antibody Goat in 1×PBS (v/v 1:100) overnight at 4° C. After washing with 1% donkey serum 3 times, the substrates were stained by incubation in a solution of Alexa Flour 488 secondary antibody Mouse (v/v 1:200) and Alexa Flour 546 secondary antibody Goat (v/v 1:200) in 1×PBS for 1 hour at r.t. in the dark. After washing with 1% donkey serum 3 times, the nuclei were stained with DAPI in 1×PBS (6 μL/10 mL) for 20 minutes at r.t. avoiding light. After washing with 1×PBS once, the samples were mounted and viewed under an IX81 Microscope (Olympus, Center Valley, Pa.) with mercury bulb excitation and the filters of FITC, TRITC and DAPI. These images showed that the cells having 99% OGP coverage expressed a much higher gene level of BSP and OCN on all of the substrates tested.

Example 21

Alizarin Red S. Staining

Samples of cell coated substrates (Examples 16 and 17) were pre-fixed in pre-warmed 0.8 mL cell culture media and 1.2 mL 3.7% paraformaldehyde (PFA) in CS buffer for 5 minutes on a dry block at 37° C. After aspiration, samples were fixed in 3.7% PFA solution at 37° C. for 5 minutes. Freshly made Alizarin Red S. solution (0.8 g in 40 mL dd H$_2$O, pH adjusted to 4.2), was added into substrates that are washed 3 times with dd H$_2$O to remove soluble calcium. After incubation at r.t. for 40 minutes, the Alizarin Red S. solution was carefully removed. The substrates were washed with double distilled H$_2$O 4 times, mounted and observed under bright field microscope. These images showed significantly higher Ca$^{+2}$ levels for the OGP-99% than the OGP-50% or TiO$_2$ substrates. See FIG. 15C.

Example 22

Alkaline Phosphatase (ALP) Activity Assay

ALP activity was measured by SensoLyte pNPP ALP Assay Kit (AnaSpec Inc, San Jose, Calif., USA) following the provided protocol. The MC3T3-E1 cells on OGP-99%, OGP-50% and $TiO_2$ substrates were washed with 1× Assay Buffer twice. (See FIG. 15A). The cell film was peeled from the substrates and transferred into a 1.5 mL centrifuge tube, followed by addition of 0.5 mL lysis buffer (20 µL Triton X-100 in 10 mL 1× Assay Buffer). The cells was resuspended and incubated in the lysis buffer for 10 min at 2500×g at 4° C. After centrifuge, the supernatant was collected for analysis. A standard curve was measured with an ALP solution at concentrations of 0, 3.1, 6.2, 12.5, 25, 50, 100, 200 ng/mL. 50 µL of sample/standard solution and 50 µL pNPP solution was added into each well in a 96-well plate. The solution was mixed by gently shaking for 30 sec. After incubation for 30 min, the 96-well plate was shaken for 1 min before measuring the absorbance at 405 nm. Three replicates were measured for each sample. The standard curve was fitted with a linear relationship by plotting Ab. vs ALP concentration, with a coefficient of determination ($R^2$) above 0.98. See FIGS. 15A-B.

To normalize the ALP activity with total protein amount, the amount of total protein was quantified with a DC protein assay (Bio-Rad, Hercules, Calif., USA). A standard curve was measure with BSA solution at amount of 0, 0.2, 0.5, 0.8, 1.1, 1.43 mg/mL with 1×ALP Assay Buffer as the dilution buffer. 5 µL of standards and samples were added into a 96-well plate. Then 25 µL of reagent A and 200 µL reagent B were added. The plate was shaken for 30 sec to well mix the solution, which was left to incubate for 15 min. The absorbance at 750 nm was read. The standard curve was fitted with a linear relationship by plotting Ad. vs BSA amount, with a coefficient of determination ($R^2$) above 0.96.

Example 23

Calcium Quantification

The MC3T3-E1 cells on OGP-99%, OGP-50% and $TiO_2$ substrates were washed with DPBS buffer ($Mg^{2+}$, $Ca^{2+}$ free) once. The cell film was peeled from the substrates and transferred into a 1.5 mL centrifuge tube, followed by addition of 300 L double distilled $H_2O$. Three freeze-thaw cycles were carried out to destroy the cell membrane, followed by the addition of 300 µL 1 M HCl. The samples were agitated at r.t. overnight. The concentration of calcium ions in the supernatant was measured with inductively coupled plasma optical emission spectrometry (ICP-OES) (Agilent Technologies 700 series, Santa Clara, Calif., USA). The emission wavelength was set at 393.366 nm to quantify $Ca^{2+}$. A standard curve was measured with solutions of $c(Ca^{2+})$ equal to 0.125, 0.25, 0.5, 1, and 2 ppm. Triplicate measurements were carried out for each sample. The calcium amount of each sample was normalized with total protein amount, which was done in the same way as set forth above for the ALP activity assay. See FIG. 15C.

Example 24

Real Time-Polymerase Chain Reaction (RT-PCT)

Total RNA was isolated from the cell coated substrates (See, Examples 16 and 17) on day 18 with an RNA extraction and isolation kit (Applied Biosystems, Life Technologies), following the provided protocol, and was quantified by ultraviolet spectroscopy. The synthesis of complementary DNA (cDNA) was performed with a high-capacity cDNA reverse transcription kit with RNase inhibitor (Applied Biosystems, Life Technologies) using 800 ng total RNA as the template in a 100 µL reaction following the provided protocol. RT-PCR was performed with non-specific detection fluorescence, SYBR Green, or double-dye probe detection, and TaqMan probes system (Applied Biosystems, Life Technologies). For SYBR Green system, 10 ng of cDNA product and 1×SYBR Green master mixture (Applied Biosystems, Life Technologies) were included in 50 µL reaction mixture (209.4 nM each primer). For TaqMan system, 24 ng of cDNA product and 1× TaqMan master mixture (Applied Biosystems, Life Technologies) were included in 25 µL reaction mixture. The housekeeping gene was glyceraldehyde-3-phosphate dehydrogenase (GAPDH). All oligonucleotide primers (See Table 5, below) were purchased from Applied Biosystems (Life Technologies). The ALP primer (alp1 gene from Mouse) was also purchased from Applied Biosystems (Life Technologies). RT-PCR was performed in the Applied Biosystems Real-Time PCR Instruments—7500 Fast System (Life technologies, Grand Island, N.Y.) with recommended programs by the supplier.

TABLE 5

Primers used to examine OGP (10-14) on cell markers of osteogenic differentiation.

| Primer | Sequence | Sequence direction | Probe |
|---|---|---|---|
| hGAPDH-L1 | gacagtcagccgcatctt (SEQ ID No. 2) | Forward | SYBR Green |
| hGAPDH-R1 | ccatggtgtctgagcgatgt (SEQ ID No. 3) | Reverse | SYBR Green |
| hBSP-L1 | cctggcacagggtatacagg (SEQ ID No. 4) | Forward | SYBR Green |
| hBSP-R1 | ctgcttcgctttcttcgttt (SEQ ID No. 5) | Reverse | SYBR Green |
| hOCN-L1 | gtgcagcctttgtgtccaa (SEQ ID No. 6) | Forward | SYBR Green |
| hOCN-R1 | ggctcccagccattgat (SEQ ID No. 7) | Reverse | SYBR Green |

Figure 18:
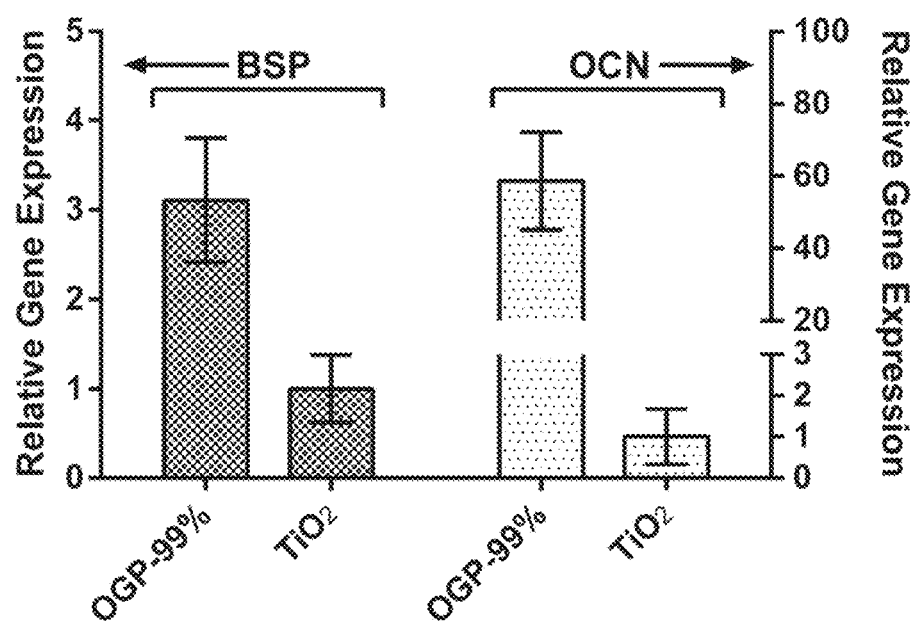
FIG. 18 is a graph showing mRNA levels of transcription factor genes of BSP and OCN, in MC3T3-E1 cells measured by real-time PCR after cell culture for 18 days. Data represent relative expression to the level of the control (cells on TiO$_2$), set at 1, and mean value and standard deviation calculated from triplicates. The cells having 99% OGP coverage (OGP-99% substrate) expressed a much higher gene level of BSP and OCN, compare to cells on bare TiO$_2$.

The results are shown in FIGS. 15B and 18. The data reported in FIG. 18 represents relative expression to the level of the control (cells on TiO$_2$), set at 1, and mean value and standard deviation calculated from triplicates. The cells having 99% OGP coverage (OGP-99% substrate) expressed a much higher gene level of BSP and OCN, compare to cells on bare TiO$_2$.

In light of the foregoing, it should be appreciated that the present invention significantly advances the art by providing a multivalent dendron that is structurally and functionally improved in a number of ways. While particular embodiments of the invention have been disclosed in detail herein, it should be appreciated that the invention is not limited thereto or thereby inasmuch as variations on the invention herein will be readily appreciated by those of ordinary skill in the art. The scope of the invention shall be appreciated from the claims that follow.

What is claimed is:

1. A multivalent dendron comprising a bioactive peptide domain and one or more surface-binding catechol domains and having the formula:

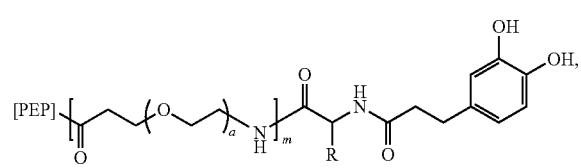

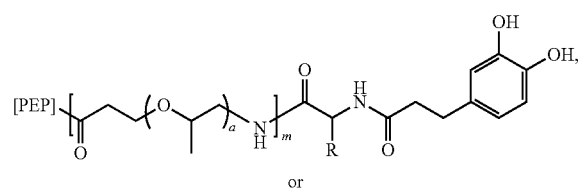

or

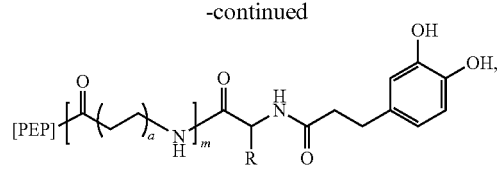

wherein PEP is a bioactive peptide domain of 2-30 amino acids having a specific biological function; R is selected from the group consisting of —$CH_3$, —$(CH_2)_3NHC(NH_2)C=NH$, —$CH_2CONH_2$, —$CH_2COOH$, —$CH_2SH$, —$(CH_2)_2COOH$, —$(CH_2)_2CONH_2$, —$NH_2$, —$CH_2C=CH-N=CH-NH$, —$CH(CH_3)CH_2CH_3$, —$CH_2CH(CH_3)_2$, —$(CH_2)_4NH_2$, —$(CH_2)_2SCH_3$, —$CH_2Ph$, —$CH_2OH$, —$CH(OH)CH_3$, —$CH_2-C=CH-NH-Ph$, —$CH_2$-Ph-OH, —$CH(CH_3)_2$, and combinations thereof; a is an integer from 1 to 20; and m is 0 or 1.

2. A lysine-based multivalent dendron comprising a bioactive peptide domain and one or more surface-binding catechol domains and having the formula:

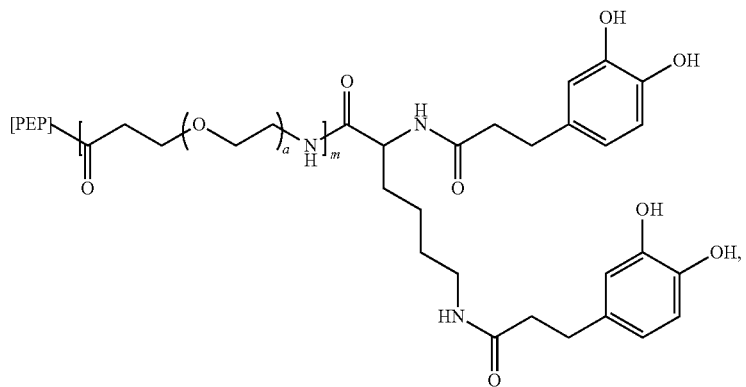
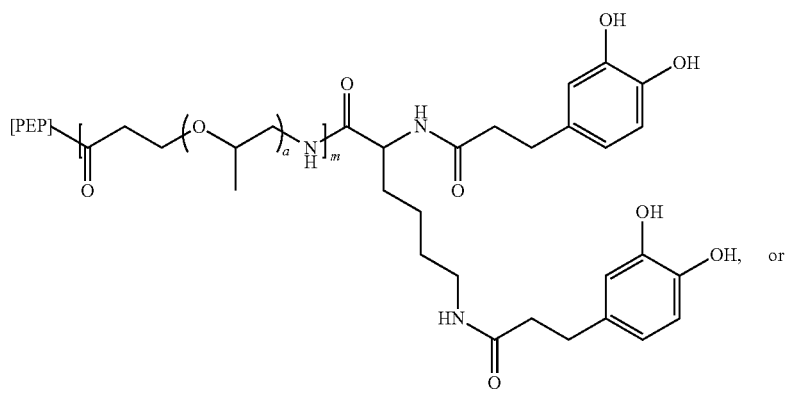
or
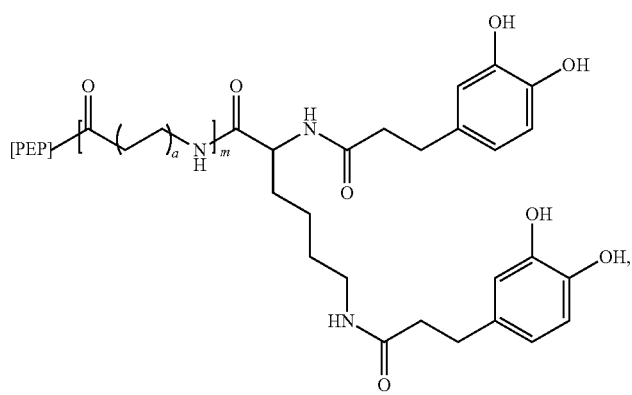
wherein PEP is a bioactive peptide domain of 2-30 amino acids having a specific biological function; a is an integer from 1 to 20 and m is 0 or 1.

3. A lysine-based multivalent dendron comprising a bioactive peptide domain and one or more surface-binding catechol domains and having the formula:
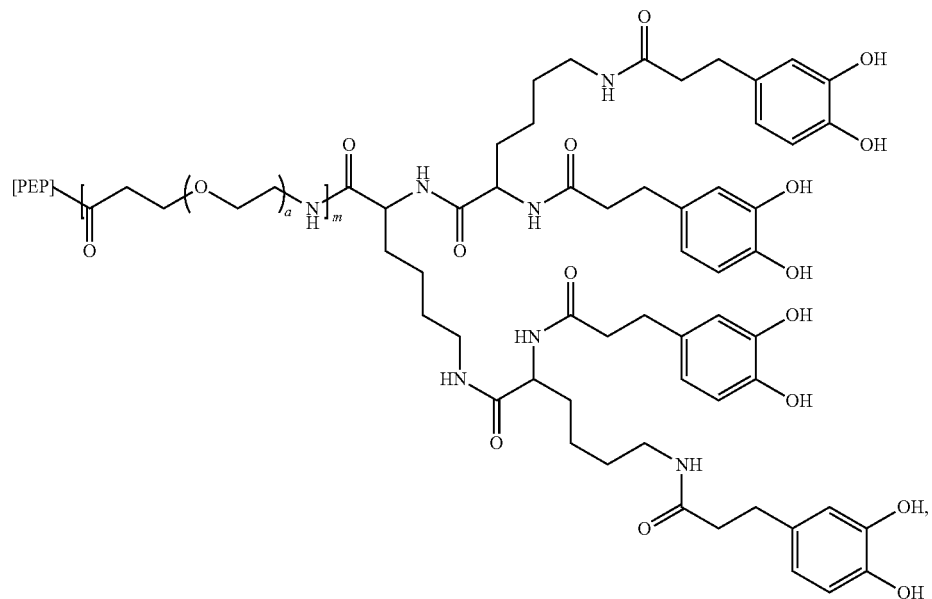
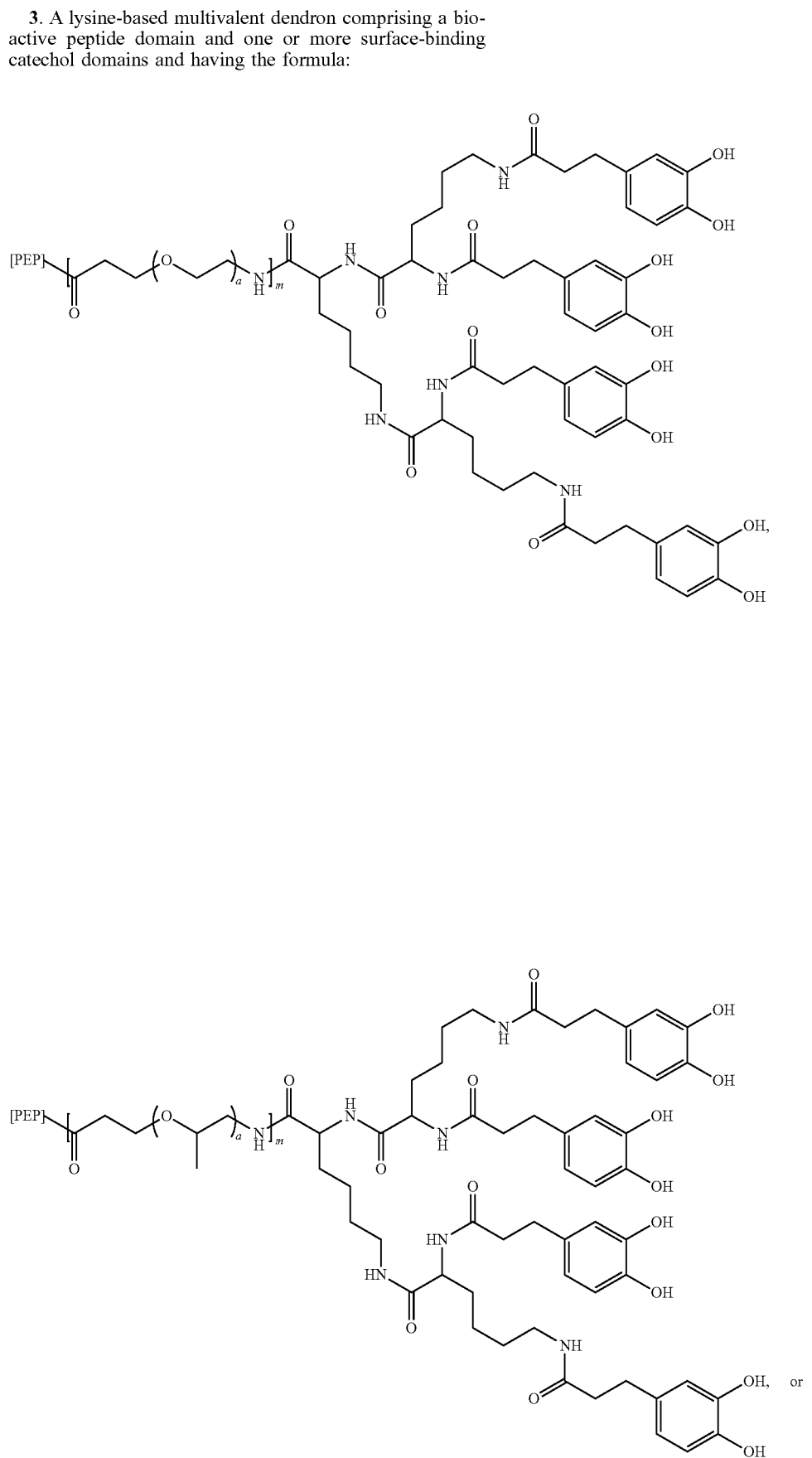

-continued

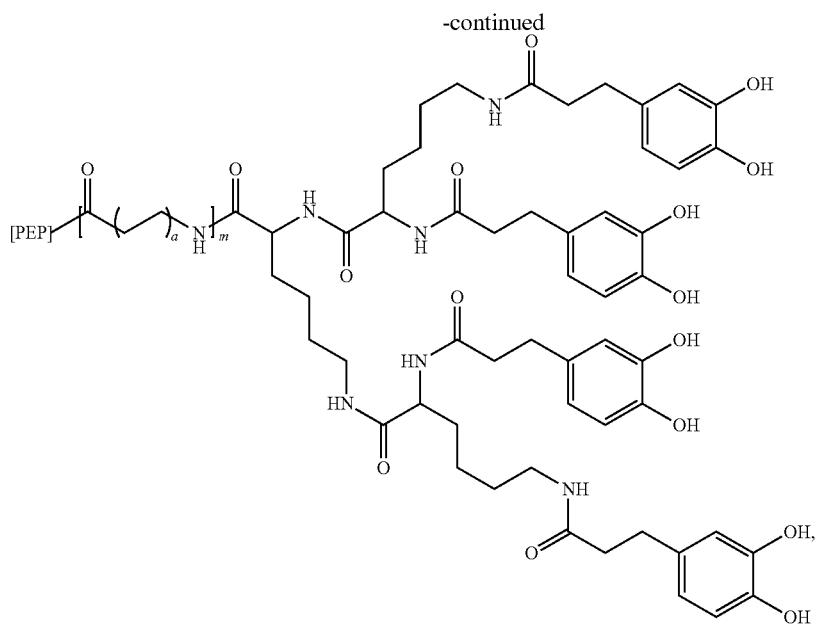

wherein PEP is a bioactive peptide domain of 2-30 amino acids having a specific biological function; a is an integer from 1 to 20; and m is 0 or 1.

4. A lysine-based multivalent dendron having the formula:

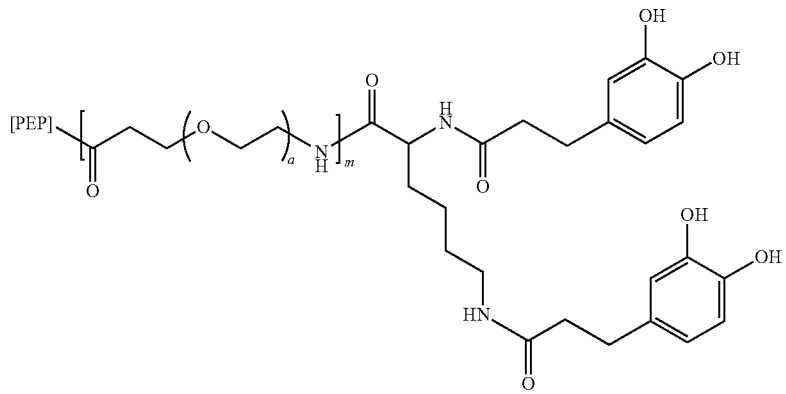

wherein PEP is a bioactive peptide; a is an integer from 1 to 20 and m is 0 or 1.

5. The multivalent dendron of claim 4 wherein said bioactive peptide is selected from the group consisting of: —NH-KIPKASSVPTELSAISTLYL-COOH (SEQ ID No. 1), BMP-2, OGP, OGP C-terminal sequence YGFGG (SEQ ID No. 8), GRGDS (SEQ. ID No. 9), and combinations thereof.

6. The multivalent dendron of claim 4 wherein said bioactive peptide is less than 30 amino acids in length.

7. The multivalent dendron of claim 4 wherein said bioactive peptide is OGP C-terminal sequence YGFGG (SEQ ID No. 8).

8. A lysine-based multivalent dendron having the formula:

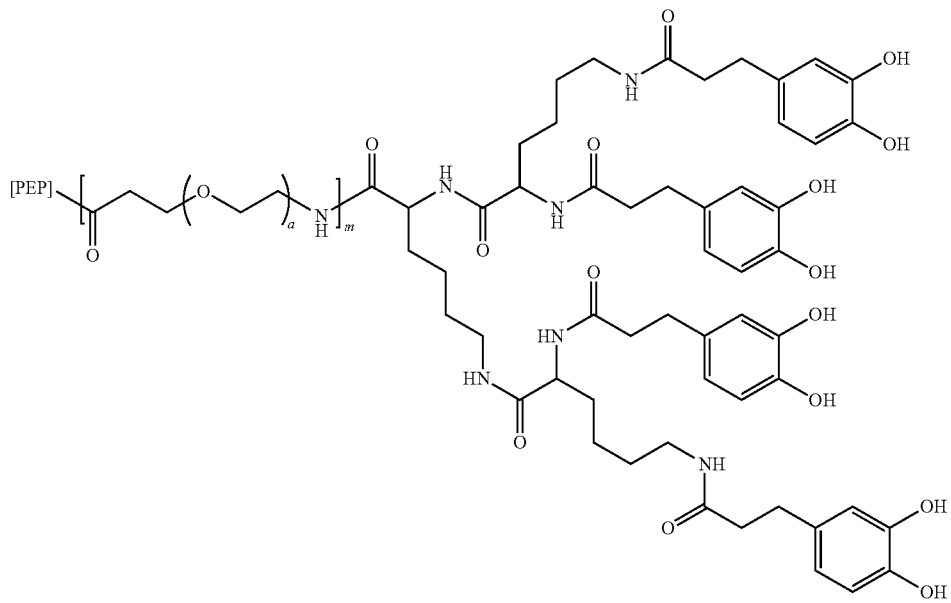

wherein PEP is a bioactive peptide; a is an integer from 1 to 20; and m is 0 or 1.

9. The multivalent dendron of claim 8 wherein said bioactive peptide is selected from the group consisting of: —NH-KIPKASSVPTELSAISTLYL-COOH (SEQ ID No. 1), BMP-2, OGP, OGP C-terminal sequence YGFGG (SEQ ID No. 8), GRGDS (SEQ. ID No. 9), and combinations thereof.

10. The multivalent dendron of claim 8 wherein said bioactive peptide is less than 30 amino acids in length.

11. The multivalent dendron of claim 8 wherein said bioactive peptide is OGP C-terminal sequence YGFGG (SEQ ID No. 8).

12. The lysine-based multivalent dendron of claim 2 having the formula:

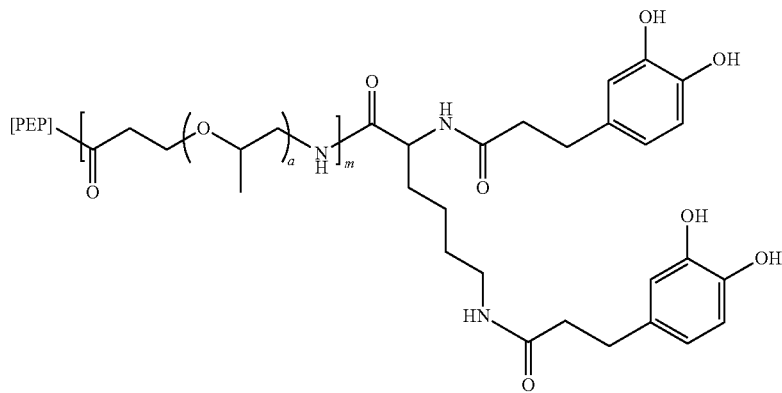

wherein PEP is a bioactive peptide domain of 2-30 amino acids having a specific biological function; a is an integer from 1 to 20 and m is 0 or 1.

13. The lysine-based multivalent dendron of claim 12 wherein said bioactive peptide is selected from the group consisting of: —NH-KIPKASSVPTELSAISTLYL-COOH (SEQ ID No. 1), BMP-2, OGP, OGP C-terminal sequence YGFGG (SEQ ID No. 8), GRGDS (SEQ. ID No. 9), and combinations thereof.

14. The lysine-based multivalent dendron of claim 12 wherein said bioactive peptide is OGP C-terminal sequence YGFGG (SEQ ID No. 8).

15. The lysine-based multivalent dendron of claim 2 having the formula:

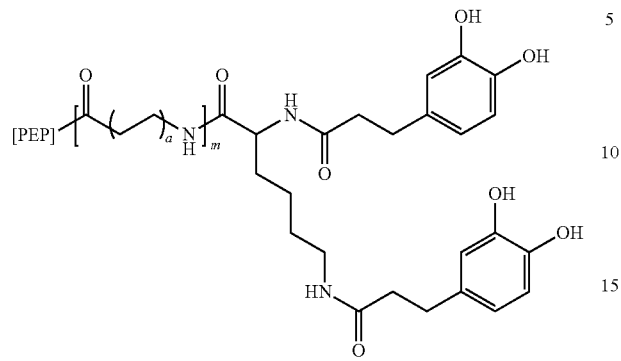

wherein PEP is a bioactive peptide domain of 2-30 amino acids having a specific biological function; a is an integer from 1 to 20 and m is 0 or 1.

16. The lysine-based multivalent dendron of claim 15 wherein said bioactive peptide is selected from the group consisting of: —NH-KIPKASSVPTELSAISTLYL-COOH (SEQ ID No. 1), BMP-2, OGP, OGP C-terminal sequence YGFGG (SEQ ID No. 8), GRGDS (SEQ. ID No. 9), and combinations thereof.

17. The lysine-based multivalent dendron of claim 15 having the formula:

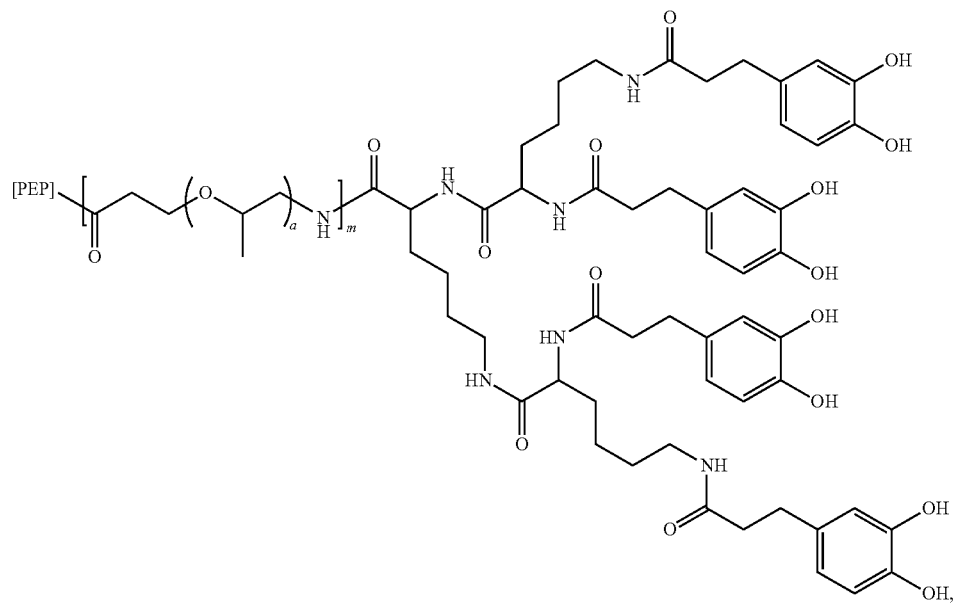

where PEP is a bioactive peptide; a is an integer from 1 to 20; and m is 0 or 1.

18. The lysine-based multivalent dendron of claim 17 wherein said bioactive peptide is selected from the group consisting of: —NH-KIPKASSVPTELSAISTLYL-COOH (SEQ ID No. 1), BMP-2, OGP, OGP C-terminal sequence YGFGG (SEQ ID No. 8), GRGDS (SEQ. ID No. 9), and combinations thereof.

19. The lysine-based multivalent dendron of claim 15 having the formula:

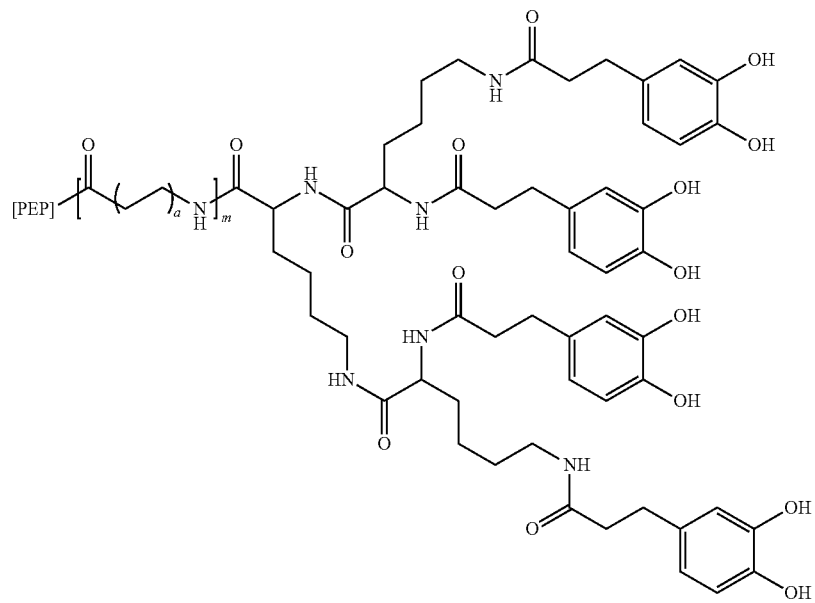

where PEP is a bioactive peptide; a is an integer from 1 to 20; and m is 0 or 1.

20. The lysine-based multivalent dendron of claim 19 wherein said bioactive peptide is selected from the group consisting of: —NH-KIPKASSVPTELSAISTLYL-COOH (SEQ ID No. 1), BMP-2, OGP, OGP C-terminal sequence YGFGG (SEQ ID No. 8), GRGDS (SEQ. ID No. 9), and combinations thereof.

* * * * *